(12) United States Patent
Howard et al.

(10) Patent No.: US 8,637,664 B2
(45) Date of Patent: Jan. 28, 2014

(54) ALKYL 4- [4- (5-OXO-2,3,5, 11A-TETRA-HYDO-5H-PYRROLO [2, 1-C] [1,4] BENZO-DIAZEPINE-8-YLOXY)-BUTYRYLAMINO]-1H-PYRROLE-2-CARBOXYLATE DERIVATIVES AND RELATED COMPOUNDS FOR THE TREATMENT OF A PROLIFERATIVE DISEASE

(75) Inventors: Philip Wilson Howard, London (GB); David Edwin Thurston, London (GB); Geoffrey Wells, London (GB)

(73) Assignee: Spirogen SARL, St-Legier-la Chiesaz (CH)

( * ) Notice: Subject to any disclaimer, the term of this patent is extended or adjusted under 35 U.S.C. 154(b) by 590 days.

(21) Appl. No.: 12/089,459

(22) PCT Filed: Oct. 5, 2006

(86) PCT No.: PCT/GB2006/003718
§ 371 (c)(1),
(2), (4) Date: Apr. 7, 2008

(87) PCT Pub. No.: WO2007/039752
PCT Pub. Date: Apr. 12, 2007

(65) Prior Publication Data
US 2008/0214525 A1    Sep. 4, 2008

Related U.S. Application Data

(60) Provisional application No. 60/724,064, filed on Oct. 6, 2005, provisional application No. 60/723,681, filed on Oct. 5, 2005.

(51) Int. Cl.
C07D 223/10    (2006.01)
A01N 43/62    (2006.01)
A61K 31/55    (2006.01)

(52) U.S. Cl.
USPC ............................... 540/485; 514/220

(58) Field of Classification Search
USPC ............................... 540/485; 514/220
See application file for complete search history.

(56) References Cited

U.S. PATENT DOCUMENTS

| | | | |
|---|---|---|---|
| 5,229,490 A | 7/1993 | Tam | |
| 6,187,797 B1 | 2/2001 | Pruitt et al. | |
| 6,562,806 B1 | 5/2003 | Thurston et al. | |
| 6,608,192 B1 | 8/2003 | Thurston et al. | |
| 6,747,144 B1 | 6/2004 | Thurston et al. | |
| 6,909,006 B1 | 6/2005 | Thurston et al. | |
| 7,049,311 B1 | 5/2006 | Thurston et al. | |
| 7,067,511 B2 | 6/2006 | Thurston et al. | |
| 7,265,105 B2 | 9/2007 | Thurston et al. | |
| 7,407,951 B2 | 8/2008 | Thurston et al. | |
| 7,429,658 B2 | 9/2008 | Howard et al. | |
| 2003/0195196 A1 | 10/2003 | Thurston et al. | |
| 2004/0092736 A1 | 5/2004 | Thurston et al. | |
| 2004/0138269 A1 | 7/2004 | Sun et al. | |
| 2004/0198722 A1 | 10/2004 | Thurston et al. | |
| 2007/0173497 A1 | 7/2007 | Howard et al. | |
| 2007/0185073 A1 | 8/2007 | Howard et al. | |
| 2007/0191309 A1 | 8/2007 | Howard et al. | |
| 2007/0191349 A1 | 8/2007 | Howard et al. | |
| 2007/0249591 A1 | 10/2007 | Howard et al. | |
| 2008/0090812 A1 | 4/2008 | Pepper et al. | |

(Continued)

FOREIGN PATENT DOCUMENTS

| | | |
|---|---|---|
| JP | 55069587 | 5/1980 |
| JP | 58180487 | 10/1983 |
| WO | 2006/111759 | 10/2006 |
| WO | 2010/010347 | 1/2010 |
| WO | 2010/043880 | 4/2010 |

OTHER PUBLICATIONS

Yalamati Damayanthi, et al, Design and Synthesis of Novel Pyrrolo[2,1-c][1,4]benzodiazepine-Lexitropsin Conjugates, 64 J Org. Chem. 290 (1999).*

(Continued)

*Primary Examiner* — Sean Basquill
(74) *Attorney, Agent, or Firm* — Michael Best & Friedrich LLP

(57) ABSTRACT

A compound of formula (I); or a salt or solvate thereof, wherein: the dotted line indicates the optional presence of a double bond between C2 and C3; $R^2$ is selected from —H, —OH, =O, =$CH_2$, —CN, —R, OR, halo, =CH—R, O—$SO_2$—R, $CO_2R$ and COR; $R^7$ is selected from H, R, OH, OR, SH, SR, $NH_2$, NHR, NRR', nitro, $Me_3Sn$ and halo, where R and R' are independently selected from optionally substituted $C_{1-7}$ alkyl, $C_{3-20}$ heterocyclyl and $C_{5-20}$ aryl groups; $R^{10}$ and $R^{11}$ either together form a double bond, or are selected from H and $YR^Y$, where Y is selected from O, S and NH and R is H or $C_{1-7}$ alkyl or H and $SO_xM$, where x is 2 or 3 and M is a monovalent pharmaceutically acceptable cation; each X is independently a heteroarylene group; n is from 1 to 6; and $R^E$ is $C_{1-4}$ alkyl. The compound is useful for the treatment of proliferative diseases.

(I)

7 Claims, 7 Drawing Sheets

(56) References Cited

U.S. PATENT DOCUMENTS

| | | |
|---|---|---|
| 2008/0167293 A1 | 7/2008 | Howard et al. |
| 2010/0113425 A1 | 5/2010 | Howard et al. |
| 2011/0160192 A1 | 6/2011 | Howard et al. |
| 2011/0162227 A1 | 7/2011 | Howard et al. |
| 2011/0196148 A1 | 8/2011 | Howard et al. |

OTHER PUBLICATIONS

Guojian Xie, et al, Bisindolylmaleimides Linked to DNA Minor Groove Binding Lexitropsins: Synthesis, Inhibitory Activity Against Topoisomerase I, and Biological Evaluation, 39 J Med. Chem. 1049 (1996).*

Arima et al., "Studies on Tomaymycin, a New Antibiotic. I. Isolation and Properties of Tomaymycin," *J. Antibiotics* (1972) 25:437-444.

Baird, E.E. et al., "Solid phase synthesis of polyamides containing imidazole and pyrrole amino acids," J. Am. Chem. Soc. (1996) 118(26):6141-6146.

Baraldi, P.G. et al., "[2,1-c][1,4]benzodiazepine (PBD)-distamycin hybrid inhibits DNA binding to transcription factor Sp1," Nucleotides and Nucleic Acids (2000) 19(8):1219-1229.

Baraldi, P.G. et al., "Design, synthesis and biological activity of a pyrrolo[2,1-c][1,4]benzodiazepine (PBD)—distamycin hybrid," *Bioorganic & Medicinal Chemistry Letters*, vol. 8, No. 21, 3019-3024 (1998).

Baraldi, P.G. et al., "Synthesis, in Vitro Antiproliferative Activity, and DNA-Binding Properties of Hybrid Molecules Containing Pyrrolo[2,1-c][1,4]benzodiazepine and Minor-Groove-Binding Oligopyrrole Carriers," *J. Med. Chem.*, 42, 5131-5141 (1999).

Berge et al., "Pharmaceutical Salts," J. Pharm. Sci. (1977) 66:1-19.

Borgatti, M. et al., "Inhibition of NF-kB/DNA interactions and HIV-1 LTR directed transcription by hybrid molecules containing pyrrolo [2,1-c][1,4] benzodiazepine (PBD) and oligopyrrole carriers," Drug Development Research (2003) 60(3):173-185.

Bose et al., "New Approaches to Pyrrolo[2,1-c][1,4]benzodiazepines: Synthesis, DNA-binding and cytotoxicity of DC-81," *Tetrahedron*, 48, 751-758 (1992).

Briehn, C.A. et al., "Alternative heterocycles for DNA recognition: the benzimidazole/imidazole pair," Chem. Eur. J. (2003) 9:2110-2122.

Damayanthi, Y., et al., "Design and synthesis of novel pyrrolo{2,1-c}[1,4] benzodiazepine-Lexitropsin Conjugates," *J. Org. Chem.*, 64, 290-292 (1999).

Dangles, O. et al., "Selective Cleavage of the Allyl and Allyloxycarbonyl Groups through Palladium-Catalyzed Hydrostannolysis with Tributyltin Hydride. Application to the Selective Protection-Deprotection of Amino Acid Derivatives and in Peptide Synthesis," *J. Org. Chem.*, 52, 4984-4993 (1987).

Edman, P. and Begg, G., "A Protein Sequenator," *Eur. J. Biochem.*, 1, 80-91 (1967).

Firth, J.D. et al., "Oxygen-regulated control elements in the phosphoglycerate kinase 1 and lactate dehydrogenase A genes: similarities with the erythropoietin 3' enhancer," Proc. Natl. Acad. Sci. USA (1994) 91:6496-6500.

Furka, A. et al., "Combinatorial libraries by portioning and mixing," Combin. Chem. & High Throughput Screening (1999) 2:105-122.

Furka, A. et al., "General method for rapid synthesis of multicomponent peptide mixtures," *Int. J. Peptide Protein Res.*, 37, 487-493 (1991).

Gallop, M.A. et al., "Applications of combinatorial technologies to drug discovery. 1. Background and peptide combinatorial libraries," J. Med. Chem. (1994) 37(9):1233-1251.

Gordon, E.M. et al., "Applications of combinatorial technologies to drug discovery. 2. Combinatorial organic synthesis, library screening strategies, and future directions," J. Med. Chem. (1994) 37(10):1385-1401.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J. Med. Chem.*, 44: 737-748 (2001).

Hara et al., "DC 102, a new glycosidic pyrrolo(1,4)benzodiazepine antibiotic produced by *streptomyces* sp.", *J. Antibiotics*, 41, 702-704 (1988).

Hochlowski, J. et al., "Abbeymycin, a new anthramycin-type antibiotic produced by a streptomycete," *J. Antibiotics*, 40, 145-148 (1987).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).

Itoh et al., "Sibanomicin, a new pyrrolo(1,4)benzodiazepine antitumor antibiotic produced by a *micromonospora* sp." *J. Antibiotics*, 41, 1281-1284 (1988).

Jones, G.B. et al., "The non-covalent interaction of pyrrolo[2, 1-c][1,4]benzodiazepine-5, 11-diones with DNA," Anti-Cancer Drug Design (1990) 5:249-264.

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J. Antibiotics*, 37, 200-206 (1984).

Kumar, R. et al., "Design and synthesis of novel pyrrolo[2,1-c][1,4]benzodiazepine—imidazole containing polyamide conjugates," Heterocyclic Communications (2002) 81(1):19-26.

Kumar, R. et al., "Design, synthesis and in vitro cytotoxicity studies of novel pyrrolo [2,1][1,4]benzodiazepine-glycosylated pyrrole and imidazole polyamide conjugates," Org. Biomol. Chem. (2003) 1(19):3327-3342.

Kumar, R. et al., "Synthesis and antitumor cytotoxicity evaluation of novel pyrrolo[2,1-c][1,4]benzodiazepine imidazole containing polyamide conjugates," Oncology Research (2003) 13(4):221-233.

Kunimoto et al., "Mazethramycin, a new member of anthramycin group antibiotics," *J. Antibiotics*, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Leber, J.D. et al., "A revised structure for sibiromycin," *J. Am. Chem. Soc.*, 110, 2992-2993 (1988).

Leimgruber, W. et al., "Isolation and characterization of anthramycin, a new antitumor antibiotic," *J. Am. Chem. Soc.*, 87, 5791-5793 (1965).

Leimgruber, W. et al., "The structure of anthramycin," *J. Am. Chem. Soc.*, 87, 5793-5795 (1965).

Lescrinier, T. et al., "DNA-Binding Ligands from Peptide Libraries Containing Unnatural Amino Acids," *Chem. Eur. J.*, 4, 3, 425-433 (1998).

Manzini, G. et al., "Interaction of diamidino-2-phenylindole (DAPI) with natural and synthetic nucleic acids," Nuc. Acids. Res. (1983) 11(24):8861-8876.

Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

McConnaughie, A.W. et al., "Novel acridine-triazenes as prototype combilexins: synthesis, DNA binding and biological activity," J. Med. Chem. (1995) 38:3488-3501.

Mischiati, C. et al., "Binding of hybrid molecules containing pyrrolo [2,1-c][1,4]benzodiazepine (PBD) and oligopyrrole carriers to the human immunodeficiency type 1 virus TAR-RNA," Biochem. Pharmacol. (2004) 67(3):401-410.

Paikoff, S.J. et al., "The Solid Phase Synthesis of N-Alkylcarbamate Oligomers", *Tetrahedron Letters*, 37, No. 32: 5653-5656 (1996).

Reddy et al., "Design, synthesis and in vitro cytotoxicity studies of novel pyrrolo[2,1-c][1,4]benzodiazepine (PBD)-polyamide conjugates and 2,2'-PBD dimers," Anti-Cancer Drug Design (2000) 15(3):225-238.

Shimizu, K et al., "Prothracarcin, a Novel Antitumor Antibiotic," *J. Antibiotics*, 35, 972-978 (1982).

Soth, M.J. and Nowick, J.S., "Unnatural oligomers and unnatural oligomer libraries", *Curr. Opin. Chem. Biol.*, 1:120-129 (1997).

Takeuchi, T. et al., "Neothramycins A and B, New Antitumor Antibiotics," *J. Antibiotics*, 29, 93-96 (1976).

(56) References Cited

OTHER PUBLICATIONS

Tercel, M. et al., "Unsymmetrical DNA cross-linking agents: combination of the CBI and PBD pharmacophores," J. Med. Chem. (2003) 46:2132-2151.
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Topiol, S. et al., "Computer aided analysis of split and mix combinatorial libraries," J. Comb. Chem. (2001) 3:20-27.
Tsunakawa, M. et al., "Porothramycin, a new antibiotic of the anthramycin group: Production, isolation, structure and biological activity," J. Antibiotics, 41:1366-1373 (1988).
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wells, G. et al., "Pyrrolobenzodiazepine-polyamide libraries: synthesis and DNA binding selectivity," Proc. Am. Assoc. Canc. Res. (2003) 44:85-86, #452.
Woods, C.R. et al., "Synthesis and DNA binding properties of iminodiacetic acid-linked polyamides: characterization of cooperative extended 2:1 side-by-side parallel binding," J. Am. Chem. Soc. (2002) 124:10676-10682.
United States Office Action for U.S. Appl. No. 09/763,813 dated Sep. 10, 2002 (11 pages).
United States Office Action for U.S. Appl. No. 09/763,813 dated Feb. 28, 2003 (8 pages).
United States Office Action for U.S. Appl. No. 09/763,813 dated May 21, 2003 (7 pages).
United States Office Action for U.S. Appl. No. 09/763,767 dated May 23, 2002 (20 pages).
United States Office Action for U.S. Appl. No. 09/763,767 dated Nov. 15, 2002 (19 pages).
United States Office Action for U.S. Appl. No. 09/763,767 dated May 20, 2003 (11 pages).
United States Office Action for U.S. Appl. No. 09/763,767 dated Jan. 14, 2004 (11 pages).
United States Office Action for U.S. Appl. No. 09/763,767 dated Aug. 4, 2004 (7 pages).
United States Office Action for U.S. Appl. No. 09/763,767 dated Jun. 9, 2005 (5 pages).
United States Office Action for U.S. Appl. No. 11/367,241 dated Jun. 22, 2006 (11 pages).
United States Office Action for U.S. Appl. No. 11/367,241 dated Nov. 24, 2006 (16 pages).
United States Office Action for U.S. Appl. No. 09/763,814 dated Sep. 13, 2001 (16 pages).
United States Office Action for U.S. Appl. No. 09/763,814 dated Apr. 23, 2002 (23 pages).
United States Office Action for U.S. Appl. No. 09/763,814 dated Jul. 24, 2002 (8 pages).
United States Office Action for U.S. Appl. No. 09/763,814 dated Sep. 23, 2002 (8 pages).
United States Office Action for U.S. Appl. No. 09/673,768 dated Dec. 14, 2001 (7 pages).
United States Office Action for U.S. Appl. No. 09/673,768 dated Jul. 12, 2002 (4 pages).
United States Office Action for U.S. Appl. No. 09/673,768 dated Dec. 24, 2002 (4 pages).
United States Office Action for U.S. Appl. No. 10/021,213 dated May 20, 2003 (10 pages).
United States Office Action for U.S. Appl. No. 10/379,049 dated Mar. 21, 2005 (14 pages).
United States Office Action for U.S. Appl. No. 10/379,049 dated Oct. 5, 2005 (17 pages).
United States Office Action for U.S. Appl. No. 10/379,049 dated Apr. 26, 2006 (9 pages).
United States Office Action for U.S. Appl. No. 10/602,521 dated Sep. 24, 2007 (12 pages).
United States Office Action for U.S. Appl. No. 10/602,521 dated Mar. 26, 2008 (8 pages).
United States Office Action for U.S. Appl. No. 10/602,521 dated May 31, 2008 (8 pages).
United States Office Action for U.S. Appl. No. 10/602,521 dated Jul. 15, 2008 (7 pages).
United States Office Action for U.S. Appl. No. 10/602,521 dated Dec. 10, 2008 (12 pages).
United States Office Action for U.S. Appl. No. 10/824,743 dated Jul. 31, 2006 (6 pages).
United States Office Action for U.S. Appl. No. 10/824,743 dated Jan. 17, 2007 (15 pages).
United States Office Action for U.S. Appl. No. 10/824,743 dated Oct. 9, 2007 (12 pages).
United States Office Action for U.S. Appl. No. 10/534,825 dated Sep. 7, 2006 (7 pages).
United States Office Action for U.S. Appl. No. 10/534,825 dated Mar. 2, 2007 (7 pages).
United States Office Action for U.S. Appl. No. 10/534,825 dated Sep. 20, 2007 (4 pages).
United States Office Action for U.S. Appl. No. 10/571,274 dated Oct. 31, 2007 (6 pages).
United States Office Action for U.S. Appl. No. 10/598,470 dated May 23, 2008 (6 pages).
United States Office Action for U.S. Appl. No. 10/598,482 dated May 22, 2008 (9 pages).
United States Office Action for U.S. Appl. No. 10/598,482 dated Nov. 24, 2008 (6 pages).
United States Office Action for U.S. Appl. No. 10/598,691 dated Mar. 21, 2008 (7 pages).
United States Office Action for U.S. Appl. No. 10/598,691 dated Sep. 29, 2008 (6 pages).
United States Office Action for U.S. Appl. No. 11/569,007 dated Oct. 15, 2008 (12 pages).
Firsching, A. et al., "Antiproliferative and angiostatic activity of suramin analogues," Cancer Res. (1995) 55:4957-4961.
United States Office Action for U.S. Appl. No. 10/602,521 dated Sep. 9, 2009 (14 pages).
United States Office Action for U.S. Appl. No. 10/598,518 dated Sep. 28, 2009 (6 pages).
United States Patent Office Action for U.S. Appl. No. 10/591,140 dated Jan. 19, 2010 (7 pages).
United States Office Action for U.S. Appl. No. 10/598,518 dated Mar. 13, 2009 (7 pages).
United States Patent Office Action for U.S. Appl. No. 12/610,478 dated Aug. 6, 2010 (14 pages).
Dupont, C. et al., "Synthesis of rhazinilam analogue acting as an inhibitor of tubulin assembly," Tetrahedron Lett. (2000) 41:5853-5856.
Wolff, M.E., Burger's Medicinal Chemistry, 4th Edition, Part I, Wiley: New York (1979) 336-337.
United States Office Action for U.S. Appl. No. 11/569,007 dated Jun. 1, 2009 (10 pages).
United States Office Action for U.S. Appl. No. 10/591,140 dated Jul. 6, 2009 (16 pages).
United States Patent Office Action for U.S. Appl. No. 10/602,521 dated Sep. 9, 2009 (14 pages).
United States Patent Office Action for U.S. Appl. No. 10/598,518 dated Sep. 28, 2009 (6 pages).
United States Patent Office Action for U.S. Appl. No. 12/610,478 dated Dec. 17, 2010 (5 pages).
United States Patent Office Action for U.S. Appl. No. 10/591,140 dated Dec. 6, 2010 (7 pages).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Antonow, D. et al.,"Parallel synthesis of a novel C2-aryl pyrrolo[2,1-c][1,4]benzodiazepine (PBD) library," J. Comb. Chem. (2007) 9:437-445.

(56) References Cited

OTHER PUBLICATIONS

Fey, T. et al., "Silica-supported TEMPO catalyst: synthesis and application in the anelli oxidation of alcohols," J. Org. Chem. (2001) 66:8154-8159.

Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem. (2009) in Press, 4 pages.

Hu, W-P. et al., "An efficient synthesis of pyrrolo[2,1-c][1,4]benzodiazepine. Synthesis of the antibiotic DC-81," J. Org. Chem. (2001) 66:2881-2883.

United States Patent Office Action for U.S. Appl. No. 12/610,478 dated Jul. 22, 2011 (7 pages).

International Search Report and Written Opinion for Application No. PCT/GB2009/001819 dated Oct. 29, 2009 (8 pages).

International Search Report and Written Opinion for Application No. PCT/US2011/032668 dated May 26, 2011 (12 pages).

Banker, G.S. et al., Modern Pharmaceutics, Third Edition, Marcel Dekker, New York (1996) 451 and 596.

Dorwald, F.Z., Side Reactions in Organic Synthesis: a Guide to Successful Synthesis Design, Weinheim: Wiley-VCH Verlag GmbH and Co., KGaA (2005) Preface.

Gavezzotti, A., "Are crystal structures predictable?" Acc. Chem. Res. (1994) 27:309-314.

Jordan, V.C., "Tamoxifen: a most unlikely pioneering medicine," Nature Reviews: Drug Discovery (2003) 2:205-213.

Souillac, P. et al., "Characterization of delivery systems, differential scanning calorimetry," Encyclopedia of Controlled Drug Delivery (1999) 212-227.

Vippagunta, S.R. et al., "Crystalline solids," Adv. Drug Delivery Rev. (2001) 48:3-26.

Wolff, M.E., Burger's Medicinal Chemistry, 5th Edition, Part I, John Wiley & Sons, New York (1995) 975-977.

United States Patent Office Action for U.S. Appl. No. 13/041,849 dated Dec. 1, 2011 (24 pages).

United States Patent Office Action for U.S. Appl. No. 13/041,849 dated Jun. 6, 2012 (13 pages).

United States Patent Office Action for U.S. Appl. No. 13/041,849 dated Aug. 22, 2012 (8 pages).

\* cited by examiner

ALKYL 4-[4-(5-OXO-2,3,5,11A-TETRA-HYDO-5H-PYRROLO [2,1-C] [1,4] BENZO-DIAZEPINE-8-YLOXY)-BUTYRYLAMINO]-1H-PYRROLE-2-CARBOXYLATE DERIVATIVES AND RELATED COMPOUNDS FOR THE TREATMENT OF A PROLIFERATIVE DISEASE

CROSS-REFERENCE TO RELATED APPLICATIONS

This patent application is a national stage filing under 35 U.S.C. 371 of International Application No. PCT/GB2006/003718, filed on Oct. 5, 2006, which claims priority to U.S. Provisional Application Nos. 60/724,064, filed on Oct. 6, 2005 and 60/723,681, filed on Oct. 5, 2005. These applications are incorporated herein by reference in their entireties.

The present invention relates to pyrrolobenzodiazepines (PBDS) and in particular to PBD monomers and methods of synthesising PBD monomers.

BACKGROUND TO THE INVENTION

Some pyrrolobenzodiazepines (PBDS) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 35, 972-978 (1982); Langley and Thurston, *J. Org. Chem.*, 52, 91-97 (1987)), sibanomicin (DC-102) (Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

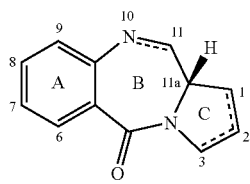

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

A number of conjugates of PBD with pyrroles and imidazoles have been reported.

Lown has reported (Damayanthi, Y., et al., *Journal of Organic Chemistry*, 64(1), 290-292 (1999)) the synthesis of PBD conjugates (named PBD-lexitropsin conjugates):

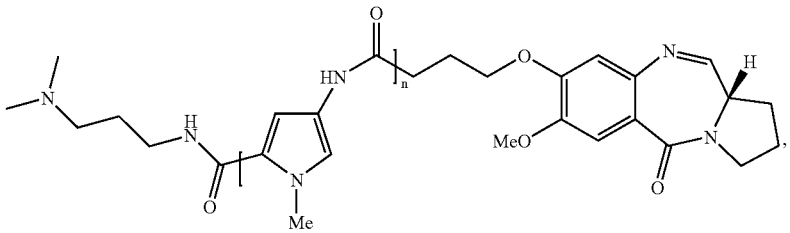

wherein n=1-3 with a propyl linker and an N-dimethylaminopropyl terminus. Although these are stated to be lexitropsin derivatives with the n=2 and 3 analogues mimicking the 2 and 3 N-methylpyrrole rings of netropsin and distamycin, respectively, the N-dimethylaminopropyl tail differs significantly from the guanidine methyl or guanidine ethyl tails of netropsin or distamycin, respectively. The compounds, which were produced in an overall yield of 28-30% as a mixture of the N10-C11 imine and carbinolamine methyl ether forms. They were found to be highly polar as the imines and only soluble in a mixture of chloroform and methanol, and were insufficiently soluble in either solvent to allow production of pure imine or methyl ether forms. The compounds with n=2 and 3 were reported (Reddy, B. S. P., et al., *Anti-Cancer Drug Design*, 15(3), 225-238 (2000)) to have modest cytotoxicity with values ranging from 7.5-86.5 µM (for n=2) and 0.9-93 µM (for n=3).

Lown has also reported (Kumar, R. and Lown, J. W. *Oncology Research*, 13(4), 221-233 (2003)); Kumar, R., et al., *Heterocyclic Communications*, 8(1), 19-26 (2002)) the synthesis of three equivalent imidazole analogues:

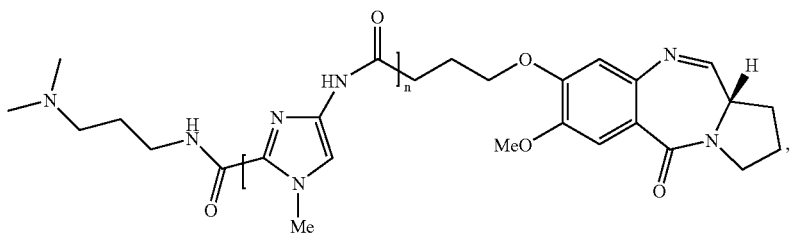

wherein n=1-3 and two mixed pyrrole-imidazole analogues:

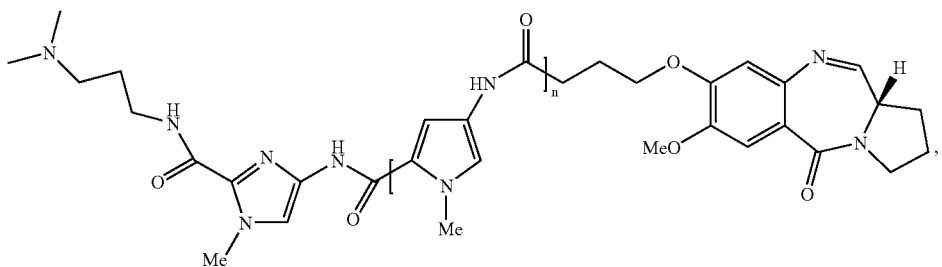

wherein n=1-2. These compounds, obtained in overall yields of 35-40% were also produced as mixtures of imines and carbinolamine methyl ethers in a 1:1 ratio, and had similar solubility characteristics. In the NCI 60 panel screen, the mixed compound (n=1) was not active in any cell lines, and the other compounds had mean $GI_{50}$, TGI and $LC_{50}$ values in the range 16.22-95.50 µM.

In an effort to enhance water solubility, Lown and co-workers more recently reported (Kumar, R., et al., *Organic & Biomolecular Chemistry*, 1(19), 3327-3342 (2003)) a set of sixteen PBD-heterocycle conjugates containing varying numbers of pyrrole and imidazole units but with heterocycles glycosylated on their ring nitrogens. In eight of these molecules the hydroxyl moieties of the glycosyl units were fully acetylated. The other eight were similar in structure except that all acetyl groups had been removed. Data from the NCI panel indicate that these compounds are significantly less cytotoxic than the corresponding compounds with glycosyl units. Also, although the group of compounds which are deacetylated are designed to be more water soluble than those which are acetylated, the average $IC_{50}$ values show only a marginal improvement which in fact appears to be due to just one compound which shows a marked improvement (0.588 µM) over its non-deacetylated equivalent (93.3 µM). No DNA-binding data has been reported for any of these conjugates.

Baraldi and co-workers have reported (Baraldi, P. G., et al., *Bioorganic & Medicinal Chemistry Letters*, 8(21), 3019-3024 (1998)) the synthesis of a conjugate of a PBD and distamycin:

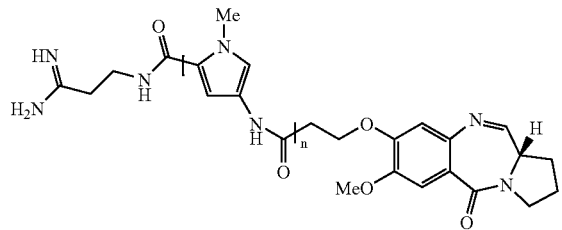

where n=3, which differs from the conjugates synthesized by Lown in having a two-methylene linker between the PBD and first heterocycle rather than three, and in possessing a guanidine terminus as found in the natural products distamycin and netropsin rather than the dimethylaminopropyl terminus of the Lown compounds. Interestingly, this compound appeared to be more cytotoxic than the Lown conjugates with an $IC_{50}$ in K562 cells of 0.2 µM. The DNA binding of the conjugate was assessed in a PCR-based assay against DNA sequences that were GC-rich (Ha-ras oncogene) or AT-rich (oestrogen, ER) receptor. Unlike Distamycin A which inhibited PCR in only the AT-rich sequence, the compound was equipotent in inhibiting PCR in both the GC-rich and AT-rich DNAs at a level 6× more potent than Distamycin in the AT-rich sequence. Baraldi also reported (Baraldi, P. G., et al., *Journal of Medicinal Chemistry*, 42(25), 5131-5141 (1999)) an extended set of the compound above containing one to four pyrrole units (n=1-4). Cytotoxicity evaluations in K562 (>100 µM [n=1] to 0.04 µM [n=4]) and Jurkat (80 µM [for n=1] to 0.07 µM [for n=4]) cell lines showed that increase in the length of the polypyrrole backbone led to an increase of in vitro activity. Only the n=3 and 4 compounds were more potent than either the PBD fragment alone or the relevant tetrapyrrole devoid of PBD. To investigate sequence selectivity and stability of the drug/DNA complexes, DNase I footprinting and arrested polymerase chain reaction (PCR) were performed on fragments of the human c-myc oncogene and human immunodeficiency virus type 1 long terminal repeat (HIV-1 LTR) (both GC-rich), and the estrogen receptor gene (AT-rich). It was found that the ability of the compounds to arrest PCR of the c-myc gene ($IC_{50}$=2-6 µM) and HIV gene ($IC_{50}$=0.8-2.0 µM) was higher than distamycin A (25 µM for C-myc; 50 µM for HIV), suggesting that the presence of the PBD might be favouring a shift to GC-recognition. Interestingly, for the ER gene, compounds with n=1 or 2 were similar ($IC_{50}$=3.0 µM, 2.0 µM, respectively) to distamycin ($IC_{50}$=5 µM), whereas compounds with n=3 or 4 were marginally more active (0.8 µM, 0.2 µM, respectively) suggesting that there was a more profound effect on raising GC-selectivity. Analysis of arrest sites of ER PCR suggested that the compound where n=1 arrests at 5'-AGTTTAAA-3', whereas the compounds where n=2-4 cause arrest at the same site and in addition at 5'-CATATATGTGTG-3'. Footprinting experiments suggested that comparing these compounds, similar footprints were obtained suggesting that changes in the number of pyrrole rings did not produce significant changes in sequence recognition. However, it was noted that the footprints generated by the compound where n=4 were larger than that generated by distamycin. Finally, using a PCR-based dialysis experiment, it was demonstrated that these hybrid compounds exhibit different DNA-binding activity with respect to both distamycin and the parent PBD. In addition, a direct relationship was found between number of pyrrole rings present in the hybrids and stability of drug/DNA complexes. Confirming the previous studies of Baraldi, Gambari and co-workers reported (Borgatti, M., et al., *Drug Development Research*, 60(3), 173-185 (2003)) the effects of these compounds on the interaction between purified NF-κB and [$^{32}$P]-labelled oligomers mimicking the NF-κB HIV-1 LTR binding sites using both gel retardation (EMSA) and filter binding assays. The results showed that the conjugates were effective in inhibiting NF-κB p52/NF-κB DNA interactions according to the EMSA assay but only compounds where n=2-4 were active according to the filter assay. Similarly, conjugates where n=2-4 (but not n=1) were shown to efficiently inhibit HIV-1 LTR driven transcription in vitro whereas the PBD fragment alone was not. Baraldi and co-workers (Baraldi, P. G., et al., *Nucleosides Nucleotides & Nucleic Acids*, 19(8), 1219-1229 (2000)) also reported that the compound where n=3 inhibits binding of the transcription factor Sp1, a protein important for the control of transcription of cellular and viral genes, to its cognate DNA sequence. Nuclear proteins were isolated from K562 cells and immobilised on a filter after electrophoresis. The ability of the compound where n=3 to inhibit the binding of [$^{32}$P]-labelled Sp1 oligomer to the filter was then studied. Although the PBD fragment or distamycin A failed to inhibit binding at concentrations of up to 50 μM, the compound where n=3 completely blocked the Sp1/DNA binding interaction at 10 μM, a result which was confirmed by gel shift experiments.

Finally, Gambari and co-workers have reported (Mischiati, C., et al., *Biochemical Pharmacology*, 67(3), 401-410 (2004)) that these compounds bind to TAR-RNA and inhibit TAR/protein(s) interaction, and also interact with structured TAR-RNA of HIV-1. The authors studied the effects of these compounds on protein/TAR-RNA interactions in vitro by both EMSA and filter binding experiments using nuclear extracts and Tat, and ex vivo using the HL3T1 cell line as a cellular system to study Tat-induced HIV-1 LTR driven transcription. The compounds bind TAR-RNA since they slow down migration of radiolabelled HIV-1 TAR-RNA, whereas distamycin A and the PBD fragment are inactive. In the EMSA experiments, binding of the compounds to either the structured AU-rich or GC-rich RNA was less efficient than to wild type TAR-RNA. Again the PBD fragment and distamycin A were inactive. Denaturing experiments suggested that the compounds where n=1 and 2 might be binding non-covalently to the DNA whereas the compounds where n=3 and 4 might be binding covalently. They also reported IC$_{50}$ values in HL3T1 cells (72 hours) confirming earlier observed trends of cytotoxicity increasing with increasing numbers of pyrrole units attached.

Some of the present inventors have previously disclosed (Wells, G., et al., *Proc. Am. Assoc. Canc. Res.*, 2003, 44, 452) the following compound:

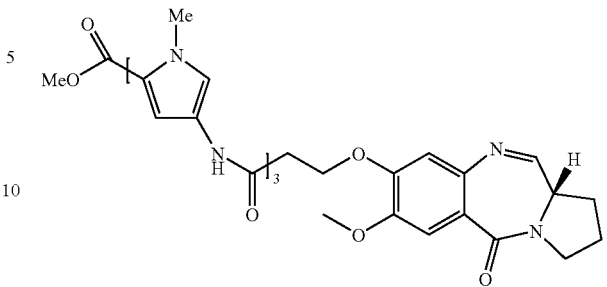

The inventors have now discovered that the properties, particularly cytoxicity and DNA binding, of the prior art compounds can be improved.

A first aspect of the present invention provides a compound of formula I:

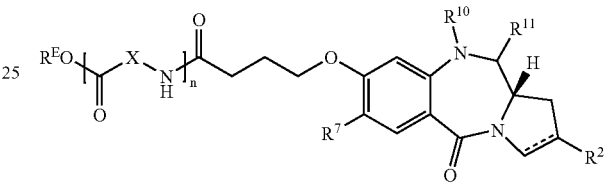

or a salt or solvate thereof, wherein:
the dotted line indicates the optional presence of a double bond between C2 and C3;
$R^2$ is selected from —H, —OH, =O, =CH$_2$, —CN, —R, OR, halo, =CH—R, O—SO$_2$—R, CO$_2$R and COR;
$R^7$ is selected from H, R, OH, OR, SH, SR, NH$_2$, NHR, NRR', nitro, Me$_3$Sn and halo;
where R and R' are independently selected from optionally substituted C$_{1-7}$ alkyl, C$_{3-20}$ heterocyclyl and C$_{5-20}$ aryl groups;
$R^{10}$ and $R^{11}$ either together form a double bond, or are selected from H and YR$^Y$, where Y is selected from O, S and NH and R$^Y$ is H or C$_{1-7}$ alkyl or H and SO$_x$M, where x is 2 or 3, and M is a monovalent pharmaceutically acceptable cation;
each X is independently a heteroarylene group;
n is from 1 to 6;
$R^E$ is C$_{1-4}$ alkyl.

A second aspect of the present invention provides a compound of formula II:

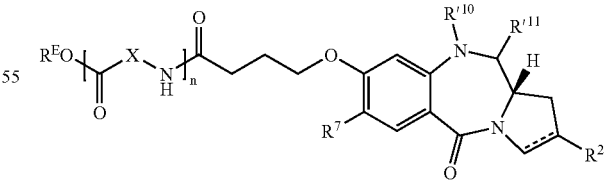

wherein:
the dotted line indicates the optional presence of a double bond between C2 and C3;
$R^2$ is selected from —H, —OH, =O, =CH$_2$, —CN, —R, OR, halo, =CH—R, O—SO$_2$—R, CO$_2$R and COR;
$R^7$ is selected from H, R, OH, OR, SH, SR, NH$_2$, NHR, NRR', nitro, Me$_3$Sn and halo;

where R and R' are independently selected from optionally substituted $C_{1-7}$ alkyl, $C_{3-20}$ heterocyclyl and $C_{5-20}$ aryl groups;
$R'^{10}$ is a nitrogen protecting group and $R'^{11}$ is $O—R^{12}$, wherein $R^{12}$ is H or a hydroxyl protecting group;
each X is independently a heteroarylene group;
n is from 1 to 6;
$R^E$ is $C_{1-4}$ alkyl.

A third aspect of the present invention provides a method of synthesis of a compound of formula I comprising the deprotection of a compound of formula II.

A fourth aspect of the present invention provides a pharmaceutical composition comprising a compound of the first aspect of the invention and a pharmaceutically acceptable carrier or diluent.

A fifth aspect of the present invention provides a compound of the first aspect for use in a method of therapy.

A sixth aspect of the present invention provides the use of a compound of the first aspect of the invention in the manufacture of a medicament for the treatment of a proliferative disease.

A seventh aspect of the present invention provides a method of treatment of a patient suffering from a proliferative disease, comprising administering to said patient a therapeutically acceptable amount of a compound of the first aspect or a composition of the fourth aspect.

Definitions
Heteroarylene Group

X is an optionally substituted heteroarylene group, preferably a $C_{5-16}$ heteroarylene group, more preferably a $C_{5-10}$ heteroarylene group and even more preferably a $C_{5-6}$ heteroarylene group. Furthermore in a preferred embodiment, the X group is a five membered heteroarylene group. The term "heteroarylene", as used herein, pertains to a divalent moiety obtained by removing two hydrogen atoms from aromatic ring atoms of a heteroaromatic compound. Heteroarylene compounds as described herein correspond to heteroaryl groups as defined below with one fewer hydrogen atoms on the ring atoms.

The heteroarylene group (X) may contain one or more heteroatoms and preferably contains one heteroatom. The one or more heteroatoms in the heteroarylene group (X) are independently chosen from N, O and S and are preferably N.

The heteroarylene group (X) is optionally substituted with one or more R groups. In a preferred embodiment the X group is substituted at one or more of the heteroatom positions with at least one R group, most preferably the R group is a methyl or ethyl group.

The adjoining carbonyl and amino groups may be attached to the heteroarylene group (X) at any two of the heteroarylene atoms, and preferably at two separate carbon atoms in the heteroarylene ring.

Where the X group is a six membered heteroarylene group, the carbonyl and amino groups are preferably attached at the 2,6, 2,5, 3,6 or 3,5 positions.

Where the X group is a five membered heteroarylene group, the carbonyl and amino groups are preferably attached at the 2,5, 2,4 or 3,5 positions.

Where the X group comprises two fused rings, the carbonyl and amino groups are preferably attached to different rings.

Nitrogen Protecting Groups

Nitrogen protecting groups are well known in the art. Preferred nitrogen protecting groups are carbamate protecting groups that have the general formula:

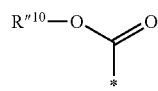

A large number of possible carbamate nitrogen protecting groups are listed on pages 503 to 549 of Greene, T. W. and Wuts, G. M., Protective Groups in Organic Synthesis, 3rd Edition, John Wiley & Sons, Inc., 1999, which is incorporated herein by reference.

Particularly preferred protecting groups include Alloc, Troc, Teoc, BOC, Doc, Hoc, TcBOC, Fmoc, 1-Adoc and 2-Adoc.

Also suitable for use in the present invention are nitrogen protecting groups which can be removed in vivo (e.g. enzymatically, using light) as described in WO 00/12507, which is incorporated herein by reference. Examples of these protecting groups include:

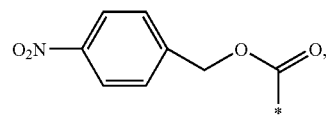

which is nitroreductase labile (e.g. using ADEPT/GDEPT);

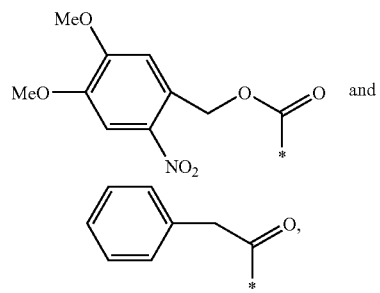

which are photolabile; and

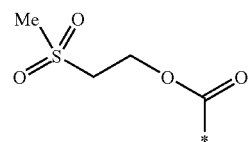

which is glutathione labile (e.g. using NPEPT).

Hydroxyl Protecting Groups

Hydroxyl protecting groups are well known in the art. A large number of suitable groups are described on pages 23 to 200 of Greene, T. W. and Wuts, G. M., Protective Groups in Organic Synthesis, $3^{rd}$ Edition, John Wiley & Sons, Inc., 1999, which is incorporated herein by reference.

Classes of particular interest include silyl ethers, methyl ethers, alkyl ethers, benzyl ethers, esters, benzoates, carbonates, and sulfonates.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-7}$ alkyl: The term "$C_{1-7}$ alkyl" as used herein, pertains to a monovalent moiety obtained by removing a hydrogen atom from a carbon atom of a hydrocarbon compound having from 1 to 7 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-7}$ Alkenyl: The term "$C_{2-7}$ alkenyl" as used herein, pertains to an alkyl group having one or more carbon-carbon double bonds.

Examples of unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl ($C_5$), and hexenyl ($C_6$).

$C_{2-7}$ alkynyl: The term "$C_{2-7}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —CH$_2$—C≡CH).

$C_{3-7}$ cycloalkyl: The term "$C_{3-7}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{15}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_6$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to $C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole (N3), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.
Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).
Acetal: —CH($OR^1$)($OR^2$), wherein $R^1$ and $R^2$ are independently acetal substituents, for example, a $C_{1-7}$ alkyl group, a $C_{3-20}$ heterocyclyl group, or a $C_{6-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR($OR^1$)($OR^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)($OR^1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.
Thione (thioketone): =S.
Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.
Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—$NH_2$), secondary (—$NHR^1$), or tertiary (—$NHR^1R^2$), and in cationic form, may be quaternary (—$^+NR^1R^2R^3$). Examples of amino groups include, but are not limited to, —$NH_2$, —$NHCH_3$, —$NHC(CH_3)_2$, —$N(CH_3)_2$, —$N(CH_2CH_3)_2$, and —NH Ph. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)$N(CH_3)_2$, —C(=O)$NHCH_2CH_3$, and —C(=O)$N(CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)$NR^1R^2$, wherein $R^1$ and $R^2$ are independently amino substituents, as defined for amino groups. Examples of amido groups include, but are not limited to, —C(=S)$NH_2$, —C(=S)$NHCH_3$, —C(=S)N$(CH_3)_2$, and —C(=S)$NHCH_2CH_3$.

Acylamido (acylamino): —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

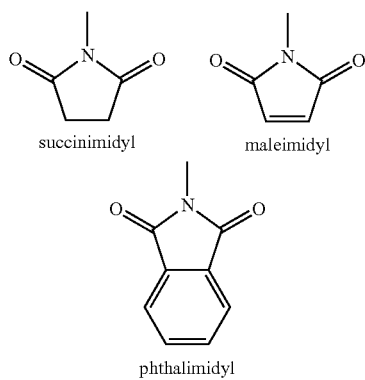

succinimidyl    maleimidyl phthalimidyl

Aminocarbonyloxy: —OC(=O)$NR^1R^2$, wherein $R^1$ and $R^2$ are independently amino substituents, as defined for amino groups. Examples of aminocarbonyloxy groups include, but are not limited to, —OC(=O)$NH_2$, —OC(=O)NHMe, —OC(=O)$NMe_2$, and —OC(=O)$NEt_2$.

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —$NHCONH_2$, —NHCONHMe, —NHCONHEt, —$NHCONMe_2$, —$NHCONEt_2$, —$NMeCONH_2$, —NMeCONHMe, —NMeCONHEt, —$NMeCONMe_2$, and —$NMeCONEt_2$.

Guanidino: —NH—C(=NH)$NH_2$.

Tetrazolyl: a five membered aromatic ring having four nitrogen atoms and one carbon atom,

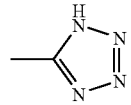

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)$NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)$NH_2$, —C(=NH)$NMe_2$, and —C(=NMe)$NMe_2$.

Nitro: —$NO_2$.

Nitroso: —NO.

Azido: —$N_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)$CH_3$ and —S(=O)$CH_2CH_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$$CH_3$ (methanesulfonyl, mesyl), —S(=O)$_2$$CF_3$ (triflyl), —S(=O)$_2$$CH_2CH_3$ (esyl), —S(=O)$_2$$C_4F_9$ (nonaflyl), —S(=O)$_2$$CH_2CF_3$ (tresyl), —S(=O)$_2$$CH_2CH_2NH_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylaminonaphthalen-1-ylsulfonate (dansyl).

Sulfinic acid (sulfino): —S(=O)OH, —$SO_2$H.

Sulfonic acid (sulfo): —S(=O)$_2$OH, —$SO_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Proliferative Diseases

One of ordinary skill in the art is readily able to determine whether or not a candidate compound treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Methods of Treatment

As described above, the present invention provide the use of a compound of the first aspect of the invention in a method of therapy.

The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy. If the compound of formula I or II bears a carbamate-based nitrogen protecting group which may be removed in vivo, then the methods of treatment described in WO 00/12507 (ADEPT, GDEPT and PDT) may be used.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of the present invention have the following stereochemistry at the C11 position:

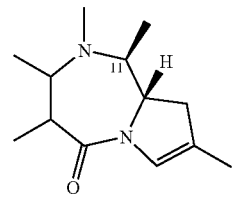

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

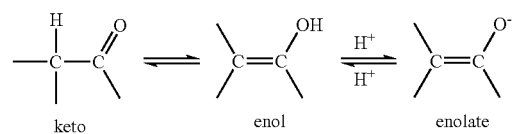

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

across the imine bond of the PBD moiety, which is illustrated below where the solvent is water or an alcohol ($R^4OH$, where $R^4$ is an ether substituent as described above):

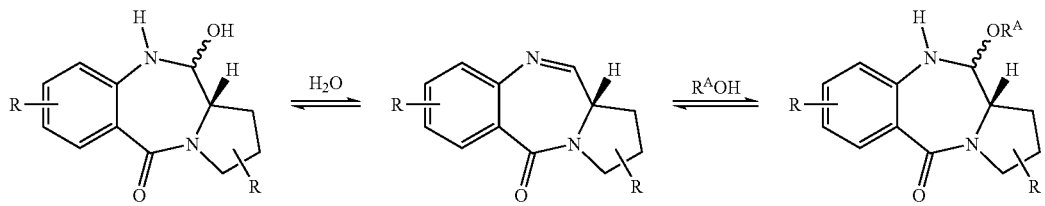

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Compounds of formula I include compounds where a nucleophilic solvent ($H_2O$, $R^4OH$, $R^4NH_2$, RASH) adds These forms can be called the carbinolamine and carbinolamine ether forms of the PBD. The balance of these equilibria depend on the conditions in which the compounds are found, as well as the nature of the moiety itself.

These compounds may be isolated in solid form, for example, by lyophilisation.

General Synthetic Routes

Compounds of formula I where $R^{10}$ and $R^{11}$ together form a double bond may be synthesised from compounds of formula II by removing the nitrogen and hydroxyl, if present, protecting groups from the corresponding compound of formula II. Such techniques are well known in the art, and are described, for example, in Greene, T. W. and Wuts, G. M., Protective Groups in Organic Synthesis, 3$^{rd}$ Edition, John Wiley & Sons, Inc., 1999. If both nitrogen and hydroxyl protecting groups are present, these are preferably selected to be removable by the same conditions.

If this deprotection is carried out in a solvent of formula $HYR^Y$, then $R^{10}$ and $R^{11}$ will be H and $YR^Y$ respectively. Alternatively, these groups may be introduced by adding the compound to a different solvent to that in which the deprotection is carried out.

The conversion of compounds of formula I as discussed above to those having $R^{11}$ as $SO_xM$ may be achieved by the addition of the appropriate bisulphite salt or sulphinate slat, followed by a purification step. Further methods are described in GB 2 053 894, which is herein incorporated by reference.

Compounds of formula II can be made by the coupling of compounds of Formula 3 and Formula 4:

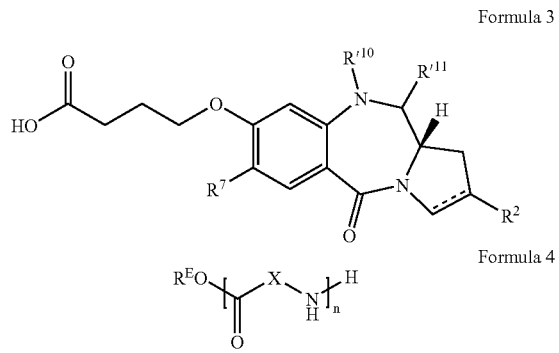

Formula 3

Formula 4 under standard amide bond formation conditions, e.g. in the presence of HOBt or DMAP and EDCI. In the compound of formula 3, R'12 is preferably a hydroxyl protecting group.

Compounds of formula 3 can be synthesised in general following the methods described in WO 00/12506, which is herein incorporated by reference. In particular, the butanoic acid side chain can be introduced at any stage in the synthesis, usually with appropriate protecting groups in place. For example, the side chain can be formed by coupling a protected or precursor form to a hydroxy group on the benzene ring using e.g. Mitsunobo coupling.

Compounds of formula 4 can be synthesised by coupling the desired number of units of formula 5:

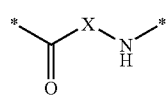

Formula 5 to a compound of formula 6:

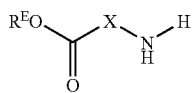

Formula 6

Compounds of formula 6 are commercially available or readily synthesisable.

In order to achieve the addition of units of formula 5 in a controlled manner, these units are usually in the form of a compound of formula 7:

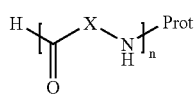

Formula 7 where Prot is an appropriate nitrogen protecting group, such as Boc. A compound of formula 7 is coupled to the compound of formula 6 under standard amide coupling conditions, following which the protecting group is removed. This yields a compound of formula 4, to which further units may be coupled, as desired. The compounds of formula 4 may be built up adding single units of formula 5 at a time, or by the addition of multiple units.

Further Preferences $R^2$ is preferably selected from =$CH_2$, =CH—R, where R is more preferably an optionally substituted $C_{1-4}$ alkyl group, and —R, where R is more preferably an optionally substituted $C_{5-20}$ aryl group. Particularly preferred groups for $R^2$ include =$CH_2$, =CH-Me, and an optionally substituted phenyl group.

$R^7$ is preferably independently selected from H, OR, SH, SR, $NH_2$, NHR, NRR', and halo, and more preferably independently selected from H and OR, where R is preferably selected from optionally substituted $C_{1-7}$ alkyl, $C_{3-10}$ heterocyclyl and $C_{5-10}$ aryl groups. Preferably $R^7$ is OMe or H and most preferably OMe.

In some embodiments, it is preferred that $R^{10}$ and $R^{11}$ either form a double bond together or $R^{11}$ is selected from H and $OR^Y$, where $R^Y$ is H or Me. In other embodiments, it is preferred that $R^{11}$ is $SO_3M$.

$R'^{10}$ is preferably selected from BOC, Troc or alloc. $R'^{11}$ is preferably THP or a silyl oxygen protecting group (for example TBS) and is most preferably THP.

$R^E$ is preferably $C_{1-2}$ alkyl, and more preferably methyl.

A preferred class of heteroarylene groups are those having 5 ring atoms, and more preferred are those having heteroatoms selected from N and S, of which N is preferred.

If a N ring atom is present having an N-substituent, the N-substitutent is preferably a $C_{1-4}$ alkyl group, which is more preferably methyl.

A particularly preferred sub-class of heteroarylene groups comprises the following three units:

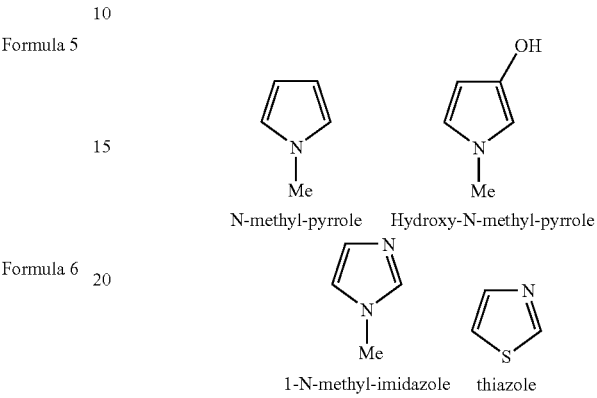

of which N-methyl-pyrrole, N-methyl-imidazole and thiazole are more preferred.

Other preferred heteroarylene groups include those based on 2-(pyrrol-2-yl)benzimidazoles, 2(pyrrol-2-yl)imiazopyridines and 5-hydroxy(pyrrol-2-yl)benzimadozles.

n is preferably from 2 to 6, more preferably 2 to 5, and most preferably 2 to 3.

FIGURES

Figure 1:
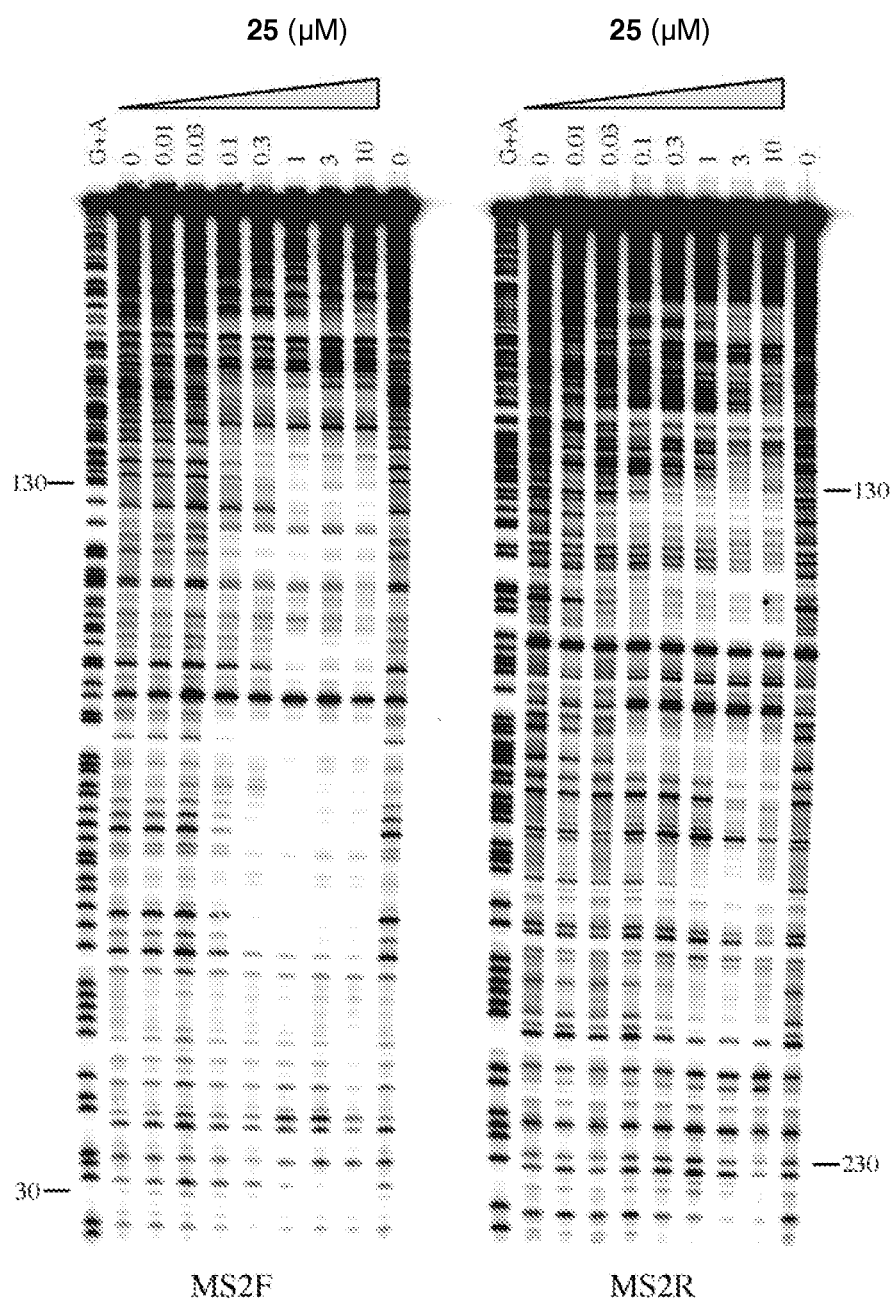
FIG. 1 shows a Dnase I footprint gel of 26, the left panel being forward-labelled MS2 DNA, the right panel being reverse-labelled MS2 DNA; strong footprints are indicated by italicised letters adjacent to the binding sites.

EXAMPLES $^1$H-NMR spectra were acquired using a Bruker Advance400 spectrometer at 400 Hz. Coupling constants are quoted in hertz (Hz). Chemical shifts are reported in parts per million (ppm) downfield from tetramethylsilane. Spin multiplicities are described as a s (singlet), br s (broad singlet), d (doublet), dd (doublet of doublets), t (triplet), q (quartet), quint (quintet), and m (multiplet). LC-MS analysis was performed 1.5 mL/min and a linear gradient solvent system going from 95:5 solvent A:B at time 0 to 5:95 A:B at 4 minutes after sample injection then maintained at 5:95 until 7 minutes. Solvent A is 0.1% formic acid in water, solvent B is 0.1% formic acid in acetonitrile. The electrospray mass spectrometer was operated in switching mode to obtain both positive and negative ion spectra.

Flash chromatography was performed using Merck Kieselgel 60 F254 silica gel. Extraction and chromatography solvents were bought and used without further purification from Fisher Scientific, UK. All chemicals were purchased from Aldrich, Lancaster or BDH.

Example 1

Synthesis of Key Intermediates

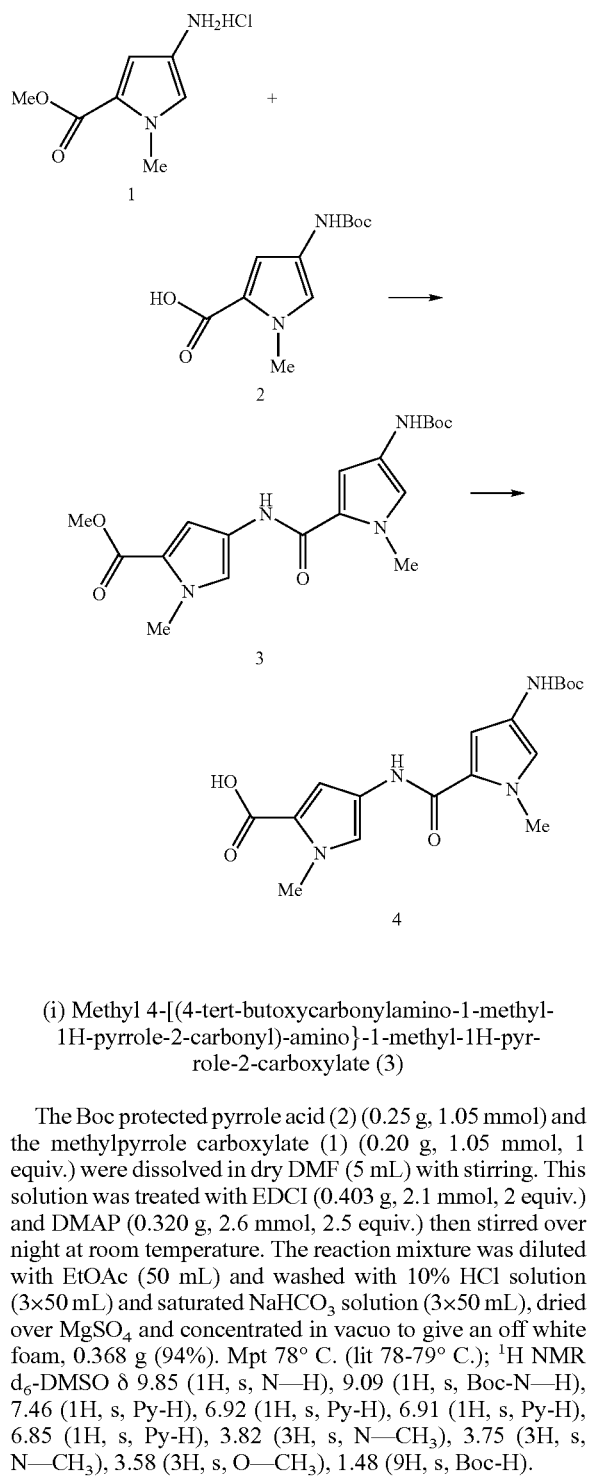

(i) Methyl 4-[(4-tert-butoxycarbonylamino-1-methyl-1H-pyrrole-2-carbonyl)-amino}-1-methyl-1H-pyrrole-2-carboxylate (3)

The Boc protected pyrrole acid (2) (0.25 g, 1.05 mmol) and the methylpyrrole carboxylate (1) (0.20 g, 1.05 mmol, 1 equiv.) were dissolved in dry DMF (5 mL) with stirring. This solution was treated with EDCI (0.403 g, 2.1 mmol, 2 equiv.) and DMAP (0.320 g, 2.6 mmol, 2.5 equiv.) then stirred over night at room temperature. The reaction mixture was diluted with EtOAc (50 mL) and washed with 10% HCl solution (3×50 mL) and saturated NaHCO$_3$ solution (3×50 mL), dried over MgSO$_4$ and concentrated in vacuo to give an off white foam, 0.368 g (94%). Mpt 78° C. (lit 78-79° C.); $^1$H NMR d$_6$-DMSO δ 9.85 (1H, s, N—H), 9.09 (1H, s, Boc-N—H), 7.46 (1H, s, Py-H), 6.92 (1H, s, Py-H), 6.91 (1H, s, Py-H), 6.85 (1H, s, Py-H), 3.82 (3H, s, N—CH$_3$), 3.75 (3H, s, N—CH$_3$), 3.58 (3H, s, O—CH$_3$), 1.48 (9H, s, Boc-H).

(ii) 4-[(4-tert-Butyloxycarbonylamino-1-methyl-1H-pyrrole-2-carbonyl)-amino]-1-methyl-1H-pyrrole-2-carboxylic acid (4)

A stirred solution of Boc pyrrole dimer (3) (0.805 g, 2.1 mmol) in MeOH (40 mL) was treated with 1M NaOH solution (25 mL). The reaction mixture was stirred at room temperature for 18 hours. The volume was reduced in vacuo and the aqueous solution extracted with EtOAc (50 mL). The solvent was removed from the EtOAc fraction and the residue was treated with 1M NaOH solution (10 mL) for a further 3 hours. This was combined with the previous aqueous fraction and acidified to pH2-3 with 1M HCl solution and the suspension extracted with EtOAc (3×75 mL). The organic fractions were combined, dried over MgSO$_4$ and concentrated in vacuo to give a yellow foam 0.781 g (100%). $^1$H NMR d$_6$-DMSO δ 12.07 (1H, bs, OH), 9.81 (1H, s, N—H), 9.08 (1H, s, N—H), 7.40 (1H, d, J=1.9 Hz, Py-H), 6.88 (1H, s, Py-H), 6.84 (1H, s, Py-H), 6.83 (1H, s, Py-H), 3.81 (3H, s, N—CH$_3$), 3.80 (3H, s, N—CH$_3$), 1.45 (9H, s, Boc-H); $^{13}$C NMR d$_6$-DMSO δ 171.9, 161.9, 158.3, 152.8, 122.6, 122.3, 120.2 (CH), 119.4, 117.0 (CH), 108.3 (CH), 103.7 (CH), 78.3, 36.1 (CH$_3$), 36.1 (CH$_3$), 28.1 ([CH$_3$]$_3$).

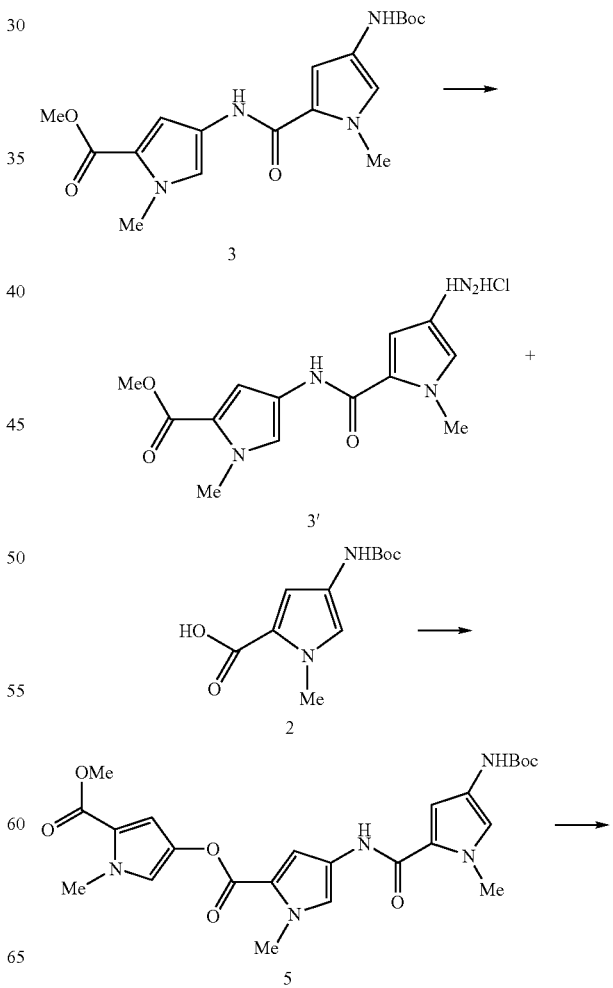

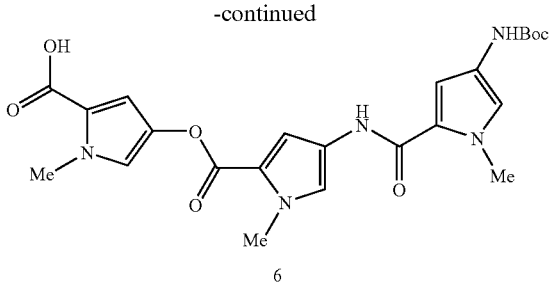

6

(iii) Methyl 4-({4-[(4-tert-butoxycarbonylamino-1-methyl-1H-pyrrole-2-carbonyl)-amino]-1-methyl-1H-pyrrole-2-carbonyl}-amino)-1-methyl-1H-pyrrole-2-carboxylate (5)

The Boc protected pyrrole dimer (3) (0.25 g, 0.66 mmol) was placed in a dry round bottomed flask and treated with 4M HCl in dioxane (5 mL). The resulting solution became cloudy over a period of 30 minutes. The solvent was removed in vacuo to give a yellow solid (3') which was then dried under vacuum. The residue was dissolved in dry DMF (9 mL) and the Boc pyrrole acid (2) (0.176 g, 0.726 mmol, 1.1 equiv.) was added followed by EDCI (0.191 g, 0.99 mmol, 1.5 equiv.) and DMAP (0.097 g, 0.79 mmol, 1.2 equiv.). The reaction mixture was stirred at room temperature for 18 hours then diluted with EtOAc (50 mL) and washed with 1M HCl soln (3×50 mL), then saturated NaHCO$_3$ solution (3×50 mL), dried over MgSO$_4$ then concentrated in vacuo to give a tan foam. This solid was suspended in a 1:1 mixture of MeOH and 1M NaOH solution (40 mL) and stirred at room temp for 30 minutes. EtOAc was added and the organic layer washed with saturated NaHCO$_3$ solution (3×50 mL) and dried over MgSO$_4$. Concentration in vacuo gave an off white foam 0.160 g (48%). Mp 134° C. (lit 131-133° C.); $^1$H NMR d$_6$-DMSO δ 9.90 (1H, s, N—H), 9.86 (1H, s, N—H), 9.13 (1H, s, Boc-N—H), 7.46 (1H, d, J=1.9 Hz, Py-H), 7.21 (1H, d, J=1.7 Hz, Py-H), 7.06 (1H, d, J=1.7 Hz, Py-H), 6.91 (1H, s, Py-H), 6.90 (1H, s, Py-H), 6.85 (1H, s, Py-H), 3.84 (6H, s, N—CH$_3$), 3.81 (3H, s, N—CH$_3$), 3.74 (3H, s, O—CH$_3$), 1.46 (9H, s, Boc-H).

(iv) 4-({4-[(4-tert-butoxycarbonylamino-1-methyl-1H-pyrrole-2-carbonyl)-amino]-1-methyl-1H-pyrrole-2-carbonyl}-amino)-1-methyl-1H-pyrrole-2-carboxylic acid (6)

The Boc pyrrole trimer (5) (0.6 g, 1.2 mmol) was dissolved in MeOH (5 mL) and treated with NaOH solution (0.1 g in 5 mL H$_2$O). The reaction mixture was stirred overnight then heated at 60° C. for 2 hours. The MeOH was removed in vacuo and the aqueous fraction extracted with EtOAc (25 mL). The aqueous layer was adjusted to pH 2-3 with 1M HCl solution then extracted with EtOAc (3×30 mL). The combined organic layers were dried over MgSO$_4$ then concentrated in vacuo to give an orange solid. The solid was suspended in Et$_2$O (10 mL) and collected on a filter then dried in vacuo to give an orange solid 0.431 g (74%). $^1$H NMR d$_6$-DMSO δ 12.11 (1H, s, OH), 9.89 (1H, s, N—H), 9.86 (1H, s, N—H), 9.09 (1H, s, Boc-N—H), 7.43 (1H, d, J=1.9 Hz, Py-H), 7.22 (1H, d, J=1.7 Hz, Py-H), 7.06 (1H, d, J=1.7 Hz, Py-H), 6.90 (1H, s, Py-H), 6.86 (1H, d, J=1.9 Hz, Py-H), 6.84 (1H, s, Py-H), 3.85 (3H, s, N—CH$_3$), 3.83 (3H, s, N—CH$_3$), 3.82 (3H, s, N—CH$_3$), 1.46 (9H, s, Boc-H); $^{13}$C NMR d$_6$-DMSO δ 161.9, 158.4, 158.4, 152.8, 122.8, 122.7, 122.5, 122.4, 122.3, 120.2 (CH), 119.5, 118.4 (CH), 117.0 (CH), 108.4 (CH), 104.7 (CH), 103.8 (CH), 78.2, 36.1 (CH$_3$), 36.0 (CH$_3$), 28.1 ([CH$_3$]$_3$).

(v) Methyl 4-{[4-({4-[(4-tert-butoxycarbonylamino-1-methyl-1H-pyrrole-2-carbonyl)-amino]-1-methyl-1H-pyrrole-2-carbonyl}-amino)-1-methyl-1H-pyrrole-2-carbonyl]-amino}-1-methyl-1H-pyrrole-2-carboxylate (7)

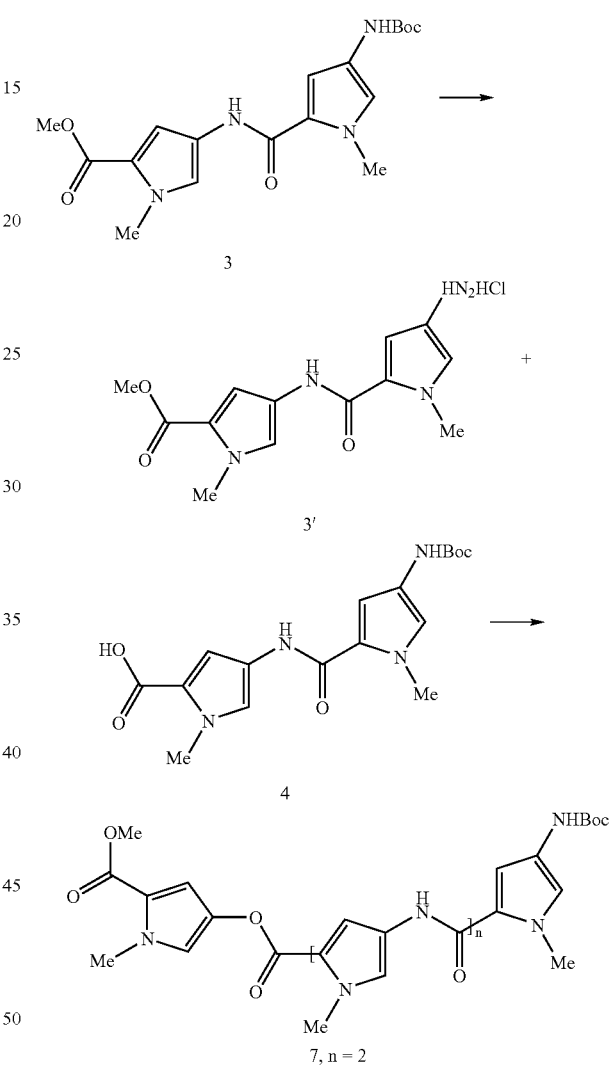

The Boc pyrrole dimer (3) (0.207 g, 0.54 mmol) in a dry round bottomed flask was treated with 4M HCl in dioxane (5 mL) with stirring. The reaction mixture was stirred for 30 minutes during which time a precipitate (3') formed. The solvent was removed and the residue dried in vacuo. The residue was dissolved in dry DMF (5 mL) and the Boc pyrrole dimer acid (4) (0.2 g, 0.55 mmol) was added followed by EDCI (0.159 g, 0.83 mmol, 1.5 equiv.) and DMAP (0.081 g, 0.66 mmol, 1.2 equiv.). The reaction mixture was stirred for 48 hours then diluted with EtOAc (50 mL) and washed with 10% HCl solution (3×30 mL) then saturated NaHCO$_3$ solution (3×30 mL). The organic layer was then dried over MgSO$_4$ and concentrated under vacuum to give an orange solid 0.310 g (90%). $^1$H NMR d$_6$-DMSO δ 9.93 (2H, s, N—H), 9.86 (1H, s, N—H), 9.08 (1H, s, Boc-N—H), 7.47 (1H, d, J=1.9 Hz, Py-H), 7.23 (1H, d, J=1.8 Hz, Py-H), 7.22 (1H, d, J=1.7 Hz, Py-H), 7.07 (1H, d, J=1.8 Hz, Py-H), 7.05 (1H, d, J=1.8 Hz, Py-H), 6.91 (1H, d, J=1.9 Hz, Py-H), 6.89 (1H, d, J=1.9 Hz, Py-H), 6.84 (1H, d, J=1.7 Hz, Py-H), 3.85 (3H, s, N—CH$_3$), 3.84 (6H, s, N—CH$_3$), 3.84 (3H, s, N—CH$_3$), 3.81 (3H, s, N—CH$_3$), 3.74 (3H, s, O—CH$_3$), 1.46 (9H, s, Boc-H).

(vi) Methyl 4-[(4-{[4-({4-[(4-tert-butoxycarbony-lamino-1-methyl-1H-pyrrole-2-carbonyl)-amino]-1-methyl-1H-pyrrole-2-carbonyl}-amino)-1-methyl-1H-pyrrole-2-carbonyl]-amino}-1-methyl-1H-pyrrole-2-carbonyl)-amino]-1-methyl-1H-pyrrole-2-carboxylate (8)

diluted with EtOAc (50 mL) and washed with 10% HCl solution (3×30 mL) then saturated NaHCO$_3$ (3×30 mL). The organic layer was dried over MgSO$_4$ then concentrated in vacuo to give an orange solid, 0.253 g (85%). $^1$H NMR d$_6$-DMSO δ 9.95 (1H, s, N—H), 9.93 (2H, s, N—H), 9.86 (1H, s, N—H), 9.08 (1H, s, N—H), 7.47 (1H, d, J=1.9 Hz, Py-H), 7.25 (1H, d, J=2.1 Hz, Py-H), 7.24 (1H, d, J=2.4 Hz, Py-H), 7.23 (1H, d, J=1.7 Hz, Py-H), 7.08 (1H, d, J=1.9 Hz, Py-H), 7.07 (1H, d, J=1.9 Hz, Py-H), 7.07 (1H, d, J=1.9 Hz, Py-H), 6.91 (1H, d, J=2.0 Hz, Py-H), 3.86 (3H, s, N—CH$_3$), 3.85 (3H, s, N—CH$_3$), 3.85 (3H, s, N—CH$_3$), 3.84 (3H, s, N—CH$_3$), 3.81 (3H, s, N—CH$_3$), 3.74 (3H, s, O—CH$_3$), 1.46 (9H, s, Boc-H).

(vii) Methyl 4-({4-[(4-{[4-({4-[(4-tert-butoxycarbo-nylamino-1-methyl-1H-pyrrole-2-carbonyl)-amino]-1-methyl-1H-pyrrole-2-carbonyl}-amino)-1-methyl-1H-pyrrole-2-carbonyl]-amino}-1-methyl-1H-pyrrole-2-carbonyl)-amino]-1-methyl-1H-pyrrole-2-carbonyl}-amino)-1-methyl-1H-pyrrole-2-carboxylate (9)

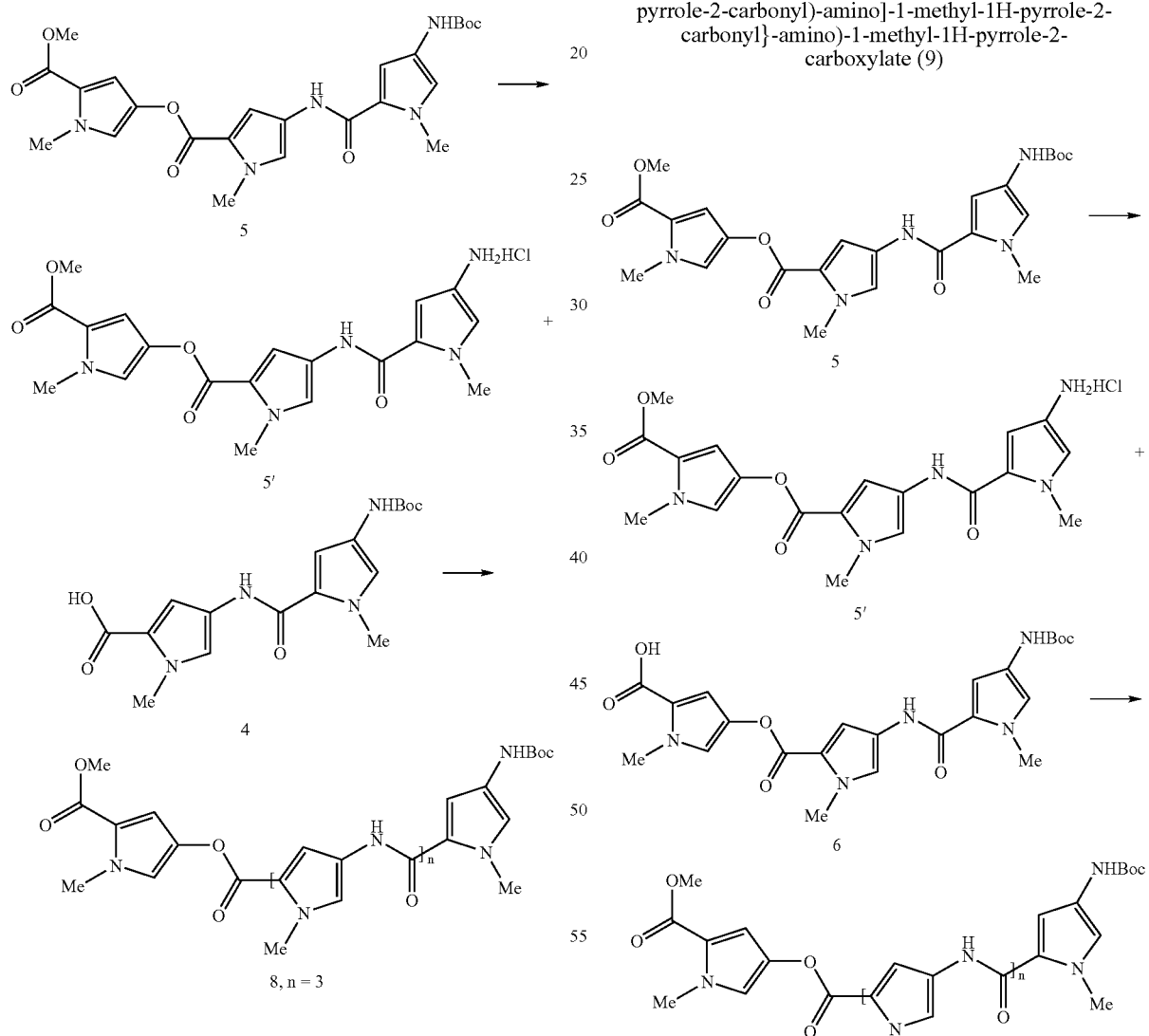

The Boc pyrrole trimer (5) (0.2 g, 0.40 mmol) in a dry round bottomed flask was treated with 4M HCl in dioxane (5 mL). The solution was stirred for 30 minutes during which time a precipitate (5') formed. The solvent was removed and the residue dried in vacuo. The residue was dissolved in dry DMF (2.5 mL) and the Boc pyrrole dimer acid [n] (0.144 g, 0.40 mmol, 1 equiv.) was added followed by EDCI (0.115 g, 0.60 g, 1.5 equiv.) and DMAP (0.058 g, 0.47 mmol, 1.2 equiv.). The reaction mixture was stirred for 48 hours then The Boc pyrrole trimer (5) (0.2 g, 0.40 mmol) in a dry round bottomed flask was treated with 4M HCl in dioxane (2.5 mL). The reaction mixture was stirred at room temperature for 30 minutes during which time a precipitate (5')

formed. The solvent was removed and the residue dried under vacuum. The residue was dissolved in dry DMF (2.5 mL) and the Boc pyrrole trimer acid (6) (0.194 g, 0.40 mmol, 1 equiv.) was added followed by EDCI (0.115 g, 0.6 mmol, 1.5 equiv.) and DMAP (0.058 g, 0.47 mmol, 1.2 equiv.). The reaction mixture was stirred for 48 hours then diluted with EtOAc (50 mL) and washed with 10% HCl solution (3×30 mL) and saturated NaHCO$_3$ solution (3×30 mL). The organic layer was dried over MgSO$_4$ then concentrated in vacuo to give an orange solid 0.185 g (54%). $^1$H NMR d$_6$-DMSO δ 9.95 (2H, s, N—H), 9.93 (2H, s, N—H), 9.86 (1H, s, N—H), 9.08 (1H, s, Boc-N—H), 7.47 (1H, d, J=1.8 Hz, Py-H), 7.25 (1H, d, J=2.2 Hz, Py-H), 7.24 (2H, d, J=2.0 Hz, Py-H), 7.22 (1H, d, J=1.6 Hz, Py-H), 7.07 (2H, d, J=1.6 Hz, Py-H), 7.07 (1H, d, J=2.0 Hz, Py-H), 6.91 (2H, d, J=1.9 Hz, Py-H), 6.89 (1H, s, Py-H), 6.84 (1H, s, Py-H), 3.86 (3H, s, N—CH$_3$), 3.86 (6H, s, N—CH$_3$), 3.85 (3H, s, N—CH$_3$), 3.84 (3H, s, N—CH$_3$), 3.81 (3H, s, N—CH$_3$), 3.74 (3H, s, O—CH$_3$), 1.46 (9H, s, Boc-H).

(viii) (11S,11aS)-8-(3-Carboxy-propoxy)-7-methoxy-11-(tetrahydro-pyran-2-yloxy)-1,2,3,10,11,11a-hexahydro-5H-pyrrolo[2,1-c][1,4]benzodiazepine-10-carboxylic acid allyl ester (19)

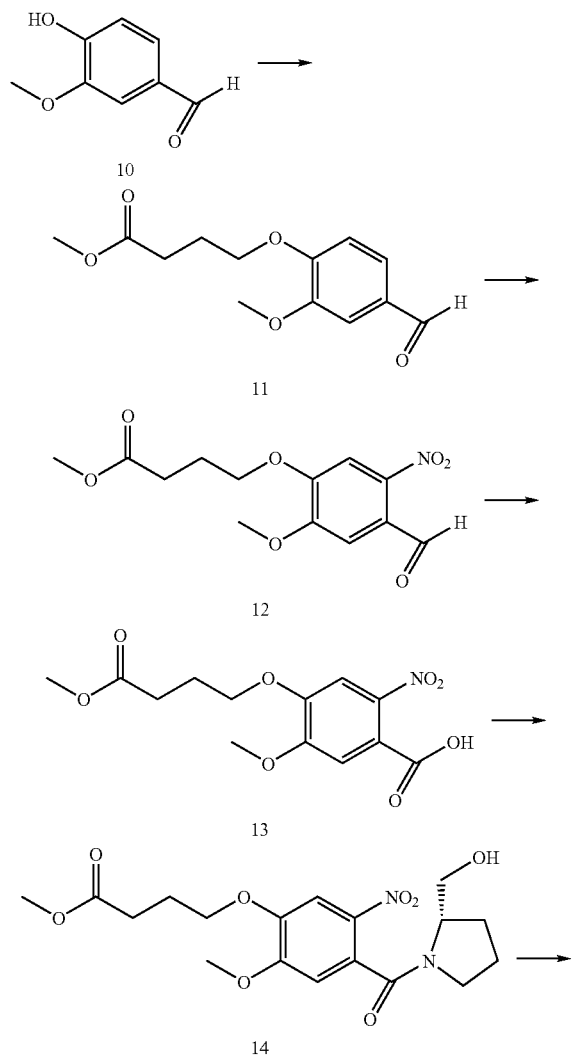

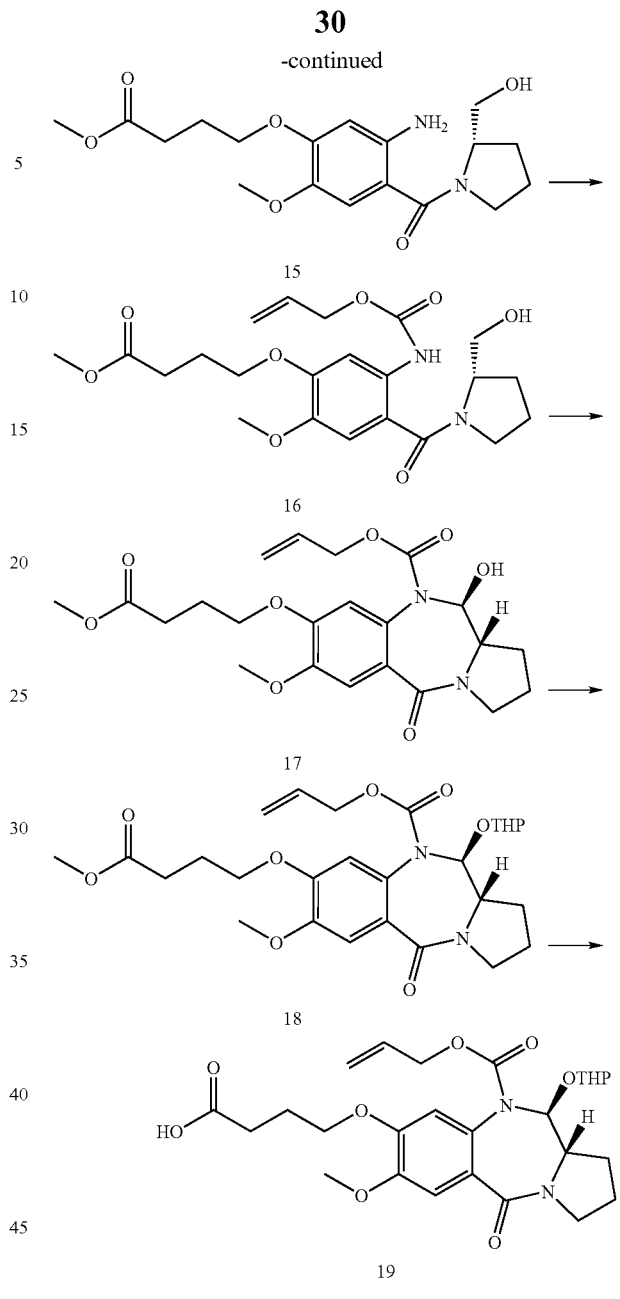

(a) 4-(4-Formyl-2-methoxy-phenoxy)-butyric acid methyl ester (11)

A slurry of vanillin 10 (40 g, 0.262 mol), methyl-4-bromobutyrate (50 g, 34.2 mL, 1.05 eq) and potassium carbonate (54 g, 1.5 eq) in DMF (200 mL) was stirred at room temperature overnight (16 hours). A large volume of water was added (1 L) whilst stirring. The white precipitate was filtered, washed with water and dried to yield 40, 60 g (85%). mp 73° C. $^1$H NMR (CDCl$_3$) δ 9.80 (1H, s) 7.43 (2H, m), 6.97 (1H, d, J=8.1 Hz), 4.16 (2H, t, J=6.28 Hz), 3.92 (3H, s), 3.70 (3H, s), 2.57 (2H, t, J=7.15 Hz), 2.20 (2H, p, J=6.71 Hz); $^{13}$C NMR (CDCl$_3$) δ 190.9, 173.4, 153.8, 149.9, 130.1, 126.8, 111.5, 109.2, 67.8, 56.0, 51.7, 30.3, 24.2; IR (golden gate) ν$_{max}$ 1728, 1678, 1582, 1508, 1469, 1426, 1398, 1262, 1174, 1133, 1015, 880, 809, 730 cm$^{-1}$; MS (ES$^+$) m/z (relative intensity) 253 ([M+H$^+$], 100).

(b) 4-(4-Formyl-2-methoxy-5-nitro-phenoxy)-butyric acid methyl ester (12)

A solution of the aldehyde 11 (50 g, 0.197 mol) in acetic anhydride (150 mL) was slowly added to a mixture of 70% nitric acid (900 mL) and acetic anhydride (200 mL) at 0° C. and was then left to stir for 2.5 hours at 0° C. The solution was then poured onto ice in a 5 L flask and the volume adjusted to 5 L with ice and water. The resulting light sensitive pale yellow precipitate was immediately filtered (the ester is slowly hydrolysed at room temperature in those conditions) and washed with cold water. The product 12 was used directly in the next step. TLC analysis (50/50 EtOAc/Pet Et) proved the product pure. $^1$H NMR (CDCl$_3$) δ 10.4 (2H, s), 7.61 (1H, s), 7.4 (1H, s), 4.21 (2H, t, J=6.2 Hz), 4.00 (3H, s), 3.71 (2H, s), 2.58 (2H, t, J=7.1 Hz), 2.23 (2H, p, J=6.3 Hz); $^{13}$C NMR (CDCl$_3$) δ 188.5, 172.8, 152.7, 151.0, 143.5, 124.7, 110.1, 108.2, 68.4, 56.4, 51.3, 29.7, 23.8; MS (ES$^+$) m/z (relative intensity) 298 ([M+H]$^+$, 100).

(c) 5-Methoxy-4-(3-methoxycarbonyl-propoxy)-2-nitro-benzoic acid (13)

The slightly wet nitroaldehyde 12 (80 g, wet) was dissolved in acetone (500 mL) in a 2 L flask fitted with a condenser and a mechanical stirrer. A hot solution of 10% potassium permanganate (50 g in 500 mL of water) was quickly added via a dropping funnel (in 5 to 10 minutes). Halfway through the addition the solution began to reflux violently and until the end of the addition. The solution was allowed to stir and cool down for an hour and was then filtered through celite and the brown residue was washed with 1 L of hot water. The filtrate was transferred in a large flask and a solution of sodium bisulfite (80 g in 500 mL 1N HCl) was added. The final volume was adjusted to 3 L by addition of water, and the pH was adjusted to 1 with conc. HCl. The product 42 precipitated and it was filtered and dried. 31 g (50% yield over 2 steps). The product was pure as proved by TLC (85/15/0.5 EtOAc/MeOH/Acetic acid). $^1$H NMR (CDCl$_3$) δ 7.33 (1H, s), 7.19 (1H, s), 4.09 (2H, t, J=5.72 Hz), 3.91 (3H, s), 3.64 (3H, s), 2.50 (2H, t, J=6.98 Hz), 2.14 (2H, p, J=6.33 Hz); $^{13}$C NMR (DMSO-d$_6$) δ 172.8, 166.0, 151.8, 149.1, 141.3, 121.2, 111.3, 107.8, 68.1, 56.4, 51.3, 29.7, 23.8; IR (golden gate) ν$_{max}$ 1736, 1701, 1602, 1535, 1415, 1275, 1220, 1054, 936, 879, 820, 655 cm$^{-1}$; MS (ES$^-$) m/z (relative intensity) 312.01 ([M−H]$^-$, 100).

(d) 4-[4-(2-Hydroxymethyl-pyrrolidine-1-carbonyl)-2-methoxy-5-nitro-phenoxy]-butyric acid methyl ester (14)

The methyl ester 13 (30 g, 95.8 mmol) was suspended in dry DCM (300 mL) with stirring in a round-bottomed flask equipped with a drying tube. Oxalyl chloride (13.4 g, 9.20 mL, 1.1 eq) was added followed by a few drops of DMF. The mixture was stirred overnight at room temperature. Triethylamine (21.3 g, 29.3 mL, 2.2 eq), +(S)-pyrrolidine methanol (9.68 g, 9.44 mL, 1.1 eq) were dissolved in dry DCM (150 mL) under nitrogen. The solution was cooled below −30° C. The acid chloride solution was added dropwise over 6 h maintaining the temperature below −30° C. It was then left to stir overnight at room temperature. The resulting solution was extracted with 1N HCl (2×200 mL), twice with water, once with brine. It was dried with magnesium sulfate and concentrated in vacuo to give a yellow/brown oil 14 which solidified on standing. (quantitative yield). It was used in the next step without further purification. $^1$H NMR (CDCl$_3$) δ 7.70 (1H, s), 6.80 (1H, s), 4.40 (1H, m), 4.16 (2H, t, J=6.2 Hz), 3.97 (3H, s), 3.97-3.70 (2H, m), 3.71 (3H, s), 3.17 (2H, t, J=6.7 Hz), 2.57 (2H, t, J=7.1 Hz), 2.20 (2H, p, J=6.8 Hz), 1.90-1.70 (2H, m); $^{13}$C NMR (CDCl$_3$) δ 173.2, 154.8, 148.4, 109.2, 108.4, 68.4, 66.1, 61.5, 56.7, 51.7, 49.5, 30.3, 28.4, 24.4, 24.2; IR (golden gate) ν$_{max}$ 3400, 2953, 1734, 1618, 1517, 1432, 1327, 1271, 1219, 1170, 1051, 995, 647 cm$^{-1}$; MS (ES$^+$) m/z (relative intensity) 397.07 ([M+H]$^+$, 100); [α]$^{24}_D$=−84° (c=1, CHCl$_3$).

(e) 4-[5-Amino-4-(2-hydroxymethyl-pyrrolidine-1-carbonyl)-2-methoxy-phenoxy]-butyric acid methyl ester (15)

The nitro ester 14 (38.4 g, 97 mmol) was dissolved in ethanol (2 batches of 19.2 g in 200 mL ethanol per 500 mL hydrogenation flask). 10% Pd/C was added as a slurry in ethanol (1 g per batch) and the mixture was hydrogenated in a Parr hydrogenation apparatus at 40 psi until no further hydrogen uptake was observed. Reaction completion was confirmed by TLC analysis (EtOAc) and the mixture was filtered through celite. The solvent was removed in vacuo and the amine 15 was used directly in the next step. (35.4 g, quantitative yield).

(f) 4-[5-Allyloxycarbonylamino-4-(2-hydroxymethyl-pyrrolidine-1-carbonyl)-2-methoxy-phenoxy]-butyric acid methyl ester (16)

A batch of the amine 15 (22.5 g, 61.5 mmol) was dissolved in anhydrous DCM (300 mL) in the presence of anhydrous pyridine (10.9 mL, 134 mmol) at 0° C. Allyl chloroformate (7.17 mL, 67.5 mmol) diluted in anhydrous DCM (200 mL) was added dropwise at 0° C. The resulting solution was allowed to stir overnight at room temperature. It was then washed with cold 1N aqueous HCl (200 ml), water (200 mL), saturated aqueous NaHCO$_3$ (200 mL), and brine (200 mL). The solution was then dried (MgSO$_4$), and the solvent was removed in vacuo to provide 16, slightly contaminated by the product of diacylation (27 g, quantitative yield). A sample was columned (EtOAc/Hexane) to provide the analytical data. $^1$H NMR (CDCl$_3$) δ 8.78 (1H, bs), 7.75 (1H, s), 6.82 (1H, s), 5.97 (1H, m), 5.38-5.34 (1H, dd, J=1.5, 17.2 Hz), 5.27-5.24 (1H, dd, J=1.3, 10.4 Hz, 1H), 4.63 (2H, m), 4.40 (2H, bs), 4.11 (2H, t, J=6.3 Hz), 3.82 (3H, s), 3.69 (4H, m), 3.61-3.49 (2H, m), 2.54 (2H, t, J=7.4 Hz), 2.18 (2H, p, J=6.7 Hz), 1.92-1.70 (4H, m); $^{13}$C NMR (CDCl$_3$) δ 173.4, 170.9, 153.6, 150.5, 144.0, 132.5, 132.0, 118.1, 115.4, 111.6, 105.6, 67.7, 66.6, 65.8, 61.1, 60.4, 56.6, 51.7, 30.5, 28.3, 25.1, 24.3; MS (FAB$^+$) m/z 50 (451, M+H); IR (golden gate) ν$_{max}$ 2949, 2359, 1728, 1596, 1521, 1433, 1202, 1173, 1119, 998, 844, 652 cm$^{-1}$; [α]$^{26}_D$=−67° (c=0.45, CHCl$_3$).

(g) 11-Hydroxy-7-methoxy-8-(3-methoxycarbonyl-propoxy)-5-oxo-2,3,11,11a-tetrahydro-1H,5H-benzo[e]pyrrolo[1,2-a][1,4]diazepine-10-carboxylic acid allyl ester (17)

Oxalyl chloride (17.87 g, 12.28 mL, 1.8 eq) in dry DCM (200 mL) was cooled to −40° C. (acetonitrile/liquid nitrogen cooling bath). A solution of dry DMSO (16.23 g, 16.07 mL, 3.6 eq) in dry DCM (200 mL) was added dropwise over 2 hours maintaining the temperature below 37° C. A white suspension formed and eventually redissolved. The crude Alloc protected amine 16 (26 g, 57.7 mmol) in dry DCM (450 mL) was added dropwise over 3 hours maintaining the temperature below −37° C. The mixture was stirred at −40° C. for a further hour. A solution of DIPEA (32.1 g, 43.2 mL, 4.3 eq) in dry DCM (100 mL) was added dropwise over 1 hour and the reaction was allowed to come back to room temperature. The reaction mixture was extracted with a concentrated solution of citric acid in water. (pH 2 to 3 after extraction). It was then washed with water (2×400 mL) and brine (300 mL), dried (magnesium sulfate) and the solvent removed in vacuo to yield a paste which was purified by column chromatography. (70/30 EtOAc/Pet Ether) to yield 46, 17 g (62%); $^1$H NMR (CDCl$_3$) δ 7.23 (1H, s), 6.69 (1H, s), 5.80 (1H, m), 5.63 (1H, m), 5.15 (2H, d, J=12.9 Hz), 4.69-4.43 (2H, m), 4.13 (2H, m), 3.90 (4H, m), 3.68 (4H, m), 3.58-3.45 (2H, m), 2.53 (2H, t, J=7.2 Hz), 2.18-1.94 (6H, m); $^{13}$C NMR (CDCl$_3$) δ 173.4, 167.0, 156.0, 149.9, 148.7, 131.8, 128.3, 125.9, 118.1, 113.9, 110.7, 86.0, 67.9, 66.8, 60.4, 59.9, 56.1, 51.7, 46.4, 30.3, 28.7, 24.2, 23.1, 21.1; MS (ES$^+$) m/z 100 (449.1, M+H); IR (golden gate) $v_{max}$ 2951, 1704, 1604, 1516, 1458, 1434, 1313, 1272, 1202, 1134, 1103, 1041, 1013, 647 cm$^{-1}$; $[\alpha]^{26}{}_D$=+122° (c=0.2, CHCl$_3$).

(h) (11aS)-7-Methoxy-8-(3-methoxycarbonyl-propoxy)-5-oxo-11-(tetrahydropyran-2-yloxy)-2,3,11,11a-tetrahydro-1H,5H-pyrrolo[2,1-c][1,4]benzodiazepine-10-carboxylic acid allyl ester (18)

Dihydropyran (4.22 mL, 46.2 mmol) was dissolved in EtOAc (30 mL). This solution was stirred 10 minutes in the presence of para-toluenesulphonic acid (catalytic quantity, 20 mg). 17 (2.0 g, 4.62 mmol) was then added in one portion to this solution and allowed to stir for 2 hours. The solution was diluted with EtOAc (70 mL) and washed with saturated aqueous NaHCO$_3$ (50 mL) followed by brine (50 mL). The organic layer was dried (MgSO$_4$), and the solvent removed under vacuum. The oily residue was dried under vacuum to remove any remaining DHP. It was proved pure by TLC (EtOAc) and 18, was retrieved in quantitative yield, 2.38 g (100%). It was used directly in the next step. $^1$H NMR (CDCl$_3$) as a mixture of 4/5 of diastereoisomers: δ 7.24-7.21 (2H, s×2), 6.88-6.60 (2H, s×2), 5.89-5.73 (4H, m), 5.15-5.04 (6H, m), 4.96-4.81 (2H, m), 4.68-4.35 (4H, m), 4.12-3.98 (4H, m), 3.98-3.83 (8H, m), 3.74-3.63 (8H, m), 3.60-3.40 (8H, m), 2.56-2.50 (4H, m), 2.23-1.93 (12H, m), 1.92-1.68 (10H, m), 1.66-1.48 (20H, m); $^{13}$C NMR (CDCl$_3$) δ 173.4, 167.2, 149.1, 132.0, 114.5, 100.0, 98.4, 94.6, 91.7, 68.0, 67.7, 66.3, 63.9, 63.6, 63.3, 62.9, 56.1, 51.6, 51.5, 46.3, 46.3, 31.1, 30.9, 30.7, 30.4, 30.2, 29.0, 25.4, 25.3, 25.2, 24.2, 20.0, 19.8, 19.7; MS (ES$^+$) m/z (relative intensity) 533.2 ([M+H]$^+$, 100).

(i) (11aS)-8-(3-Carboxy-propoxy)-7-methoxy-5-oxo-11-(tetrahydropyran-2-yloxy)-2,3,11,11a-tetrahydro-1H,5H-pyrrolo[2,1-c][1,4]benzodiazepine-10-carboxylic acid allyl ester (19)

The methyl ester 18 (2.2 g, 4.26 mmol) was dissolved in MeOH (30 mL). Sodium hydroxide (340 mg, 8.5 mmol) was dissolved in water (7 mL) and added to the ester solution. The reaction mixture was stirred at 70° C. for 15 min. The methanol was then removed under vacuum and water (20 mL) was added. The aqueous solution was allowed to return to room temperature and a 5% aqueous citric acid solution was added to adjust the pH to <4. The precipitate was extracted with EtOAc (100 mL). The organic layer was washed with brine (30 mL) and dried over MgSO$_4$. The solvent was removed under vacuum, then diethylether (50 mL) was added to the residue and removed under vacuum, then dried under vacuum to yield the pure 19 as white foam 2.10 g (98%). $^1$H NMR (d$_6$-DMSO) as a mixture of 4/5 of diastereoisomers δ 7.10 (2H, s×2), 6.90-6.84 (2H, s×2), 5.84-5.68 (4H, m), 5.45-4.91 (6H, m), 4.72-4.30 (4H, m), 4.09-3.93 (4H, m), 3.91-3.75 (8H, m), 3.60-3.44 (4H, m), 3.44-3.22 (8H, m), 2.46-2.33 (4H, m), 2.20-1.76 (14H, m), 1.76-1.31 (12H, m). $^{13}$C NMR (d$_6$-DMSO) δ 173.9, 173.9, 171.9, 166.1, 166.0, 149.6, 148.4, 148.3, 132.6, 116.5, 114.4, 110.5, 110.3, 99.2, 67.5, 67.4, 65.6, 65.5, 62.8, 59.4, 55.7, 45.9, 30.5, 30.2, 29.8, 29.7, 28.4, 28.3, 24.9, 24.8, 23.9, 23.8, 22.9, 22.7; MS (ES$^+$) m/z (relative intensity) 519.2 ([M+H]$^+$, 100). This compound was proved optically pure at C11a by reesterification (EDCI, HOBt, then MeOH), THP removal (AcOH/THF/H$_2$O) and chiral HPLC, as in Tercel et al., J. Med. Chem., 2003, 46, 2132-2151).

Example 1a (11aS) Methyl 4-[4-(7-methoxy-5-oxo-2,3,5,11a-tetrahydro-5H-pyrrolo[2,1-c][1,4]benzodiazepine-8-yloxy)-butyrylamino]-1-methyl-1H-pyrrole-2-carboxylate (21, GWL77)

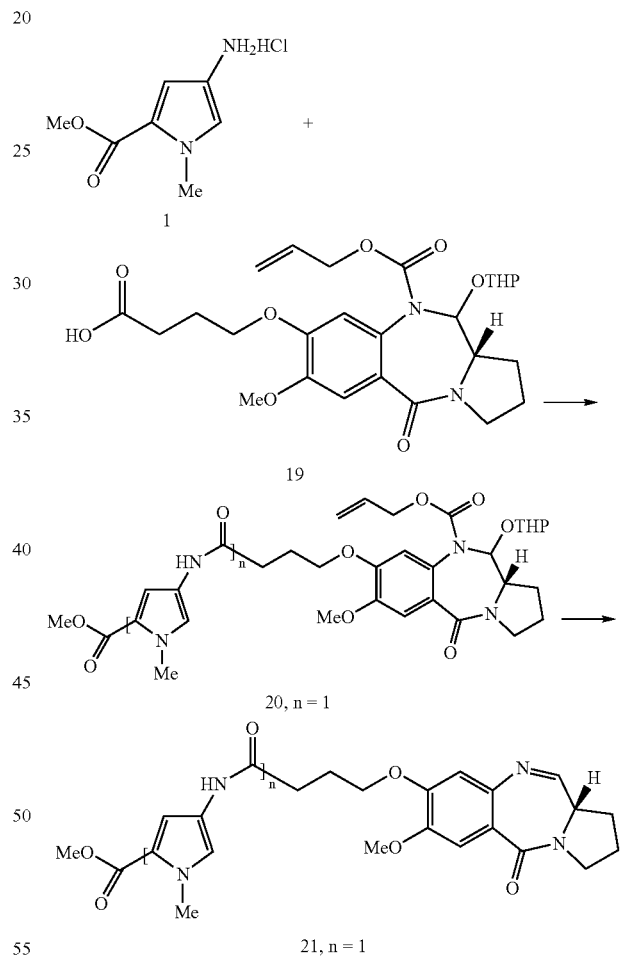

(i) A solution of pyrrole methyl ester (1) (0.055 g, 0.29 mmol) and AllocTHPPBD acid (19) (0.150 g, 0.29 mmol, 1 equiv.) dissolved in dry CH$_2$Cl$_2$ (2 mL) was treated with EDCI (0.111 g, 0.58 mmol, 2 equiv.) and DMAP (0.088 g, 0.72 mmol, 2.5 equiv.). The reaction mixture was stirred for 24 hours then the solvent was removed in vacuo and the residue diluted with EtOAc (25 mL) and washed with 1M HCl solution (3×10 mL) then saturated NaHCO$_3$ solution (3×10 mL). The organic fraction was dried over MgSO$_4$ and concentrated in vacuo, to give an off white foamy solid (20), 0.167 g (88%). Mixture of diastereomers $^1$H-NMR (400

MHz) δ 9.09 (1H, s, N—H), 7.39 (1H, d, J=2.0 Hz, Py-H), 7.14 (1H, s, H-6), 7.12 (1H, s, H-6), 6.96 (1H, s, H-9), 6.76 (1H, d, J=2.0 Hz, Py-H), 5.86-5.75 (3H, m, H-11, Alloc-H), 5.13 (1H, s, pyran H-2), 5.03 (1H, m, pyran H-2), 4.51 (2H, m, Alloc-H), 4.06-3.88 (3H, m, sidechain H-1, pyran H-6), 3.87 (3H, s, O/N—CH$_3$), 3.87 (3H, s, O/N—CH$_3$), 3.86 (3H, s, O/N—CH$_3$), 3.74 (3H, s, OCH$_3$), 3.74 (3H, s, OCH$_3$), 3.53-3.44 (3H, m, H-11a, H-3), 2.50 (2H, m, sidechain H-3), 2.13-1.98 (6H, m, H-1, 2, sidechain H-2), 1.70 (2H, m, pyran H-3), 1.49 (4H, m, pyran H-4, 5)

(ii) A solution of AllocTHPPBD conjugate (20) (0.157 g, 0.24 mmol) dissolved in dry CH$_2$Cl$_2$ (2 mL) under a nitrogen atmosphere was treated with pyrrolidine (22 μL, 0.26 mmol, 1.1 equiv.) and then palladium tetrakis[triphenylphosphine] (0.014 g, 0.012 mmol, 0.05 equiv.). The reaction mixture was stirred at room temperature for 2 hours and the product purified directly by column chromatography (silica gel, eluted with CHCl$_3$ 96%, MeOH 4%) to give the product as a glassy solid, 0.093 g (83%). $[\alpha]^{27.2}_D$+351°; $^1$H-NMR (400 MHz) δ 9.94 (1H, s, N—H), 7.83 (1H, d, J=4.4 Hz, H-11), 7.39 (1H, d, J=2.0 Hz, Py-H), 7.39 (1H, s, H-6), 6.88 (1H, s, H-9), 6.76 (1H, d, J=2.0 Hz, Py-H), 4.17 (1H, m, H-1 sidechain) 4.08 (1H, m, H-1 sidechain), 3.87 (3H, s, O/N—CH$_3$), 3.86 (3H, s, O/N—CH$_3$), 3.77 (3H, s, OCH$_3$), 3.72 (1H, m, H-11a), 3.65 (2H, m, sidechain H-3), 3.44 (2H, m, H-3), 2.47 (2H, m, sidechain H-1), 2.34-2.29 (2H, m, H-1), 2.09 (2H, m, sidechain H-2), 2.00 (2H, m, H-2); $^{13}$C-NMR (100 MHz) δ 168.8, 164.2 (C-11), 163.3, 160.7, 150.2, 146.9, 122.7, 120.4 (C-9), 119.8, 118.5, 111.2 (py-CH), 110.1 (C-6), 107.6 (py-CH), 67.7 (C-1 sidechain), 55.6 (C-11a), 53.4 (CH$_3$), 50.9 (CH$_3$), 46.3 (C-3), 36.1 (CH$_3$), 31.9 (C-3 sidechain), 28.8 (C-1), 24.6 (C-2 sidechain), 23.6 (C-2); IR (solid) $v_{max}$ 3296, 2937, 1702, 1596, 1580, 1451, 1255, 1196, 1097, 782 cm$^{-1}$; Acc. Mass C$_{24}$H$_{28}$N$_4$O$_6$ calc. 469.2082 found 469.2085

Example 1b (11aS) Methyl 4-({4-[4-(7-Methoxy-6-oxo-2,3,5,11a-tetrahydro-5H-pyrrolo[2,1-c][1,4]benzodiazepine-8-yloxy)-butyrylamino]-1-methyl-1H-pyrrole-2-carbonyl}-amino)-1-methyl-1H-pyrrole-2-carboxylate (23, GWL78)

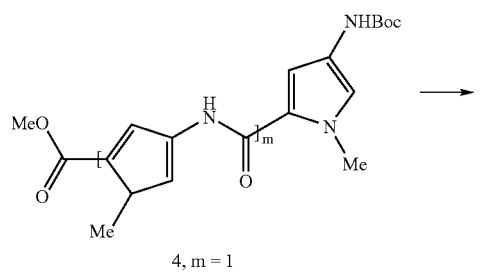

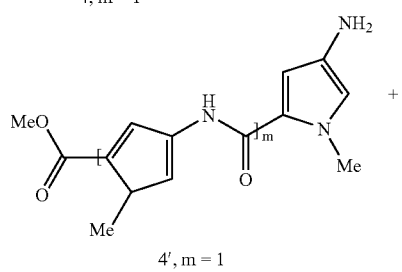

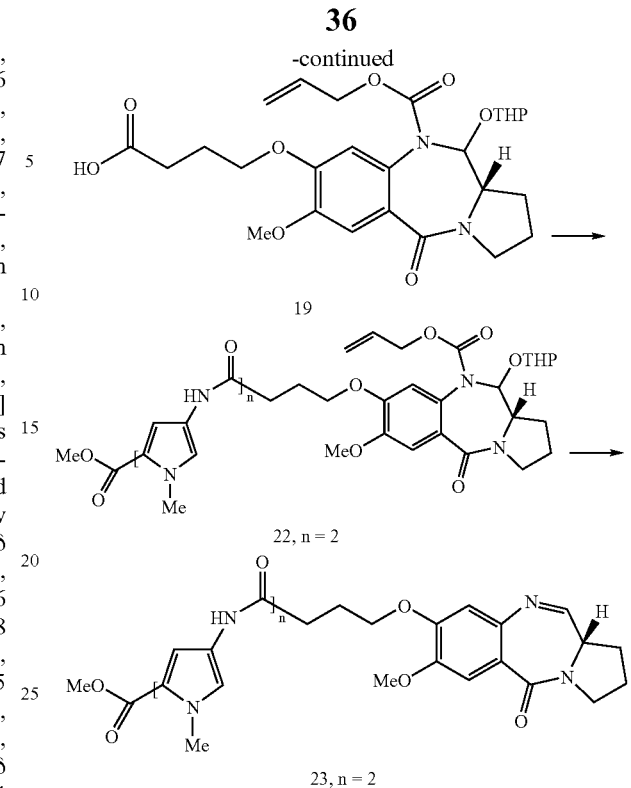

(i) The Boc pyrrole dimer (4) (0.109 g, 0.29 mmol) was treated with 4M HCl in dioxane (2 mL). The reaction mixture was stirred at room temperature for 30 minutes during which time a precipitate (4') formed. The solvent was removed and the residue dried in vacuo. The residue was dissolved in dry CH$_2$Cl$_2$ and AllocTHPPBD acid (12) (0.150 g, 0.29 mmol, 1 equiv.) was added followed by EDCI (0.111 g, 0.58 mmol, 2 equiv.) and DMAP (0.088 g, 0.72 mmol, 2.5 equiv.). The reaction mixture was stirred for 24 hours then the solvent was removed in vacuo and the residue diluted with EtOAc (25 mL) and washed with 1M HCl solution (3×10 mL) then saturated NaHCO$_3$ solution (3×10 mL). The organic fraction was dried over MgSO$_4$ and concentrated in vacuo, to give a solid, 0.232 g which was purified by column chromatography (silica gel, eluted with CHCl$_3$ 97%, MeOH 3%) to give a foam (22) 0.115 g, (51%). Mixture of diastereomers $^1$H-NMR (400 MHz) δ 9.20 (2H, s, N—H), 7.33 (1H, d, J=1.8 Hz), 7.17 (1H, m, Py-H), 7.14 (1H, s, H-6), 7.13 (1H, s, H-6), 6.94 (1H, s, H-9), 6.91 (1H, m, Py-H), 6.90 (1H, m, Py-H), 6.80 (1H, m, Py-H), 5.86-5.75 (3H, m, H-11, Alloc-H), 5.04 (1H, s, pyran H-2), 4.07-3.87 (4H, s, sidechain H-3, pyran H-6), 3.86 (3H, s, O/N—CH$_3$), 3.86 (3H, s, O/N—CH$_3$), 3.85 (3H, s, O/N—CH$_3$), 3.77 (1H, s, OCH$_3$), 3.59-3.46 (3H, m, H-11a, H-3), 2.51 (2H, m, sidechain H-3), 2.15-2.02 (6H, m, H-1, 2, sidechain H-2), 1.71 (2H, m, pyran H-3), 1.50 (4H, m, pyran H-4, 5)

(ii) A solution of AllocTHPPBD conjugate (22) (0.093 g, 0.12 mmol) dissolved in dry CH$_2$Cl$_2$ (2 mL) under a nitrogen atmosphere was treated with pyrrolidine (1 μL, 0.13 mmol, 1.1 equiv.) and then palladium tetrakis[triphenylphosphine] (0.007 g, 0.006 mmol, 0.05 equiv.). The reaction mixture was stirred at room temperature for 2 hours and the product purified directly by column chromatography (silica gel, eluted with CHCl$_3$ 96%, MeOH 4%) to give the product as a glassy solid, 0.067 g (95%). $[\alpha]^{27.1}_D$+348°; $^1$H-NMR (400 MHz) δ 9.88 (1H, s, N—H), 7.78 (1H, d, J=4.3 Hz, H-11), 7.45 (1H, d, J=1.7 Hz, Py-H), 7.34 (1H, s, H-6), 7.16 (1H, d, J=1.6 Hz, Py-H), 6.90 (1H, d, J=1.9 Hz, Py-H), 6.88 (1H, d, J=1.8 Hz, Py-H), 6.83 (1H, s, H-9), 4.10 (1H, m, sidechain H-1), 3.97 (1H, m, sidechain H-1), 3.84 (6H, s, O/N—CH$_3$), 3.83 (3H, s, O/N—CH$_3$), 3.74 (3H, s, OCH$_3$), 3.68 (1H, m, H-11a), 3.60 (1H, m, H-3), 3.40 (1H, m, H-3), 2.44 (1H, m, sidechain H-3), 2.23 (2H, m, H-1), 2.09 (2H, m, sidechain H-2), 1.93 (2H, m, H-2); $^{13}$C-NMR (100 MHz) δ 168.8, 164.2 (C-11), 163.3, 160.8, 158.4, 150.2, 146.9, 140.6, 122.9, 122.5, 122.1, 120.7 (C-9), 119.8, 118.5 (py-CH), 118.3, 111.3 (py-CH), 110.1 (C-6), 108.3 (py-CH), 104.0 (py-CH), 67.8 (C-1 sidechain), 55.6 (C-11a), 53.4 (CH$_3$), 50.9 (CH$_3$), 46.4 (C-3), 36.1 (CH$_3$), 36.0 (CH$_3$), 31.9 (C-3 sidechain), 28.8 (C-1), 24.7 (C-2 sidechain), 23.6 (C-2); IR (solid) ν$_{max}$ 3300, 2947, 1703, 1596, 1582, 1448, 1435, 1252, 1197, 1100, 781 cm$^{-1}$; Acc. Mass C$_{30}$H$_{34}$N$_6$O$_7$ calc. 591.2562 found 591.2535

Example 1c (11aS) Methyl 4-{[4-({4-[4-(7-Methoxy-6-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-1-methyl-1H-pyrrole-2-carbonyl]-amino}-1-methyl-1H-pyrrole-2-carboxylate (25, GWL79)

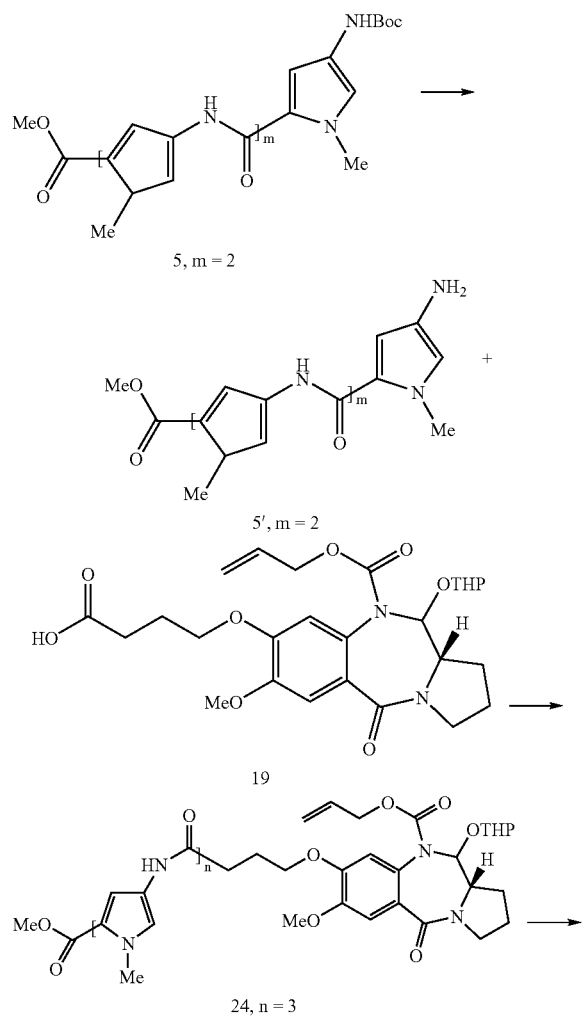

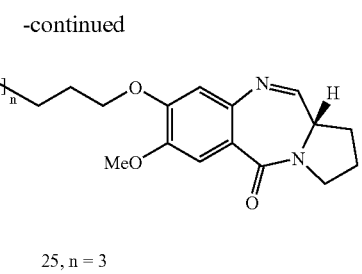

25, n = 3

(i) A solution of Boc pyrrole trimer (5) (0.144 g, 0.29 mmol) was treated with 4M HCl in dioxane (2 mL). The reaction mixture was stirred at room temperature for 30 minutes during which time a precipitate (5') formed. The solvent was removed and the residue dried in vacuo. The residue was dissolved in dry CH$_2$Cl$_2$ and AllocTHPPBD acid (19) (0.150 g, 0.29 mmol, 1 equiv.) was added followed by EDCI (0.11 g, 0.58 mmol, 2 equiv.) and DMAP (0.088 g, 0.72 mmol, 2.5 equiv.). The reaction mixture was stirred for 24 hours then the solvent was removed in vacuo and the residue diluted with EtOAc (25 mL) and washed with 1M HCl solution (3×10 mL) then saturated NaHCO$_3$ solution (3×10 mL). The organic fraction was dried over MgSO$_4$ and concentrated in vacuo, to give an off white foamy solid (24), 0.153 g (59%). Mixture of diastereomers $^1$H-NMR (400 MHz) □ 9.28 (1H, s, N—H), 9.19 (1H, s, N—H), 9.02 (1H, s, N—H), 7.50 (1H, d, J=1.7 Hz, Py-H), 7.23 (1H, d, J=1.7 Hz, Py-H), 7.16 (1H, d, J=1.7 Hz, Py-H), 7.15 (1H, s, H-6), 7.13 (1H, s, H-6), 6.99 (1H, d, J=1.7 Hz, Py-H), 6.92 (1H, d, J=1.9 Hz, Py-H), 6.91 (1H, s, H-9), 6.81 (1H, s, Py-H), 5.89-5.76 (3H, m, H-11, Alloc-H), 5.13 (1H, m, pyran H-2), 4.53 (2H, m, Alloc-H), 4.11 (3H, m, sidechain H-1, pyran H-6), 3.94 (3H, s, O/N—CH$_3$), 3.93 (3H, s, O/N—CH$_3$), 3.91 (3H, s, O/N—CH$_3$), 3.87 (3H, s, O/N—CH$_3$), 3.76 (3H, s, OCH$_3$), 3.57-3.45 (3H, m, H-3, H-11a), 2.49 (2H, m, sidechain H-3), 2.12-1.98 (6H, m, H-1, 2, sidechain H-2), 1.69 (2H, m, pyran H-3), 1.49 (4H, m, pyran H-4, 5).

(ii) A solution of AllocTHPPBD conjugate (24) (0.140 g, 0.16 mmol) dissolved in dry CH$_2$Cl$_2$ (2 mL) under a nitrogen atmosphere was treated with pyrrolidine (15 µL, 0.17 mmol, 1.1 equiv.) and then palladium tetrakis[triphenylphosphine] (0.009 g, 0.008 mmol, 0.05 equiv.). The reaction mixture was stirred at room temperature for 2 hours and the product purified directly by column chromatography (silica gel, eluted with CHCl$_3$ 96%, MeOH 4%) to give the product as a glassy solid, 0.076 g (68%). [α]$^{27.1}_D$+185°; $^1$H-NMR (400 MHz) δ 9.92 (1H, s, N—H), 9.90 (1H, s, N—H), 9.88 (1H, s, N—H), 7.78 (1H, d, J=4.4 Hz, H-11), 7.47 (1H, d, J=1.9 Hz, Py-H), 7.34 (1H, s, H-6), 7.24 (1H, d, J=1.7 Hz, Py-H), 7.17 (1H, d, J=1.7 Hz, Py-H), 7.06 (1H, d, J=1.8 Hz, Py-H), 6.91 (1H, d, J=1.9 Hz, Py-H), 6.89 (1H, d, J=1.8 Hz, Py-H), 6.83 (1H, s, H-9), 4.14 (1H, m, sidechain H-1), 4.05 (1H, m, sidechain H-1), 3.85 (3H, s, O/N—CH$_3$), 3.84 (3H, s, O/N—CH$_3$), 3.84 (3H, s, O/N—CH$_3$), 3.83 (3H, s, O/N—CH$_3$), 3.74 (3H, s, OCH$_3$), 3.67 (1H, m, H-11a), 3.61 (1H, m, H-3), 3.40 (1H, m, H-3), 2.45 (2H, m, sidechain H-3), 2.30-2.23 (2H, m, H-1), 2.05 (2H, m, sidechain H-2), 1.95 (2H, m, H-2); $^{13}$C-NMR (100 MHz) δ 168.8, 164.2 (C-11), 163.3, 160.8, 158.5, 158.1, 150.2, 146.9, 140.6, 123.0, 122.7, 122.5, 122.2, 122.0, 120.7 (C-9), 119.8, 118.6 (py-CH), 118.5 (py-CH), 118.2, 111.3 (py-CH), 110.1 (C-6), 108.3 (py-H), 104.0 (py-H), 104.0 (py-H), 55.6 (C-11a), 53.4 (CH$_3$), 50.9 (CH$_3$), 46.4 (C-3), 36.2 (CH$_3$), 36.1 (CH$_3$), 36.0 (CH$_3$), 31.9 (C-3 sidechain), 28.8 (C-1), 24.8 (C-2 sidechain), 23.7 (C-2); IR (solid) ν$_{max}$ 3300, 2946, 1702, 1594, 1579, 1433, 1249, 1199, 1104, 774;

The racaemic version of this compound was made as follows: The BocPBD conjugate [n] (0.100 g, 0.12 mmol) dissolved in CH$_2$Cl$_2$ (2.5 mL) was treated with a mixture of TFA (2.375 mL) and H$_2$O (0.125 mL). The reaction mixture was stirred for 1 hour at room temperature then poured into a flask containing ice (~20 g) and CH$_2$Cl$_2$ (~20 mL). The mixture was adjusted to pH~8 by careful addition of saturated NaHCO$_3$ solution (~50 mL). The layers were separated and the aqueous phase extracted with CH$_2$Cl$_2$ (2×20 mL). The combined organic layers were dried over MgSO$_4$ and concentrated in vacuo to give an off white foam, 0.083 g (97%).

Example 1d (11aS) Methyl 4-[(4-{[4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-1-methyl-1H-pyrrole-2-carbonyl]-amino}-1-methyl-1H-pyrrole-2-carbonyl)-amino]-1-methyl-1H-pyrrole-2-carboxylate (27, GWL80)

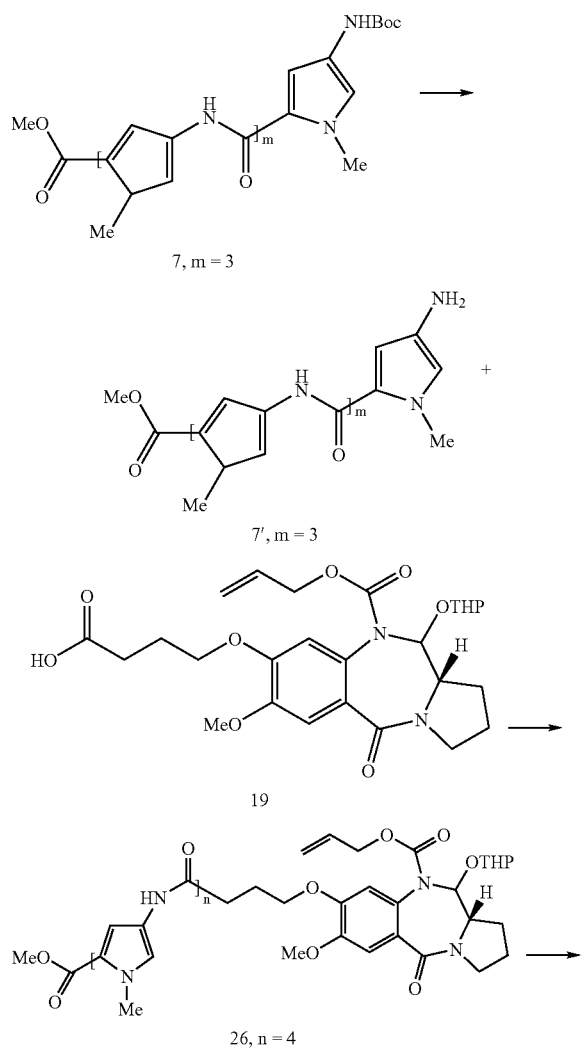

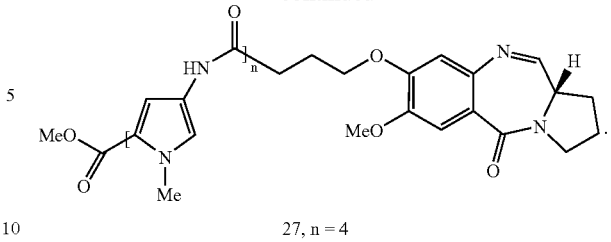

27, n = 4

(i) A solution of Boc pyrrole tertamer (7) (0.180 g, 0.29 mmol) was treated with 4M HCl in dioxane (2 mL). The reaction mixture was stirred at room temperature for 30 minutes during which time a precipitate (7') formed. The solvent was removed and the residue dried in vacuo. The residue was dissolved in dry CH$_2$Cl$_2$ and AllocTHPPBD acid (19) (0.150 g, 0.29 mmol, 1 equiv.) was added followed by EDCI (0.111 g, 0.58 mmol, 2 equiv.) and DMAP (0.088 g, 0.72 mmol, 2.5 equiv.). The reaction mixture was stirred for 24 hours then the solvent was removed in vacuo and the residue diluted with EtOAc (25 mL) and washed with 1M HCl solution (3×10 mL) then saturated NaHCO$_3$ solution (3×10 mL). The organic fraction was dried over MgSO$_4$ and concentrated in vacuo, to give an off white foamy solid (26), 0.068 g (23%). Mixture of diastereomers $^1$H-NMR (400 MHz) δ 9.28 (1H, s, N—H), 9.25 (1H, s, N—H), 9.18 (1H, s, N—H), 9.03 (1H, s, N—H), 7.50 (1H, d, J=1.9 Hz, Py-H), 7.23 (1H, d, J=1.4 Hz, Py-H), 7.15 (1H, s, H-6), 7.14 (1H, s, H-6), 6.99 (1H, J=2.0 Hz, Py-H), 6.96 (1H, s, H-9), 6.93 (1H, d, J=1.9 Hz, Py-H), 6.90 (1H, s, Py-H), 6.83 (1H, s, Py-H), 6.81 (1H, s, Py-H), 5.87-5.77 (1H, m, H-11, Alloc-H), 5.09 (1H, m, pyran H-2), 4.62-4.42 (2H, m, Alloc-H), 4.09-3.95 (3H, m, sidechain H-1, pyran H-6), 3.94 (3H, s, O/N—CH$_3$), 3.91 (3H, s, O/N—CH$_3$), 3.87 (3H, s, O/N—CH$_3$), 3.74 (3H, s, OCH$_3$), 3.57-3.44 (3H, m, H-3, 11a), 2.49 (2H, d, J=7.0 Hz, sidechain H-3), 2.13-1.99 (6H, m, H-1, 2, sidechain H-2), 1.64 (2H, m, pyran H-3), 1.49 (4H, m, pyran H-4, 5).

(ii) A solution of AllocTHPPBD conjugate (26) (0.065 g, 0.06 mmol) dissolved in dry CH$_2$Cl$_2$ (2 mL) under a nitrogen atmosphere was treated with pyrrolidine (5 μL, 0.07 mmol, 1.1 equiv.) and then palladium tetrakis[triphenylphosphine] (0.004 g, 0.003 mmol, 0.05 equiv.). The reaction mixture was stirred at room temperature for 2 hours and the product purified directly by column chromatography (silica gel, eluted with CHCl$_3$ 96%, MeOH 4%) to give the product as a glassy solid, 0.029 g (55%). [α]$^{26.5}_D$+129°; $^1$H-NMR (400 MHz) δ 9.94 (1H, s, N—H), 9.93 (1H, s, N—H), 9.90 (1H, s, N—H), 9.88 (1H, s, N—H), 7.78 (1H, d, J=4.4 Hz, H-11), 7.48 (1H, d, J=1.3 Hz, Py-H), 7.35 (1H, s, H-6), 7.25 (2H, s, Py-H), 7.17 (1H, d, J=0.8 Hz, Py-H), 7.08 (1H, d, J=1.1 Hz, Py-H), 7.06 (1H, d, J=0.9 Hz, Py-H), 6.92 (1H, d, J=1.2 Hz, Py-H), 6.90 (1H, s, Py-H), 6.83 (1H, s, H-9), 4.14 (1H, m, sidechain H-1), 4.05 (1H, m, sidechain H-1), 3.86 (3H, s, O/N—CH$_3$), 3.84 (3H, s, O/N—CH$_3$), 3.83 (3H, s, O/N—CH$_3$), 3.75 (3H, s, OCH$_3$), 3.68 (1H, m, H-11a), 3.61 (1H, m, H-3), 3.37 (1H, m, H-3), 2.45 (2H, m, sidechain H-3), 2.22 (2H, m, H-1), 2.05 (2H, m, sidechain H-2), 1.94 (2H, m, H-2); $^{13}$C-NMR (100 MHz) δ 168.8, 164.2 (C-11), 163.3, 160.8, 158.5, 158.4, 150.2, 146.9, 140.6, 123.0, 122.7, 122.5, 122.3, 122.1, 122.0, 120.7 (C-9), 119.8, 118.6 (py-CH), 118.5, 118.1, 111.3 (py-CH), 110.1 (C-6), 108.4 (py-CH), 104.8, 104.7 (py-CH), 104.0, 55.6 (C-11a), 53.4 (CH$_3$), 50.9 (CH$_3$), 46.4 (C-3), 36.1 (CH$_3$), 36.1 (CH$_3$), 31.9 (C-3 sidechain), 28.8 (C-1), 24.8 (C-2 sidechain), 23.7 (C-2); IR (solid) ν$_{max}$ 3289, 2947, 1706, 1632, 1580, 1433, 1250, 1199, 1106, 772 cm$^{-1}$; Acc. Mass C$_{42}$H$_{46}$N$_{100}$ g calc. 835.3522 found 835.3497

Example 1e (11aS) Methyl 4-({4-[(4-{[4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-1-methyl-1H-pyrrole-2-carbonyl]-amino}-1-methyl-1H-pyrrole-2-carbonyl)-amino]-1-methyl-1H-pyrrole-2-carbonyl}-amino)-1-methyl-1H-pyrrole-2-carboxylate (22, GWL 81)

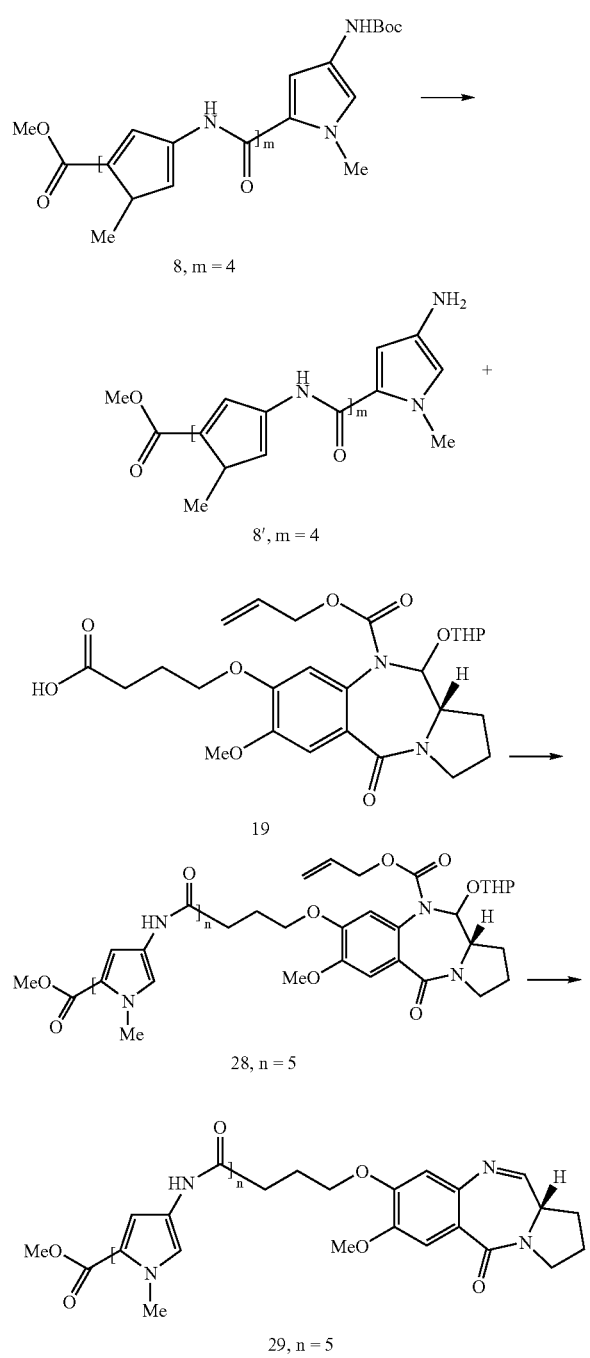

(i) A solution of Boc pyrrole pentamer (8) (0.150 g, 0.20 mmol) was treated with 4M HCl in dioxane (2 mL). The reaction mixture was stirred at room temperature for 30 minutes during which time a precipitate (8') formed. The solvent was removed and the residue dried in vacuo. The residue was dissolved in dry $CH_2Cl_2$ and AllocTHPPBD acid (19) (0.150 g, 0.2 mmol, 1 equiv.) was added followed by EDCI (0.1 µg, 0.40 mmol, 2 equiv.) and DMAP (0.088 g, 0.50 mmol, 2.5 equiv.). The reaction mixture was stirred for 24 hours then the solvent was removed in vacuo and the residue diluted with EtOAc (25 mL) and washed with 1M HCl solution (3×10 mL) then saturated $NaHCO_3$ solution (3×10 mL). The organic fraction was dried over $MgSO_4$ and concentrated in vacuo, to give an off white foamy solid (28), 0.164 g (71%). Mixture of diastereomers $^1$H-NMR (400 MHz) δ9.26 (1H, s, N—H), 9.22 (1H, s, N—H), 9.20 (1H, s, N—H), 7.50 (1H, d, J=1.6 Hz, Py-H), 7.23 (3H, d, J=1.7 Hz, Py-H), 7.15 (1H, s, H-6), 6.97 (2H, m, Py-H), 6.93 (2H, d, J=1.8 Hz, Py-H), 6.90 (1H, s, H-9), 6.84 (1H, d, J=2.0 Hz, Py-H), 6.80 (1H, d, J=2.0 Hz, Py-H), 5.89-5.77 (3H, m, H-11, Alloc-H), 5.10 (1H, m, pyran H-2), 4.60-4.41 (2H, m, Alloc-H), 4.10-3.95 (3H, m, sidechain H-1, pyran H-6), 3.94 (3H, s, O/N—$CH_3$), 3.92 (3H, s, O/N—$CH_3$), 3.91 (3H, s, O/N—$CH_3$), 3.87 (3H, s, O/N—$CH_3$), 3.76 (3H, s, $OCH_3$), 3.54-3.43 (3H, m, H-3, 11a), 2.50 (2H, m, sidechain H-3), 2.13-1.99 (6H, m, H-1, 2, sidechain H-2), 1.68 (2H, m, pyran H-3), 1.48 (4H, m, pyran H-4, 5).

(ii) A solution of AllocTHPPBD conjugate (28) (0.164 g, 0.14 mmol) dissolved in dry $CH_2Cl_2$ (2 mL) under a nitrogen atmosphere was treated with pyrrolidine (133 µL, 0.16 mmol, 1.1 equiv.) and then palladium tetrakis[triphenylphosphine] (0.008 g, 0.007 mmol, 0.05 equiv.). The reaction mixture was stirred at room temperature for 2 hours and the product purified directly by column chromatography (silica gel, eluted with $CHCl_3$ 96%, MeOH 4%) to give the product as a glassy solid, 0.068 g (50%). $[\alpha]^{26.7}_D$+90°; $^1$H-NMR (400 MHz) δ 9.95 (1H, s, N—H), 9.95 (1H, s, N—H), 9.94 (1H, s, N—H), 9.91 (1H, s, N—H), 9.89 (1H, s, N—H), 7.78 (1H, d, J=4.4 Hz, H-11), 7.48 (1H, d, J=1.8 Hz, Py-H), 7.35 (1H, s, H-6), 7.25 (3H, s, Py-H), 7.17 (1H, d, J=1.6 Hz, Py-H), 7.09 (1H, d, J=2.1 Hz, Py-H), 7.08 (1H, s, Py-H), 7.07 (1H, d, J=1.6 Hz, Py-H), 6.92 (1H, d, J=1.9 Hz, Py-H), 6.91 (1H, d, J=1.8 Hz, Py-H), 6.83 (1H, s, H-9), 4.14 (1H, m, sidechain H-1), 4.05 (1H, m, sidechain H-1), 3.87 (6H, s, O/N—$CH_3$), 3.86 (3H, s, O/N—$CH_3$), 3.85 (3H, s, O/N—$CH_3$), 3.83 (3H, s, O/N—$CH_3$), 3.75 (3H, s, $OCH_3$), 3.68 (1H, m, H-11a), 3.60 (1H, m, H-3), 3.39 (1H, m, H-3), 2.45 (2H, m, sidechain H-3), 2.26 (2H, m, H-1), 2.06 (2H, m, sidechain H-2), 1.94 (2H, m, H-2); $^{13}$C-NMR (100 MHz) δ 168.8, 164.2 (C-11), 163.3, 160.8, 158.5, 158.4, 150.2, 146.9, 140.6, 123.0, 122.7, 122.5, 122.3, 122.2, 122.1, 122.0, 120.7 (C-9), 118.6 (py-CH), 118.5 (py-CH), 118.2, 111.3 (py-CH), 110.1 (C-6), 108.4 (py-CH), 104.8 (py-CH), 104.8 (py-CH), 102.0, 67.8 (C-1 sidechain), 55.6 (C-11a), 53.4 ($CH_3$), 50.9 ($CH_3$), 46.4 (C-3), 36.2 ($CH_3$), 36.1 ($CH_3$), 31.9 (C-3 sidechain), 28.8 (C-1), 24.8 (C-2 sidechain), 23.7 (C-2); IR (solid) $v_{max}$ 3297, 2945, 1701, 1631, 1579, 1434, 1251, 1199, 1106, 774 cm$^{-1}$; Acc. Mass $C_{48}H_{52}N_{12}O_{10}$ calc. 957.4002 found 957.4010

Example 1f (11aS) Methyl 4-{[4-({4-[(4-{[4-({4-[4-(7-Methoxy-5-oxo-2,3,5,11a-tetrahydro-6H-pyrrolo[2,1-c][1,4]benzodiazepine-8-yloxy)-butyrylamino]-1-methyl-1H-pyrrole-2-carbonyl]-amino)-1-methyl-1H-pyrrole-2-carbonyl]-amino}-1-methyl-1H-pyrrole-2-carbonyl)-amino]-1-methyl-1H-pyrrole-2-carbonyl}-amino)-1-methyl-1H-pyrrole-2-carbonyl]-amino}-1-methyl-1H-pyrrole-2-carboxylate (31, GWL 82)

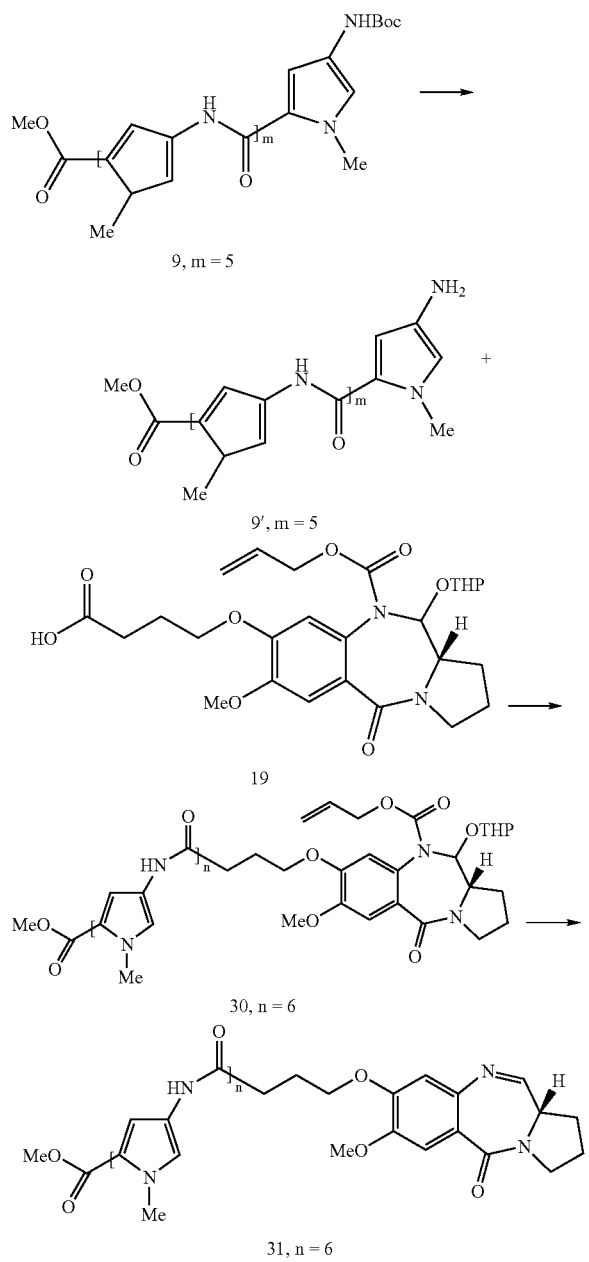

(i) A solution of Boc pyrrole hexamer (9) (0.155 g, 0.18 mmol) was treated with 4 M HCl in dioxane (2 mL). The reaction mixture was stirred at room temperature for 30 minutes during which time a precipitate (9') formed. The solvent was removed and the residue dried in vacuo. The residue was dissolved in dry $CH_2Cl_2$ and AllocTHPPBD acid (19) (0.093 g, 0.18 mmol, 1 equiv.) was added followed by EDCI (0.068 g, 0.36 mmol, 2 equiv.) and DMAP (0.054 g, 0.45 mmol, 2.5 equiv.). The reaction mixture was stirred for 24 hours then the solvent was removed in vacuo and the residue diluted with EtOAc (25 mL) and washed with 1M HCl solution (3×10 mL) then saturated $NaHCO_3$ solution (3×10 mL). The organic fraction was dried over $MgSO_4$ and concentrated in vacuo, to give an off white foamy solid (30), 0.174 g (77%). $^1$H-NMR (500 MHz) δ 9.28 (1H, s, N—H), 9.25 (1H, s, N—H), 9.23 (1H, s, N—H), 9.16 (1H, s, N—H), 7.50 (1H, d, J=1.8 Hz, Py-H), 7.24 (3H, d, J=1.5 Hz, Py-H), 7.16 (1H, s, H-6), 7.14 (2H, s, H-6, Py-H), 6.99 (1H, d, J=1.7 Hz, Py-H), 6.96 (1H, s, H-9), 6.93 (4H, d, J=1.9 Hz, Py-H), 6.83 (1H, d, J=2.3 Hz, Py-H), 6.79 (1H, s, Py-H), 5.89-5.77 (3H, m, Alloc-H), 5.11 (1H, m, pyran H-2), 4.62-4.42 (2H, m, Alloc-H), 4.12-3.95 (3H, m, sidechain H-1, pyran H-6), 3.94 (3H, s, O/N—$CH_3$), 3.93 (3H, s, O/N—$CH_3$), 3.91 (3H, s, O/N—$CH_3$), 3.87 (3H, s, O/N—$CH_3$), 3.81 (3H, s, O/N—$CH_3$), 3.75 (3H, s, $OCH_3$), 3.54-3.46 (3H, m, H-3, 11a), 2.49 (2H, m, sidechain H-3), 2.12-1.98 (6H, m, H-1, 2, sidechain H-2), 1.68 (2H, m, pyran H-3), 1.48 (4H, m, pyran H-4, 5).

(ii) A solution of AllocTHPPBD conjugate (30) (0.174 g, 0.14 mmol) dissolved in dry $CH_2Cl_2$ (2 mL) under a nitrogen atmosphere was treated with pyrrolidine (133 µL, 0.15 mmol, 1.1 equiv.) and then palladium tetrakis[triphenylphosphine] (0.008 g, 0.007 mmol, 0.05 equiv.). The reaction mixture was stirred at room temperature for 2 hours and the product purified directly by column chromatography (silica gel, eluted with $CHCl_3$ 96%, MeOH 4%) to give the product as a glassy solid, 0.084 g (57%). $[α]^{27.1}_D$+107°; $^1$H-NMR (400 MHz) δ 9.96 (2H, s, N—H), 9.95 (1H, s, N—H), 9.94 (1H, s, N—H), 9.91 (1H, s, N—H), 9.89 (1H, s, N—H), 7.78 (1H, d, J=4.4 Hz, H-11), 7.35 (1H, s, H-6), 7.26 (4H, m, Py-H), 7.17 (1H, d, J=1.6 Hz, Py-H), 7.09 (2H, d, J=1.5 Hz, Py-H), 7.08 (2H, d, J=1.7 Hz, Py-H), 6.92 (1H, d, J=1.9 Hz, Py-H), 6.91 (1H, d, J=1.8 Hz, Py-H), 6.84 (1H, s, H-9), 4.14 (1H, m, sidechain H-1), 4.05 (1H, m, sidechain H-1), 3.87 (12H, s, O/N—$CH_3$), 3.86 (3H, s, O/N—$CH_3$), 3.85 (3H, s, O/N—$CH_3$), 3.83 (3H, s, O/N—$CH_3$), 3.75 (3H, s, $OCH_3$), 3.68 (1H, m, H-11a), 3.61 (1H, m, H-3), 3.40 (1H, m, H-3), 2.45 (2H, m, sidechain H-3), 2.29-2.23 (2H, m, H-1), 2.06 (2H, m, sidechain H-2), 1.94 (2H, m, H-2); $^{13}$C-NMR (100 MHz) δ 168.8, 164.3 (C-11), 163.3, 160.8, 158.5, 158.4, 150.2, 146.9, 140.6, 123.0, 122.8, 122.7, 122.5, 122.3, 122.2, 122.1, 122.0, 120.7 (C-9), 119.8, 118.5, 118.5 (py-CH), 118.1, 111.3 (py-CH), 110.1 (C-6), 108.4 (py-CH), 104.8 (py-CH), 104.8 (py-CH), 104.8 (py-CH), 104.7 (py-CH), 104.7 (py-CH), 67.8 (C-1 sidechain), 55.6 (C-11a), 53.4 ($CH_3$), 50.9 ($CH_3$), 46.4 (C-3), 36.2 ($CH_3$), 36.2 ($CH_3$), 36.1 ($CH_3$), 36.0 ($CH_3$), 35.9 ($CH_3$), 31.9 (C-3 sidechain), 28.8 (C-1), 24.8 (C-2 sidechain), 23.7 (C-2); IR (solid) $ν_{max}$ 3300, 2945, 1701, 1634, 1581, 1433, 1250, 1200, 1106, 772 cm$^{-1}$; Acc. mass $C_{54}H_{58}N_{14}O_{11}$ calc. 1079.4482 found 1079.4542

Comparative Example 1

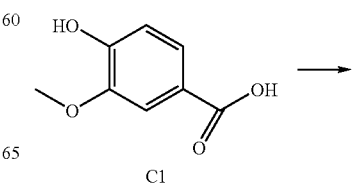

C1

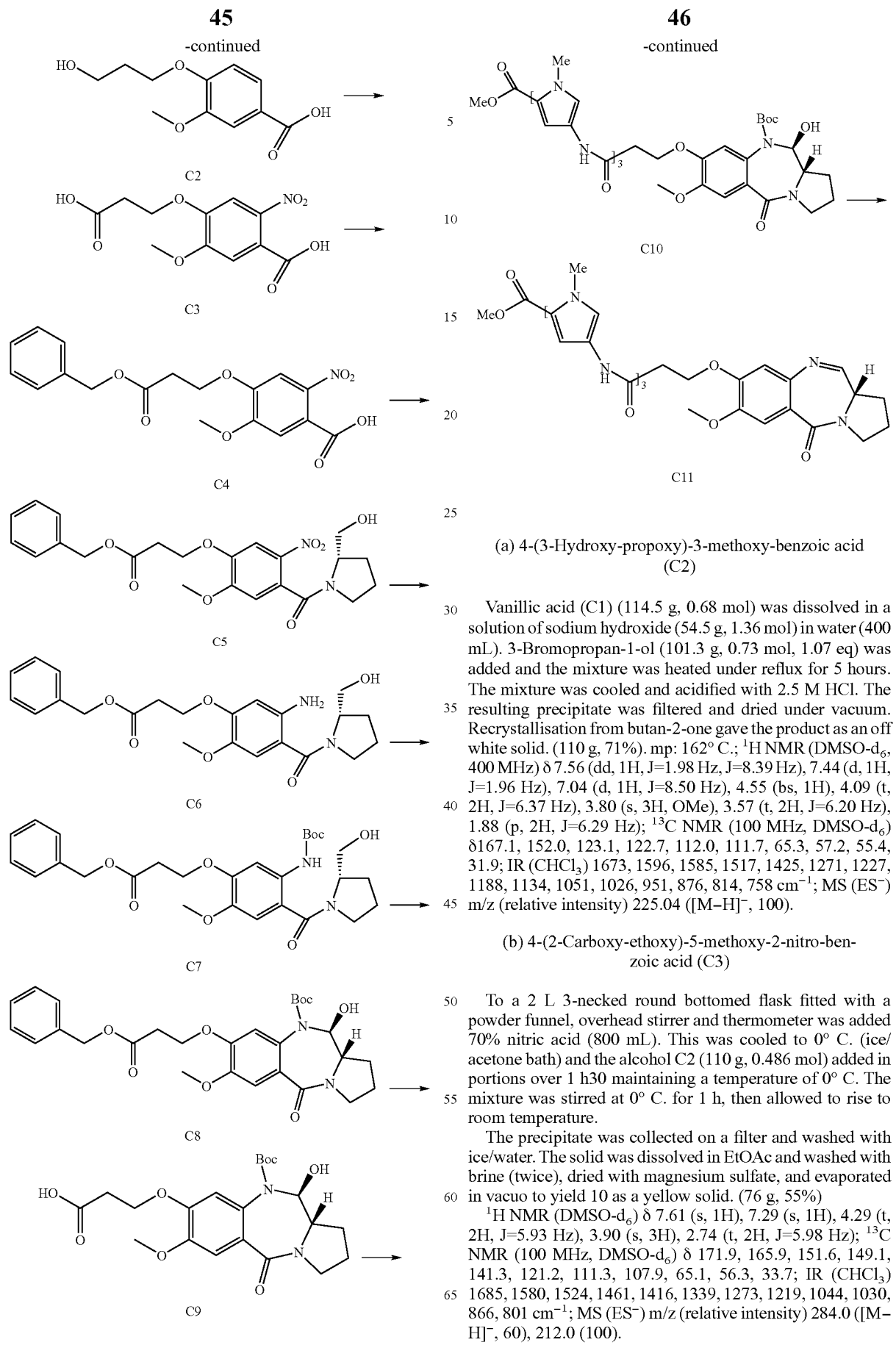

(a) 4-(3-Hydroxy-propoxy)-3-methoxy-benzoic acid (C2)

Vanillic acid (C1) (114.5 g, 0.68 mol) was dissolved in a solution of sodium hydroxide (54.5 g, 1.36 mol) in water (400 mL). 3-Bromopropan-1-ol (101.3 g, 0.73 mol, 1.07 eq) was added and the mixture was heated under reflux for 5 hours. The mixture was cooled and acidified with 2.5 M HCl. The resulting precipitate was filtered and dried under vacuum. Recrystallisation from butan-2-one gave the product as an off white solid. (110 g, 71%). mp: 162° C.; $^1$H NMR (DMSO-$d_6$, 400 MHz) δ 7.56 (dd, 1H, J=1.98 Hz, J=8.39 Hz), 7.44 (d, 1H, J=1.96 Hz), 7.04 (d, 1H, J=8.50 Hz), 4.55 (bs, 1H), 4.09 (t, 2H, J=6.37 Hz), 3.80 (s, 3H, OMe), 3.57 (t, 2H, J=6.20 Hz), 1.88 (p, 2H, J=6.29 Hz); $^{13}$C NMR (100 MHz, DMSO-$d_6$) δ167.1, 152.0, 123.1, 122.7, 112.0, 111.7, 65.3, 57.2, 55.4, 31.9; IR (CHCl$_3$) 1673, 1596, 1585, 1517, 1425, 1271, 1227, 1188, 1134, 1051, 1026, 951, 876, 814, 758 cm$^{-1}$; MS (ES$^-$) m/z (relative intensity) 225.04 ([M−H]$^-$, 100).

(b) 4-(2-Carboxy-ethoxy)-5-methoxy-2-nitro-benzoic acid (C3)

To a 2 L 3-necked round bottomed flask fitted with a powder funnel, overhead stirrer and thermometer was added 70% nitric acid (800 mL). This was cooled to 0° C. (ice/acetone bath) and the alcohol C2 (110 g, 0.486 mol) added in portions over 1 h30 maintaining a temperature of 0° C. The mixture was stirred at 0° C. for 1 h, then allowed to rise to room temperature.

The precipitate was collected on a filter and washed with ice/water. The solid was dissolved in EtOAc and washed with brine (twice), dried with magnesium sulfate, and evaporated in vacuo to yield 10 as a yellow solid. (76 g, 55%)

$^1$H NMR (DMSO-$d_6$) δ 7.61 (s, 1H), 7.29 (s, 1H), 4.29 (t, 2H, J=5.93 Hz), 3.90 (s, 3H), 2.74 (t, 2H, J=5.98 Hz); $^{13}$C NMR (100 MHz, DMSO-$d_6$) δ 171.9, 165.9, 151.6, 149.1, 141.3, 121.2, 111.3, 107.9, 65.1, 56.3, 33.7; IR (CHCl$_3$) 1685, 1580, 1524, 1461, 1416, 1339, 1273, 1219, 1044, 1030, 866, 801 cm$^{-1}$; MS (ES$^-$) m/z (relative intensity) 284.0 ([M−H]$^-$, 60), 212.0 (100).

(c) 4-(2-Benzyloxycarbonyl-ethoxy)-5-methoxy-2-nitro-benzoic acid (C4)

The diacid C3 (76 g, 0.266 mol) was suspended in toluene (760 mL). Para-toluenesulphonic acid (8.1 g, 0.16 eq) and benzyl alcohol (176.6 g, 169 mL, 6.14 eq) was added. The mixture was stirred under reflux for 3.5 h then allowed to cool to room temperature. The reaction mixture was then extracted with a saturated solution of aqueous sodium hydrogen carbonate and the combined aqueous extracts acidified to pH 2 with 1M HCl. It was then extracted with ethyl acetate (3×300 mL) and the precipitate was dissolved in ethyl acetate (600 mL). The combined ethyl acetate solutions were dried (magnesium sulfate) and evaporated in vacuo to give a yellow solid which was recrystallised from EtOAc/Hexane. (55.9 g, 56%).
$^1$H NMR (DMSO-$d_6$) δ 7.63 (s, 1H), 7.37-7.30 (m, 6H), 5.15 (s, 2H), 4.36 (t, 2H, J=5.82 Hz), 3.90 (s, 3H), 2.91 (t, 2H, J=5.88 Hz); $^{13}$C NMR (100 MHz, DMSO-$d_6$) δ 170.4, 166.0, 151.7, 148.9, 141.3, 136.0, 128.3, 127.9, 127.7, 121.4, 111.4, 108.2, 65.6, 65.0, 56.4, 33.7; IR (CHCl$_3$) 1704, 1603, 1537, 1424, 1395, 1349, 1278, 1213, 1181, 1050, 1022, 873, 753 cm$^{-1}$; MS (ES$^-$) m/z (relative intensity) 374.08 ([M–H]$^-$, 100).

(d) 3-[4-(2-Hydroxymethyl-pyrrolidine-1-carbonyl)-2-methoxy-5-nitro-phenoxy]-propionic acid benzyl ester (C5)

The benzyl ester C4 (30 g, 79.9 mmol) was suspended in dry DCM (300 mL) with stirring in a round-bottomed flask equipped with a drying tube. Oxalyl chloride (11.16 g, 7.66 mL, 1.1 eq) was added followed by a few drops of DMF. The mixture was stirred overnight at room temperature. Triethylamine (17.75 g, 24.45 mL, 2.2 eq), +(S)-pyrrolidine methanol (8.876 g, 8.66 mL, 1.1 eq) were dissolved in dry DCM (150 mL) under nitrogen. The solution was cooled below −30° C. The acid chloride solution was added dropwise over 6 h maintaining the temperature below −30° C. It was then left to stir overnight at room temperature. The resulting solution was extracted with 1N HCl (2×200 mL), twice with water, once with brine. It was dried with magnesium sulfate and concentrated in vacuo to give a yellow/brown oil which solidified on standing. (quantitative yield). It was used in the next step without further purification. $^1$H NMR (DMSO-$d_6$) Mixture of rotamers in a 35/65 ratio. δ 7.75 (m, 1H), 7.34 (m, 5H), 7.16 (s, 0.35H), 7.09 (s, 0.65H), 5.16 (s, 2H), 4.36 (m, 2H), 4.10 (m, 0.65H), 3.91 (s, 3H), 3.73-3.61 (m, 1H), 3.46-3.37 (m, 2.35H), 3.16-3.08 (m, 2H), 2.94-2.90 (m, 2H), 1.98-1.72 (m, 4H); $^{13}$C NMR (100 MHz, DMSO-d6) δ 170.4, 165.5, 154.0, 147.2, 136.9, 136.0, 128.6, 128.3, 128.2, 128.1, 127.9, 127.7, 109.9, 108.3, 79.1, 65.6, 64.8, 64.7, 61.7, 60.6, 59.9, 58.6, 56.6, 48.4, 45.7, 33.7, 27.4, 27.0, 23.4, 21.6; IR (CHCl$_3$) 1735, 1618, 1577, 1519, 1453, 1427, 1383, 1332, 1275, 1218, 1171, 1058, 871, 750, 698, 649 cm$^{-1}$; MS (ES$^+$) m/z (relative intensity) 459.13 ([M+H]$^+$, 100); [α]$^{25}_D$=−532° (c=0.12, CHCl$_3$).

(e) 3-[5-Amino-4-(2-hydroxymethyl-pyrrolidine-1-carbonyl)-2-methoxy-phenoxy]-propionic acid benzyl ester (C6)

The nitro compound C5 (59 g, 0.128 mol) was dissolved in methanol (650 mL). Tin chloride (130 g, 0.577 mol, 4.5 eq) was added and the mixture was heated under reflux for 6 hours until completion of the reaction (TLC, 5% methanol in ethyl acetate). The methanol was removed under vacuum and the residue was dissolved in ethyl acetate (1 L) in a 5 L flask and 2 L of saturated sodium hydrogen carbonate aqueous solution was carefully added. The mixture was mechanically stirred for 2 hours and the resulting emulsion was then left to settle overnight. The pH was 8. It was filtered through celite. The residue was washed twice with ethyl acetate and the aqueous layer was extracted with ethyl acetate. The organic layers were combined, dried with magnesium sulfate, and concentrated in vacuo to leave the crude product as a black tar (50 g). TLC analysis showed presence of small quantities of impurities but the product was use in the next step with no further purification. $^1$H NMR (CDCl$_3$) δ 7.36 (m, 5H), 6.74 (s, 1H), 6.28 (s, 1H), 5.19 (s, 2H), 4.28 (t, J=6.2 Hz, 2H), 3.73 (s, 3H), 3.77-3.50 (m, 2H), 2.91 (t, J=6.2 Hz, 2H), 2.15 (m, 1H), 1.88-1.60 (m, 2H).

(f) 3-[5-tert-Butoxycarbonylamino-4-(2-hydroxymethyl-pyrrolidine-1-carbonyl)-2-methoxy-phenoxy]-propionic acid benzyl ester (C7)

The crude amine C6 (39 g, 52.3 mmol) was dissolved in THF (650 mL), and the Boc anhydride (22.4 g, 0.103 mol) was added in one portion. The mixture was heated under reflux overnight. TLC showed reaction completion. (EtOAC). The THF was removed in vacuo and the residue dissolved in ethyl acetate (500 mL) and washed with water (2×200 mL), brine (200 mL), dried over magnesium sulfate and concentrated in vacuo to yield 53.2 g of a crude brown foam slightly contaminated with tert-butanol and solvent which was used in the next step with no further purification. $^1$H NMR (CDCl$_3$) δ 8.41 (br s, 1H), 7.82 (s, 1H), 7.34 (m, 5H), 6.81 (s, 1H), 5.18 (s, 2H), 4.39 (t, J=6.2 Hz, 2H), 3.76 (s, 3H), 3.77-3.47 (m, 2H), 2.93 (t, J=6.2 Hz, 2H), 2.05 (m, 1H), 1.88-1.60 (m, 2H), 1.50 (s, 9H).

(g) (11aS)-8-(2-benzyloxycarboxy-ethoxy)-7-methoxy-5-oxo-11-hydroxy-2,3,11,11a-tetrahydro-1H,5H-pyrrolo[2.1-c][1,4]benzodiazepine-10-carboxylic acid t-butyl ester (C8)

The crude Boc amine C7 (50 g, 0.094 mol) was dissolved in dry DCM (500 mL) at room temperature under nitrogen. 4 angstroms molecular sieves (47 g) and pyridinium dichromate (43 g, 0.114 mol, 1.2 eq) were added and the mixture was stirred for 4 h. The reaction was slightly exothermic at first, and once the exotherm had subsided, the mixture was sampled for TLC. After completion of the reaction, EtOAc (1 L) was added with stirring. The black mixture was filtered through celite. The black residue was mixed with warm EtOAc and filtered. (3×200 mL). Evaporation of the solvent yielded a black foam which was subjected to column chromatography using 70/30 EtOAc/Pet Et as eluant to give 16 g of pink colored foam (32% yield). (further chromatography of mixed fractions furnished 2 g of additional product to give a final yield around 35%). $^1$H NMR (400 MHz, CDCl$_3$) δ 7.34 (m, 5H), 7.22 (s, 1H), 6.66 (s, 1H), 5.55 (d, J=6.37 Hz, 1H) 5.18 (s, 2H), 4.40-4.23 (m, 2H), 3.88 (s, 3H), 3.76-3.44 (m, 4H), 2.93 (t, J=6.67 Hz, 2H), 2.14-1.98 (m, 4H), 1.36 (s, 9H); $^{13}$C NMR (100 MHz, CDCl$_3$) δ 170.5, 167.0, 149.5, 148.5, 135.6, 129.2, 128.6, 128.5, 128.3, 128.2, 126.2, 114.8, 110.8, 85.7, 81.8, 66.6, 64.7, 59.7, 56.1, 34.4, 28.8, 28.4, 23.0; IR (CHCl$_3$) 2975, 2362, 1698, 1603, 1514, 1455, 1433, 1394, 1322, 1164, 1042, 852, 731 cm$^{-1}$; MS (ES$^+$) m/z (relative intensity) 527.12 ([M+H]$^+$, 30), 471.07 (50), 409.07 (100); [α]$^{25}_D$=+335° (c=0.212, CHCl$_3$).

(h) (11aS)-8-(2-carboxy-ethoxy)-7-methoxy-5-oxo-11-hydroxy-2,3,11,11a-tetrahydro-1H,5H-pyrrolo[2.1-c][1,4]benzodiazepine-10-carboxylic acid t-butyl ester (C9)

The benzyl ester C8 (9 g, 17.1 mmol) was dissolved in ethanol (120 mL) and a slurry of Pd/C (0.5 g) in ethanol was added. The mixture was hydrogenated in a Parr hydrogenation apparatus at 16 psi until the hydrogen uptake ceased (2 h). The reaction mixture was filtered through celite and the residue washed with ethanol. The solvent was removed in vacuo to give the product as a white foam in quantitative yield.

$^1$H NMR (DMSO-d$_6$) δ 7.24 (s, 1H), 6.68 (s, 1H), 5.60 (d, J=10 Hz, 1H) 5.18 (s, 2H), 4.31 (t, J=7.5 Hz, 2H), 3.90 (s, 3H), 3.76-3.44 (m, 3H), 2.92 (t, J=6.2 Hz, 2H), 2.14-1.98 (m, 4H), 1.38 (s, 9H); $[\alpha]^{24.9}_D$=+104° (c=0.920, CHCl$_3$).

(i) (11aS)-1-Hydroxy-7-methoxy-8-(3-{5-[5-(5-methoxycarbonyl)-1-methyl-1H-pyrrol-3-ylcarbamoyl)-1-methyl-1H-pyrrol-3-ylcarbamoyl]-1-methyl-1H-pyrrol-3-ylcarbamoyl}-ethoxy)-5-oxo-2,3,11,11a-tetrahydro-1H,5H-pyrrolo[2,1-c][1,4]benzodiazepine-10-carboxylic acid tert-butyl ester (C10)

The Boc pyrrole trimer (6) (0.16 g, 0.32 mmol) in a dry round bottomed flask was treated with 4M HCl in dioxane (2.5 mL). The reaction mixture was stirred for 30 minutes during which time a precipitate formed. The solvent was then removed and the residue dried in vacuo. The residue was dissolved in dry DMF (2.5 mL) then the C$_3$BocPBD C9 (0.139 g, 0.32 mmol, 1 equiv.) was added followed by EDCI (0.122 g, 0.64 mmol, 2.0 equiv.) and DMAP (0.096 g, 0.80 mmol, 2.5 equiv.). The reaction mixture was stirred for 18 hours then diluted with EtOAc (40 mL) and washed with 10% citric acid solution (3×50 mL) then saturated NaHCO$_3$ solution (3×50 mL). The organic layer was dried over MgSO$_4$ and concentrated in vacuo to give a foamy solid, 0.170 g, (65%).
$^1$H-NMR (400 MHz) δ 10.07 (1H, s, N—H), 9.96 (2H, s, N—H), 7.49 (1H, d, J=1.8 Hz, Py-H), 7.26 (1H, d, J=1.6 Hz, Py-H), 7.21 (1H, d, J=1.6 Hz, Py-H), 7.07 (1H, d, J=1.6 Hz, Py-H), 7.06 (1H, s, H-9), 6.93 (1H, s, Py-H), 6.92 (1H, d, J=1.8 Hz, Py-H), 6.76 (1H, s, H-6), 6.46 (1H, bs, OH), 5.43 (1H, m, H-11), 4.16 (2H, m, sidechain H-1), 3.85 (6H, s, O/N—CH$_3$), 3.78 (3H, s, O/N—CH$_3$), 3.76 (3H, s, O/N—CH$_3$), 3.74 (3H, s, O/N—CH$_3$), 3.49 (1H, m, H-11a), 3.28 (2H, m, H-3), 2.78 (2H, m, sidechain H-2), 2.03-1.90 (4H, m, H-1, 2), 1.19 (9H, s, C[CH$_3$]$_3$).

(j) (11aS) Methyl 4-{[4-({4-[4-(7-Methoxy-5-oxo-2,3,5,11a-tetrahydro-5H-pyrrolo[2,1-c][1,4]benzodiazepine-8-yloxy)-propionylamino]-1-methyl-1H-pyrrole-2-carbonyl]-amino)-1-methyl-1H-pyrrole-2-carbonyl]-amino}-1-methyl-1H-pyrrole-2-carboxylate (C11)

The C$_3$BocPBD conjugate (C10) (0.053 g, 0.12 mmol) dissolved in a solution of TFA (2.5 mL) cooled to −10° C. The reaction mixture was stirred at this temperature for 3 hours then poured into a flask containing ice (~20 g). The mixture was adjusted to pH~8 by careful addition of saturated NaHCO$_3$ solution. The aqueous phase was extracted with chloroform (3×20 mL). The combined organic layers were dried over MgSO$_4$ and concentrated in vacuo to give a pale yellow foam, 0.044 g (96%). $[\alpha]^{26.3}_D$=+89° (CHCl$_3$); $^1$H-NMR d$_6$-DMSO (400 MHz) δ 9.99 (1H, s, N—H), 9.91 (1H, s, N—H), 9.90 (1H, s, N—H), 7.79 (1H, d, J=4.4 Hz, H-11), 7.46 (1H, d, J=1.8 Hz, Py-H), 7.33 (1H, s, H-9), 7.23 (1H, d, J=1.8 Hz, Py-H), 7.20 (1H, d, J=1.7 Hz, Py-H), 7.18 (1H, d, J=1.7 Hz, Py-H), 7.05 (1H, d, J=1.8 Hz, Py-H), 6.90 (1H, d, J=1.7 Hz, Py-H), 6.88 (1H, s, H-6), 4.17-4.00 (2H, m, sidechain H-1), 3.84 (3H, s, O/N—CH$_3$), 3.84 (6H, s, O/N—CH$_3$), 3.79 (3H, s, O/N—CH$_3$), 3.73 (3H, s, O/N—CH$_3$), 3.69-3.57 (2H, m, H-3, 11a), 3.40 (1H, m, H-3), 2.76 (2H, m, sidechain H-2), 2.25 (2H, m, H-1), 1.96 (2H, m, H-2), $[\alpha]^{263}_D$=+89° (CHCl$_3$)

Example 2

General Procedure A

Coupling Imidazole Containing Molecules

The amine molecule was dissolved in dry DMF or DCM (5 mL) and the acid (1 equiv.) was added. The resulting mixture was treated with EDCI (2 equiv.) and DMAP (2.5 equiv.) and allowed to stir for 72 hours. The reaction mixture was diluted with DCM (40 mL) and washed with deionised water (3×30 mL) then sat. NaHCO$_3$ solution (3×30 mL). The organic layer was dried over MgSO$_4$ and concentrated in vacuo to give the product.

General Procedure B: Coupling Thiazole Containing Molecules

The amine molecule was dissolved in dry DMF or DCM (5 mL) and the acid (1 equiv.) was added. The resulting mixture was treated with EDCI (2 equiv.) and DMAP (2.5 equiv.) and allowed to stir for 10 days. The reaction mixture was diluted with DCM (40 mL) and washed with 10% citric acid solution (3×30 mL) then sat. NaHCO$_3$ solution (3×30 mL). The organic layer was dried over MgSO$_4$ and concentrated in vacuo to give the product.

General Procedure C: Boc Deprotection (4M HCl in dioxane)

The Boc protected amine was treated with 4M HCl in dioxane (5 mL). The reaction mixture was allowed to stir for 30 mins during which time a precipitate formed. The solvent was removed in vacuo and the remaining residue was dried under vacuum.

General Procedure D: Boc Deprotection (95% TFA)

The Boc protected amine was treated with 95% aqueous TFA (5 mL) and allowed to stir for 30 mins. The solvent was removed in vacuo and the residue was dried under vacuum.

General Procedure E: Alloc Deprotection

The AllocTHPPBD-heterocycle conjugate was dissolved in dry DCM (5 mL) and was treated with pyrrolidine (1.1 equiv.) and palladium tetrakis[triphenylphosphine] (0.05 equiv.). The reaction mixture was allowed to stir at room temperature for 1 hour. The solvent was removed in vacuo and the product was purified using a preparative HPLC coupled to a mass directed fraction collector. Pure fractions were combined and lyophilised to yield the solid product.

Synthesis of Key Intermediates

(i) 4-[(4-tert-Butoxycarbonylamino-1-methyl-1H-imidazole-2-carbonyl)-amino]-1-methyl-1H-pyrrole-2-carboxylic acid methyl ester (32)

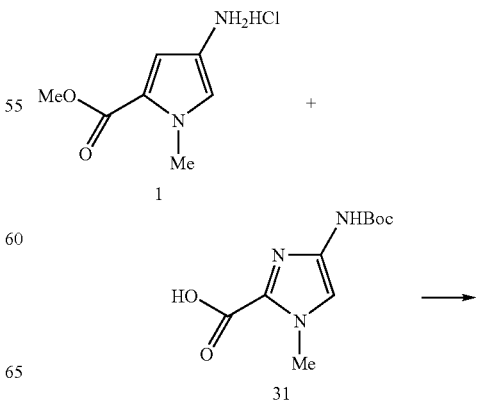

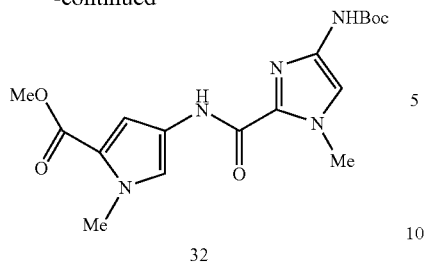

32

The pyrrole amine (1) (0.100 g, 0.525 mmol) and the Boc protected imidazole acid (31) (0.127 g, 0.525 mmol) were dissolved in dry DCM (5 mL) and reacted according to general procedure A. This yielded a brown foam 0.151 g (76%). LCMS (method 1) rt=3.43 min; m/z (ES+) 378 (M+1).

(ii) 4-[(4-tert-Butoxycarbonylamino-1-methyl-1H-pyrrole-2-carbonyl)-amino]-1-methyl-1H-imidazole-2-carboxylic acid ethyl ester (34)

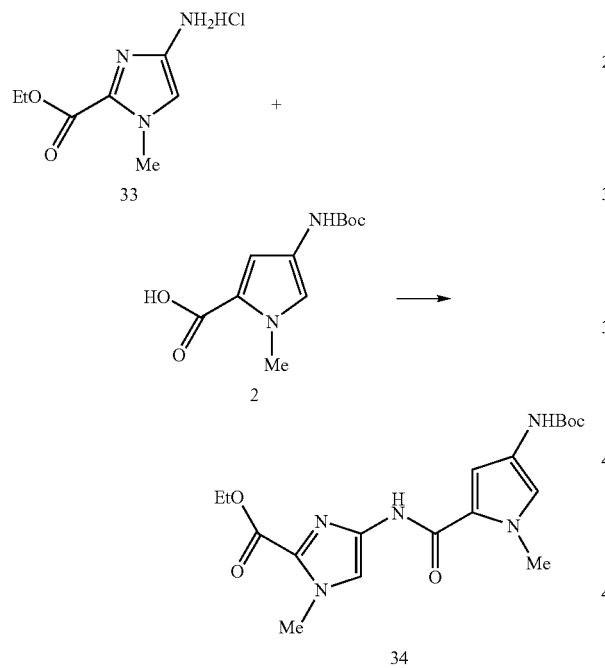

The imidazole amine (33) (0.500 g, 2.95 mmol) and the Boc protected pyrrole acid (2) (0.710 g, 2.95 mmol) were dissolved in dry DMF (5 mL) and reacted according to general procedure A. This yielded an orange foam 1.163 g (95%). LCMS (method 2) rt=1.77 min; m/z (ES+) 392 (M+1).

(iii) 2-[(4-tert-Butoxycarbonylamino-1-methyl-1H-pyrrole-2-carbonyl)-amino]-thiazole-4-carboxylic acid ethyl ester (36)

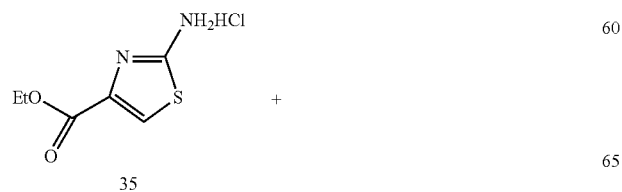

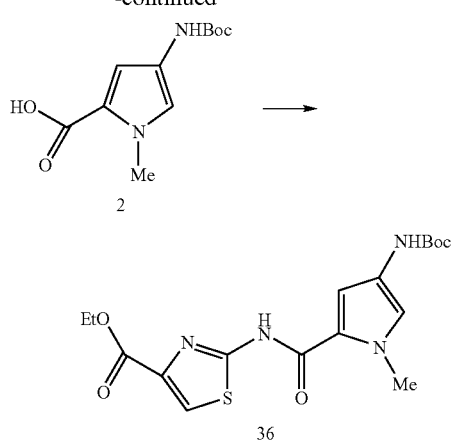

The thiazole amine (35) (0.500 g, 1.98 mmol) and the Boc protected pyrrole acid (2) (0.470 g, 1.98 mmol) were dissolved in dry DMF (5 mL) and reacted according to general procedure B. This yielded a cream foam 0.546 g (70%). LCMS (method 1) rt=3.62 min; m/z (ES+) 395 (M+1).

(iv) 4-[(2-tert-Butoxycarbonylamino-thiazole-4-carbonyl)-amino]-1-methyl-1H-pyrrole-2-carboxylic acid methyl ester (38)

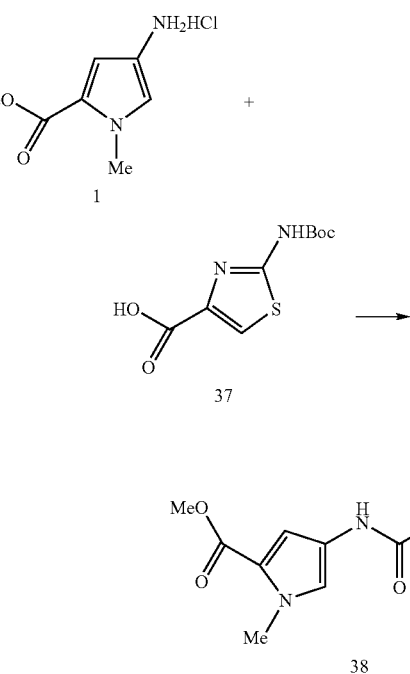

The pyrrole amine (1) (0.500 g, 2.74 mmol) and the Boc protected thiazole acid (37) (0.668 g, 2.74 mmol) were dissolved in dry DMF (5 mL) and the reaction was performed as described in general procedure B. This solution was treated with EDCI (1.5 equiv.) and DMAP (1.2 equiv.). The product was an off-white foam 0.797 g (77%). LCMS (method 1) rt=3.30 min; m/z (ES+) 381 (M+1).

(v) 4-[(4-tert-Butoxycarbonylamino-1-methyl-1H-imidazole-2-carbonyl)-amino]-1-methyl-1H-imidazole-2-carboxylic acid ethyl ester (39)

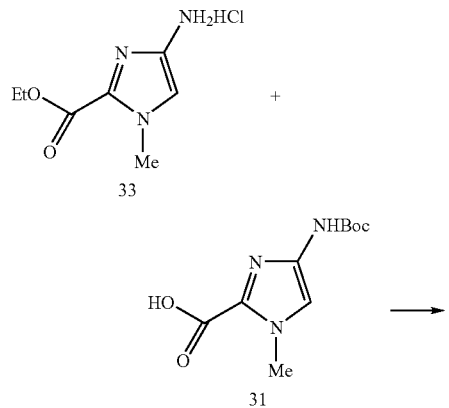

The imidazole amine (33) (0.500 g, 2.96 mmol) and the Boc protected imidazole acid (31) (0.714 g, 2.96 mmol) were dissolved in dry DMF (5 mL). The reaction was performed as described in general procedure A, using EDCI (1.5 equiv.) and DMAP (1.2 equiv.). Concentration in vacuo yielded a foam, 0.825 g, which was purified using column chromatography (silica gel, eluted with EtOAc 70%, Hexane 30%) to give a yellow foam 0.506 g (43%). LCMS (method 2) rt=1.77 min; m/z (ES+) 393 (M+1).

(vi) 2-[(2-tert-Butoxycarbonylamino-thiazole-4-carbonyl)-amino]-thiazole-4-carboxylic acid ethyl ester (40)

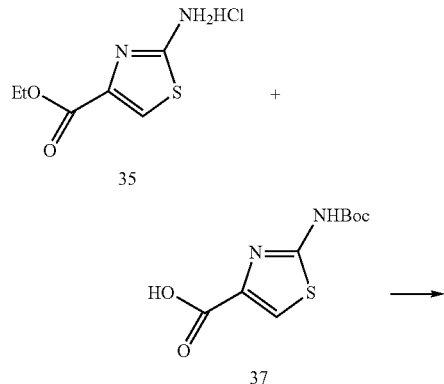

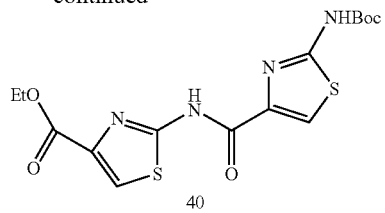

The thiazole amine (35) (0.500 g, 1.98 mmol) and the Boc protected thiazole acid (37) (0.483 g, 1.98 mmol) were dissolved in dry DMF. The reaction was performed as described in general procedure B, using EDCI (1.5 equiv.) and DMAP (1.2 equiv.). This yielded a yellow foam 0.562 g (71%). LCMS (method 1) rt=3.70 min; m/z (ES+) 399 (M+1).

(vii) 4-({4-[(4-tert-Butoxycarbonylamino-1-methyl-1H-imidazole-2-carbonyl)-amino]-1-methyl-1H-pyrrole-2-carbonyl}-amino)-1-methyl-1H-pyrrole-2-carboxylic acid methyl ester (41)

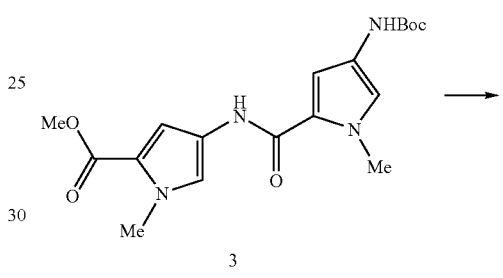

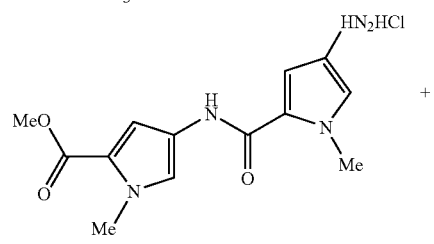

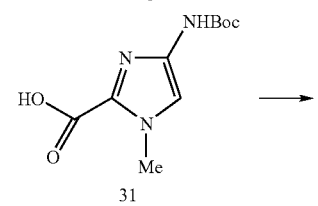

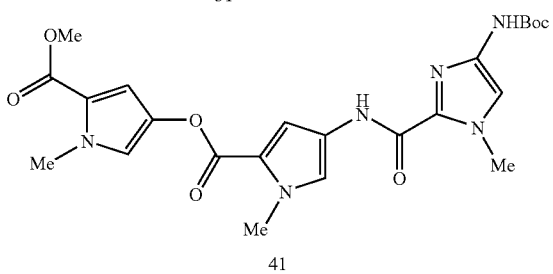

The Boc pyrrole dimer (3) (0.400 g, 1.06 mmol) was deprotected using 4M HCl in dioxane as described in general procedure C. The resulting residue (3') was dissolved in dry DCM (5 mL) and the Boc protected imidazole acid (31) (0.256 g, 1.06 mmol) was added and reacted as described in general procedure A. This yielded a brown foam 0.527 g (99%). LCMS (method 2) rt=1.90 min; m/z (ES+) 500 (M+1).

55

(viii) 4-({4-[(2-tert-Butoxycarbonylamino-thiazole-2-carbonyl)-amino]-1-methyl-1H-pyrrole-2-carbonyl}-amino)-1-methyl-1H-pyrrole-2-carboxylic acid methyl ester (42)

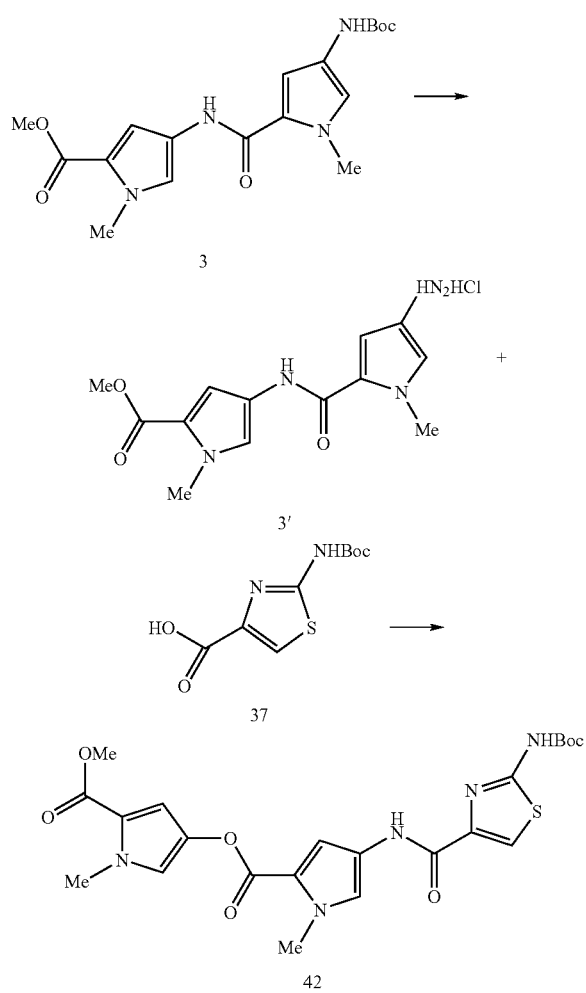

The Boc pyrrole dimer (3) (0.300 g, 0.80 mmol) was deprotected using 4M HCl in dioxane as described in general procedure C. The resulting residue (3') was dissolved in dry DCM (5 mL) and the Boc protected thiazole acid (37) (0.195 g, 0.80 mmol) was added and reacted as described in general procedure B. This yielded a brown foam 0.368 g (76%). LCMS (method 1) rt=3.35 min; m/z (ES+) 502 (M+1).

(ix) 4-({4-[(4-tert-Butoxycarbonylamino-1-methyl-1H-pyrrole-2-carbonyl)-amino]-1-methyl-1H-imidazole-2-carbonyl}-amino)-1-methyl-1H-pyrrole-2-carboxylic acid methyl ester (43)

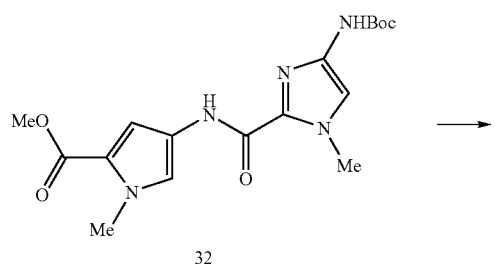

56

-continued

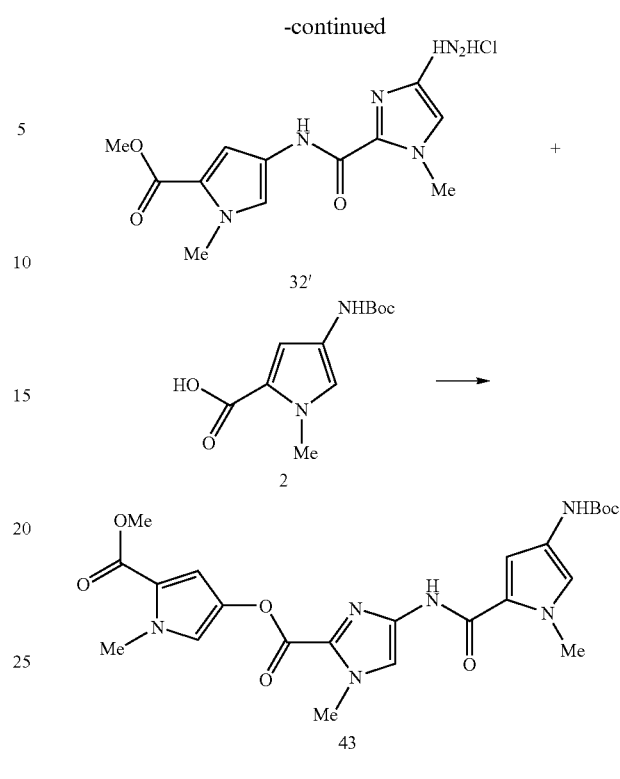

The Boc pyrrole-imidazole dimer (32) (0.263 g, 0.70 mmol) was deprotected using 4M HCl in dioxane as described in general procedure C. The resulting residue (32') was dissolved in dry DMF (5 mL) and the Boc protected pyrrole acid (2) (0.169 g, 0.70 mmol) was added and reacted as described in general procedure A. This yielded an orange foam 0.256 g (73%). LCMS (method 2) rt=1.87 min; m/z (ES+) 500 (M+1).

(x) 4-({2-[(4-tert-Butoxycarbonylamino-1-methyl-1H-pyrrole-2-carbonyl)-amino]-thiazole-4-carbonyl}-amino)-1-methyl-1H-pyrrole-2-carboxylic acid methyl ester (44)

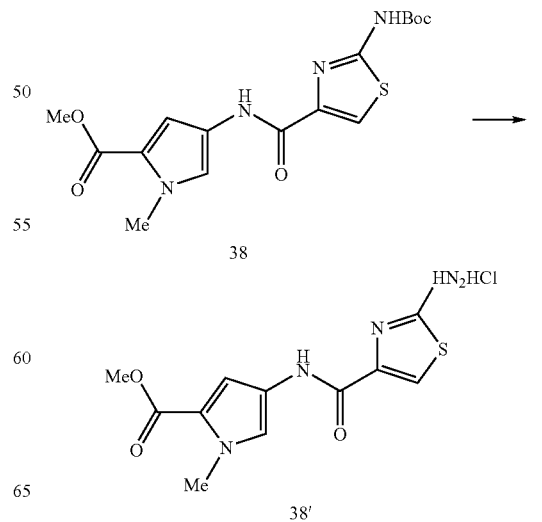

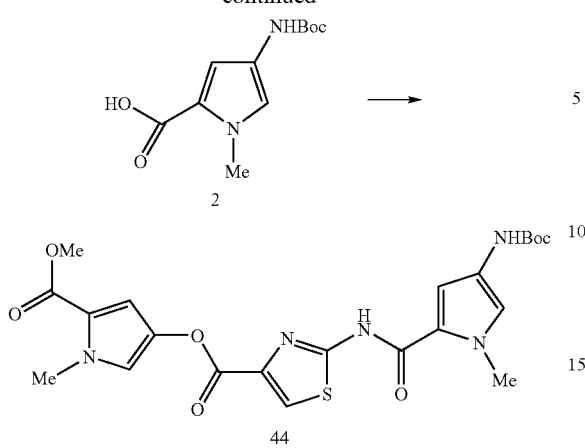

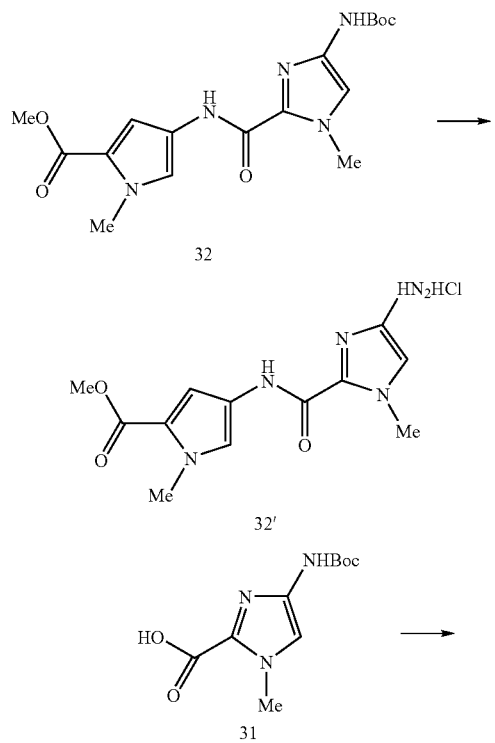

The Boc pyrrole-thiazole dimer (38) (0.399 g, 1.07 mmol) was deprotected using 4M HCl in dioxane as described in general procedure C. The resulting residue (38') was dissolved in dry DMF (5 mL) and the Boc protected pyrrole acid (2) (0.258 g, 1.07 mmol) was added and reacted as described in general procedure B. This yielded a brown foam 0.367 g, which was purified by column chromatography (silica gel, eluted with DCM 98%, MeOH 2%) to give 0.303 g (56%), MS m/z (ES+) 503 (M+1).

(xi) 4-({4-[(4-tert-Butoxycarbonylamino-1-methyl-1H-imidazole-2-carbonyl)-amino]-1-methyl-1H-imidazole-2-carbonyl}-amino)-1-methyl-1H-pyrrole-2-carboxylic acid methyl ester (45)

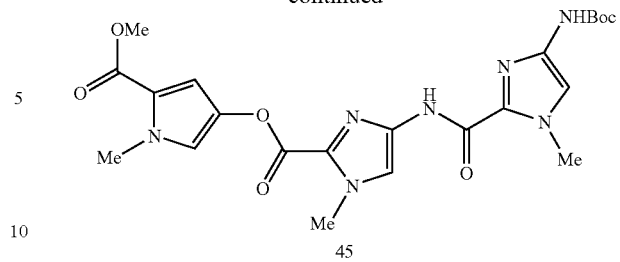

The Boc pyrrole-imidazole dimer (32) (0.263 g, 0.70 mmol) was deprotected using 4M HCl in dioxane as described in general procedure C. The resulting residue (32') was dissolved in dry DMF (5 mL) and the Boc protected imidazole acid (31) (0.169 g, 0.70 mmol) was added and reacted as described in general procedure A This yielded a brown foam 0.367 g, which was purified by column chromatography (silica gel, eluted with DCM 98%, MeOH 2%) to give 0.303 g (56%), LCMS (method 1) rt=3.58 min; m/z (ES+) 501 (M+1).

(xii) 4-({4-[(4-tert-Butoxycarbonylamino-1-methyl-1H-imidazole-2-carbonyl)-amino]-1-methyl-1H-imidazole-2-carbonyl}-amino)-1-methyl-1H-imidazole-2-carboxylic acid ethyl ester (46)

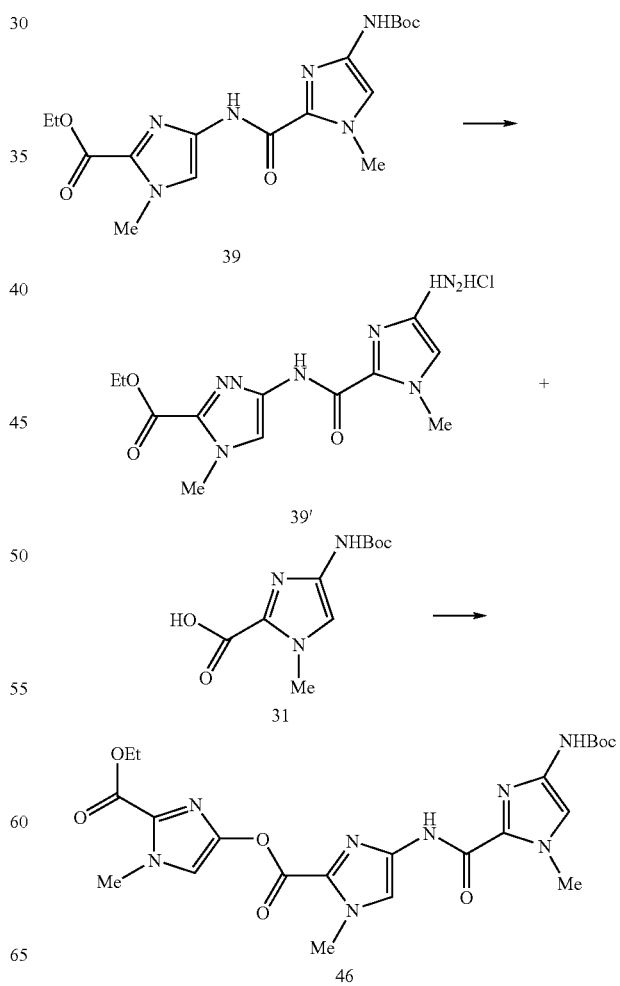

The Boc imidazole dimer (39) (0.253 g, 0.65 mmol) was deprotected using 4M HCl in dioxane as described in general procedure C. The resulting residue (39') was dissolved in dry DMF (5 mL) and the Boc protected imidazole acid (31) (0.150 g, 0.65 mmol) was added. The resulting solution was treated with EDCI (1.5 equiv.) and DMAP (2 equiv.) and reacted as described in general procedure A. This yielded a brown foam 0.160 g (48%). LCMS (method 1) rt=3.45 min; m/z (ES+) 516 (M+1).

(xiii) 4-({4-[(4-tert-Butoxycarbonylamino-1-methyl-1H-pyrrole-2-carbonyl)-amino]-1-methyl-1H-imidazole-2-carbonyl}-amino)-1-methyl-1H-imidazole-2-carboxylic acid ethyl ester (47)

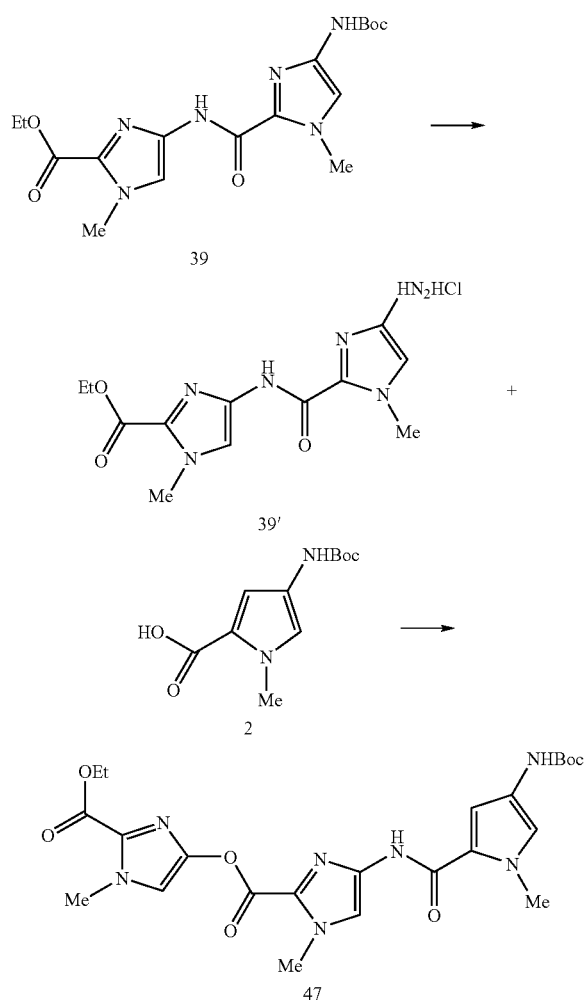

The Boc imidazole dimer (39) (0.253 g, 0.65 mmol) was deprotected using 4M HCl in dioxane as described in general procedure C. The resulting residue (39') was dissolved in dry DMF (5 mL) and the Boc protected pyrrole acid (2) (0.156 g, 0.65 mmol) was added. The resulting solution was treated with EDCI (1.5 equiv.) and DMAP (2 equiv.) and reacted as described in general procedure A. This yielded a brown foam 0.109 g (32%). LCMS (method 2) rt=1.87 min; m/z (ES+) 515 (M+1).

(xiv) 4-({4-[(4-tert-Butoxycarbonylamino-1-methyl-1H-pyrrole-2-carbonyl)-amino]-1-methyl-1H-pyrrole-2-carbonyl}-amino)-1-methyl-1H-imidazole-2-carboxylic acid ethyl ester (48)

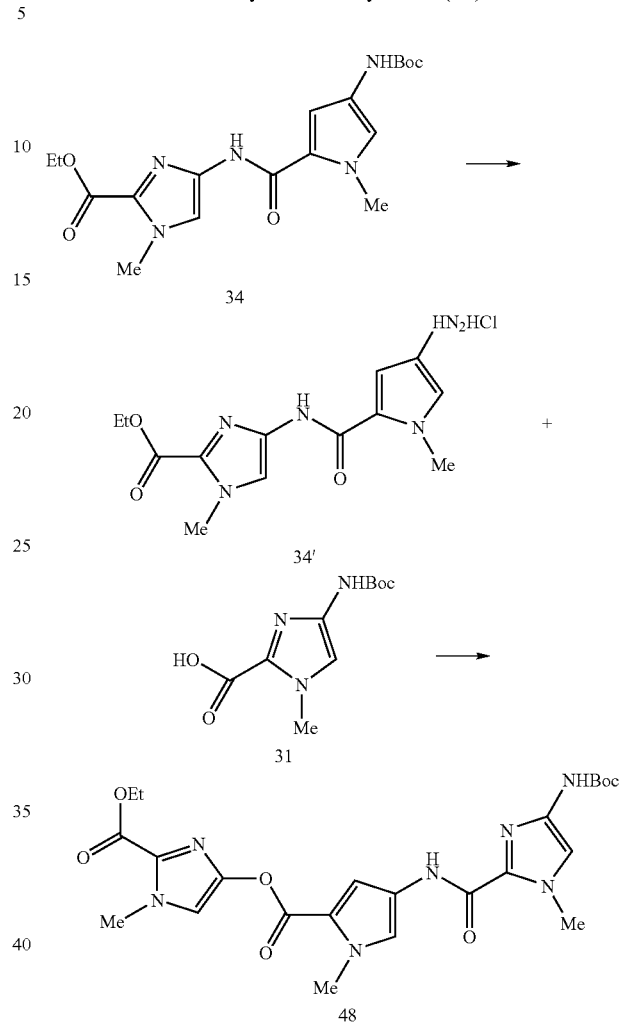

The Boc imidazole-pyrrole dimer (34) (0.200 g, 0.51 mmol) was deprotected using 4M HCl in dioxane as described in general procedure C. The resulting residue (34') was dissolved in dry DMF (5 mL) and the Boc protected imidazole acid (31) (0.123 g, 0.51 mmol) was added and reacted as described in general procedure A. This yielded a brown foam 0.220 g (84%).
LCMS (method 2) rt=1.83 min; m/z (ES+) 515 (M+1).

(xv) 2-({2-[(2-tert-Butoxycarbonylamino-thiazole-4-carbonyl)-amino]-thiazole-4-carbonyl}-amino)-thiazole-4-carboxylic acid ethyl ester (49)

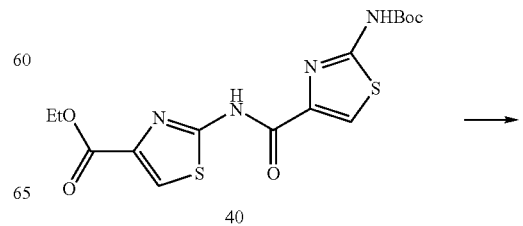

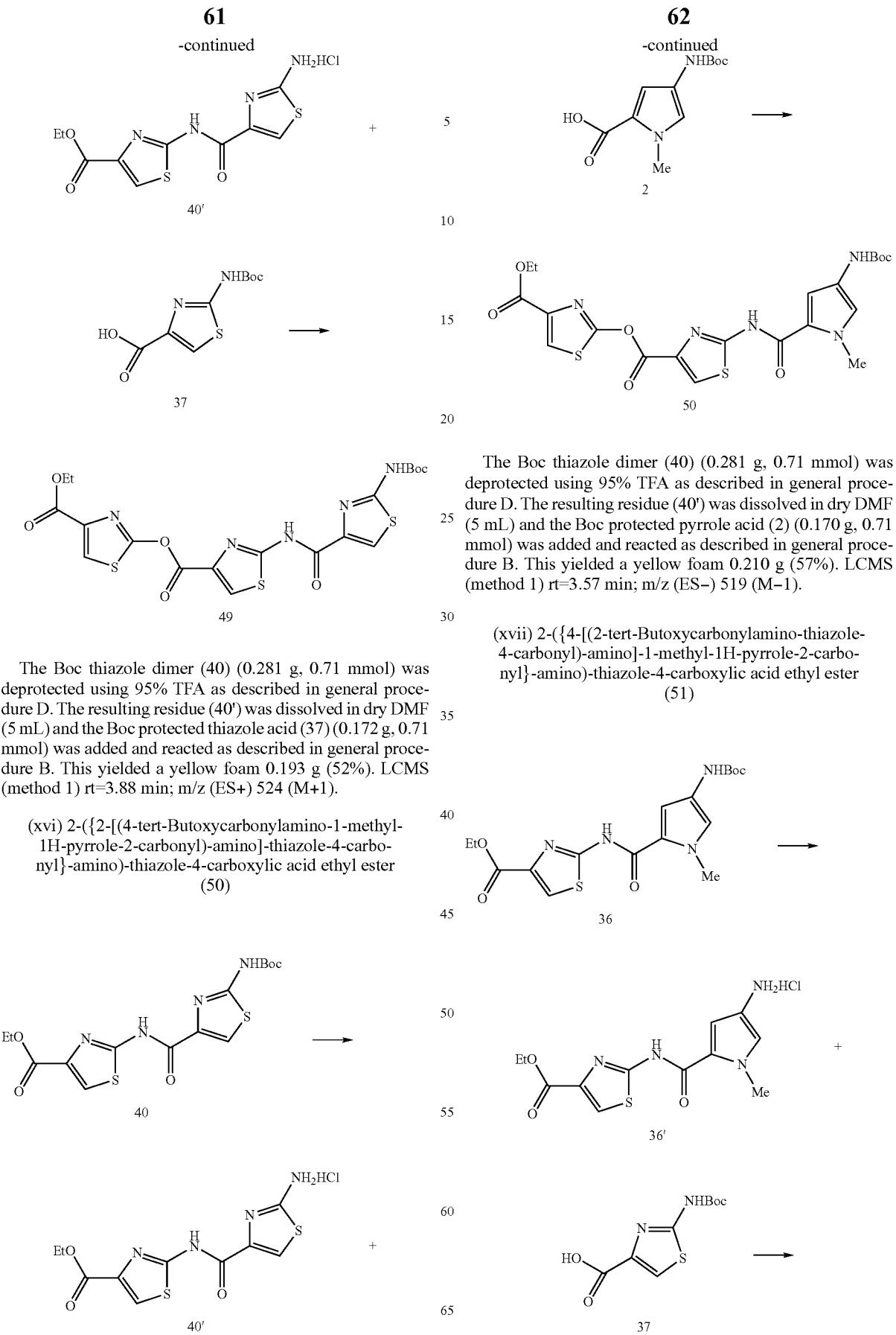

The Boc thiazole dimer (40) (0.281 g, 0.71 mmol) was deprotected using 95% TFA as described in general procedure D. The resulting residue (40') was dissolved in dry DMF (5 mL) and the Boc protected thiazole acid (37) (0.172 g, 0.71 mmol) was added and reacted as described in general procedure B. This yielded a yellow foam 0.193 g (52%). LCMS (method 1) rt=3.88 min; m/z (ES+) 524 (M+1).

(xvi) 2-({2-[(4-tert-Butoxycarbonylamino-1-methyl-1H-pyrrole-2-carbonyl)-amino]-thiazole-4-carbonyl}-amino)-thiazole-4-carboxylic acid ethyl ester (50)

The Boc thiazole dimer (40) (0.281 g, 0.71 mmol) was deprotected using 95% TFA as described in general procedure D. The resulting residue (40') was dissolved in dry DMF (5 mL) and the Boc protected pyrrole acid (2) (0.170 g, 0.71 mmol) was added and reacted as described in general procedure B. This yielded a yellow foam 0.210 g (57%). LCMS (method 1) rt=3.57 min; m/z (ES−) 519 (M−1).

(xvii) 2-({4-[(2-tert-Butoxycarbonylamino-thiazole-4-carbonyl)-amino]-1-methyl-1H-pyrrole-2-carbonyl}-amino)-thiazole-4-carboxylic acid ethyl ester (51)

-continued

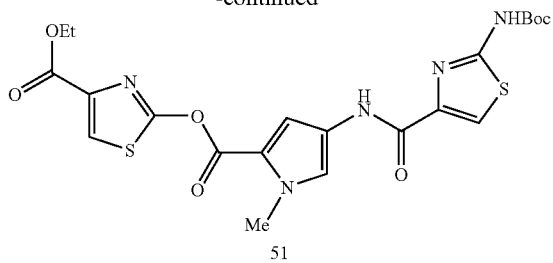

51

The Boc thiazole-pyrrole dimer (36) (0.250 g, 0.64 mmol) was deprotected using 4M HCl in dioxane as described in general procedure C. The resulting residue (36') was dissolved in dry DMF (5 mL) and the Boc protected thiazole acid (37) (0.155 g, 0.64 mmol) was added and reacted as described in general procedure B. This yielded a yellow foam 0.282 g (86%). LCMS (method 1) rt=3.05 min; m/z (ES+) 521 (M+1).

(xviii) 2-({4-[(4-tert-Butoxycarbonylamino-1-methyl-1H-pyrrole-2-carbonyl)-amino]-1-methyl-1H-pyrrole-2-carbonyl}-amino)-thiazole-4-carboxylic acid ethyl ester (52)

The Boc thiazole-pyrrole dimer (36) (0.200 g, 0.51 mmol) was deprotected using 4M HCl in dioxane as described in general procedure C. The resulting residue (36') was dissolved in dry DCM (5 mL) and the Boc protected pyrrole acid (2) (0.122 g, 0.51 mmol) was added and reacted as described in general procedure B. This yielded an off-white foam 0.210 g (80%). LCMS (method 1) rt=3.65 min; m/z (ES+) 516 (M+1).

(xix) 4-({4-[(4-tert-Butoxycarbonylamino-1-methyl-1H-pyrrole-2-carbonyl)-amino]-1-methyl-1H-pyrrole-2-carbonyl}-amino)-1-methyl-1H-imidazole-2-carboxylic acid ethyl ester (53)

The Boc imidazole-pyrrole dimer (34) (0.200 g, 0.51 mmol) was deprotected using 4M HCl in dioxane as described in general procedure C. The resulting residue (34') was dissolved in dry DMF (5 mL) and the Boc protected pyrrole acid (0.123 g, 0.51 mmol) was added and reacted as described in general procedure A. This yielded an orange foam 0.240 g (91%). LCMS (method 1) rt=2.02 min; m/z (ES+) 517 (M+1).

Example 2a (11aS) Ethyl 4-({2-[4-(7-Methoxy-5-oxo-2,3,5,11a-tetrahydro-5H-pyrrolo[2,1-c][1,4]benzodiazepine-8-yloxy)-butyrylamino]-thiazole-4-carbonyl}-amino)-1-methyl-1H-pyrrole-2-carboxylate (55)

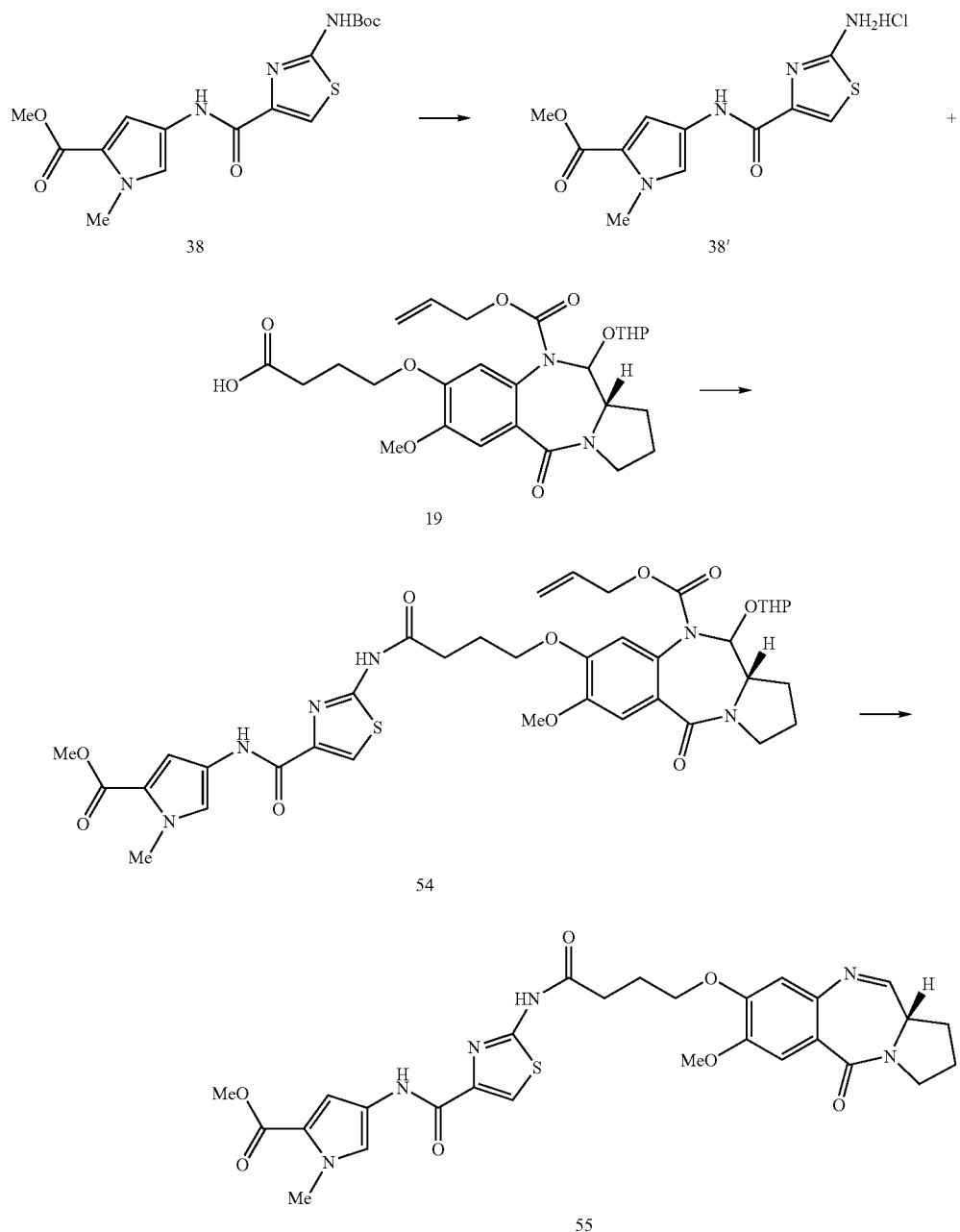

(i) The Boc pyrrole-thiazole dimer (38) (0.150 g, 0.40 mmol) was deprotected using 4M HCl in dioxane as described in general procedure C. The resulting residue (38') was dissolved in dry DCM (5 mL) and the AllocTHPPBD acid (19) (0.205 g, 0.40 mmol) was added and reacted as described in general procedure B. This yielded a yellow foam 0.208 g (66%). LCMS (method 1) rt=3.35 min; m/z (ES+) 781 (M+1).

(ii) The AllocTHPPBD-pyrrole-thiazole conjugate (54) (0.188 g, 0.24 mmol) was deprotected as described in general procedure E to yield 0.012 g (8%) $^1$H-NMR $d_6$-acetone (400 MHz) δ 11.29 (s, 1H) 9.28 (s, 1H) 7.81 (s, 1H) 7.74 (d, 1H, J=4.4 Hz) 7.53 (d, 1H, J=1.9 Hz) 7.40 (s, 1H) 6.96 (d, 1H, J=2.0 Hz) 6.81 (s, 1H) 4.19 (m, 2H,) 3.91 (s, 3H) 3.87 (s, 3H) 3.77 (s, 3H) 3.69 (m, 1H) 3.46 (m, 2H) 2.53 (s, 2H) 2.36 (m, 2H) 2.26 (m, 2H) 2.09 (s, 2H); LCMS (method 1) rt=2.57; m/z (ES+) 595 (M+1).

Example 2b (11aS) Methyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-imidazole-2-carbonyl}-amino)-1-methyl-1H-pyrrole-2-carboxylate (57)

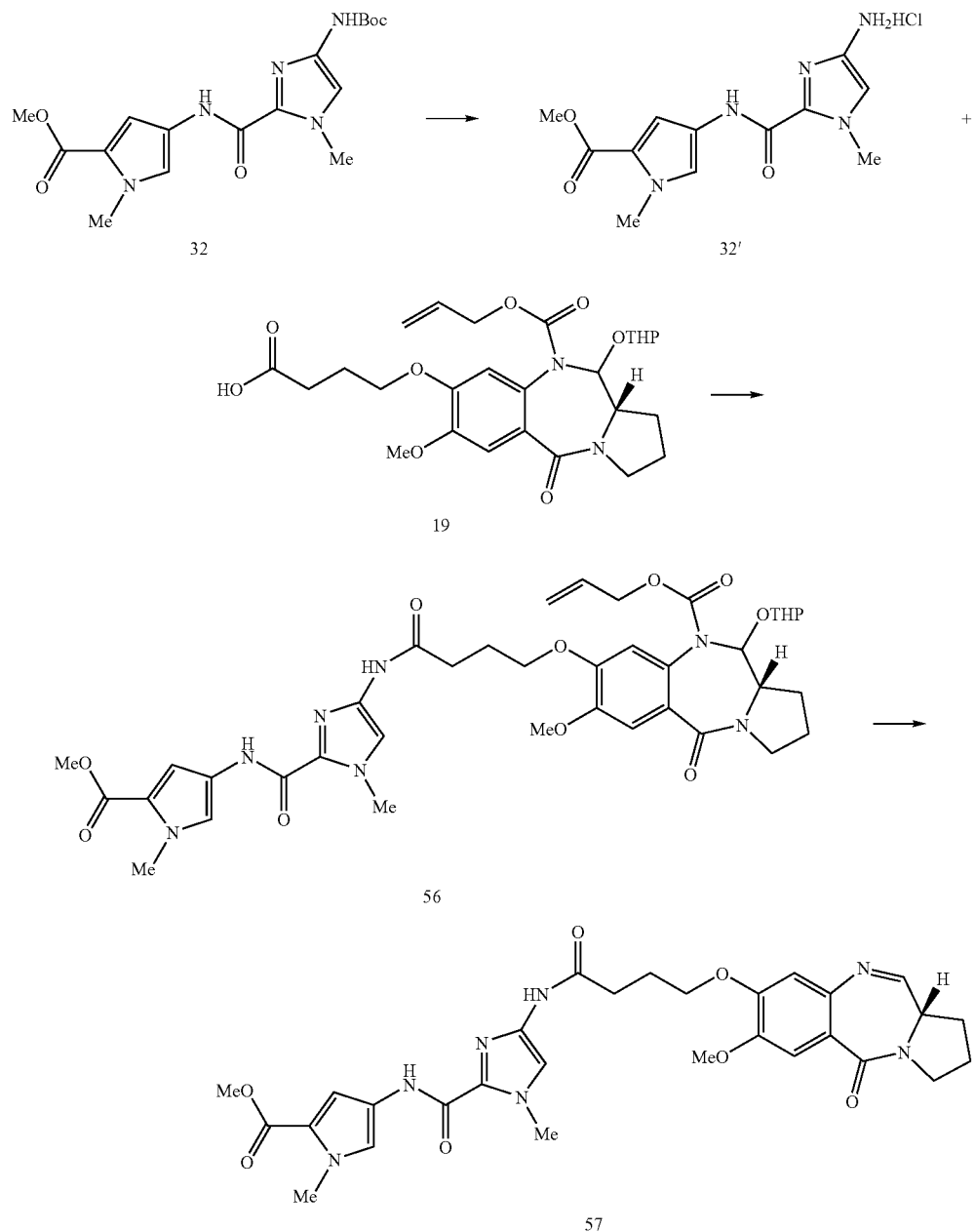

(i) The Boc pyrrole-imidazole dimer (32) (0.100 g, 0.27 mmol) was deprotected using 4M HCl in dioxane as described in general procedure C. The resulting residue (32') was dissolved in dry DCM (5 mL) and the AllocTHPPBD acid (19) (0.137 g, 0.27 mmol) was added and reacted as described in general procedure B. This yielded a brown foam 0.151 g (72%). LCMS (method 1) rt=3.47 min; m/z (ES+) 778 (M+1).

(ii) The AllocTHPPBD-pyrrole-imidazole conjugate (56) (0.160 g, 0.21 mmol) was deprotected as described in general procedure E to yield 0.031 g (25%). $^1$H-NMR $d_6$-acetone (400 MHz) δ 9.56 (s, 1H) 8.39 (s, 1H) 8.11 (s, 1H) 7.51 (m, 2H) 7.35 (s, 1H) 7.01 (d, 1H, J=4.2 Hz) 6.81 (s, 1H) 4.08 (s, 1H) 3.96 (m, 1H, J=2.8 Hz) 3.92 (s, 3H) 3.84 (s, 3H) 3.77 (s, 3H) 3.74 (m, 1H) 3.59 (m, 1H) 2.66 (m, 2H) 2.54 (m, 2H) 2.21 (m, 2H) 2.09 (m, 2H); LCMS (method 1) rt=2.53 min; m/z (ES+) 592 (M+1).

Example 2c (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-imidazole-2-carbonyl}-amino)-1-methyl-1H-imidazole-2-carboxylate (59)

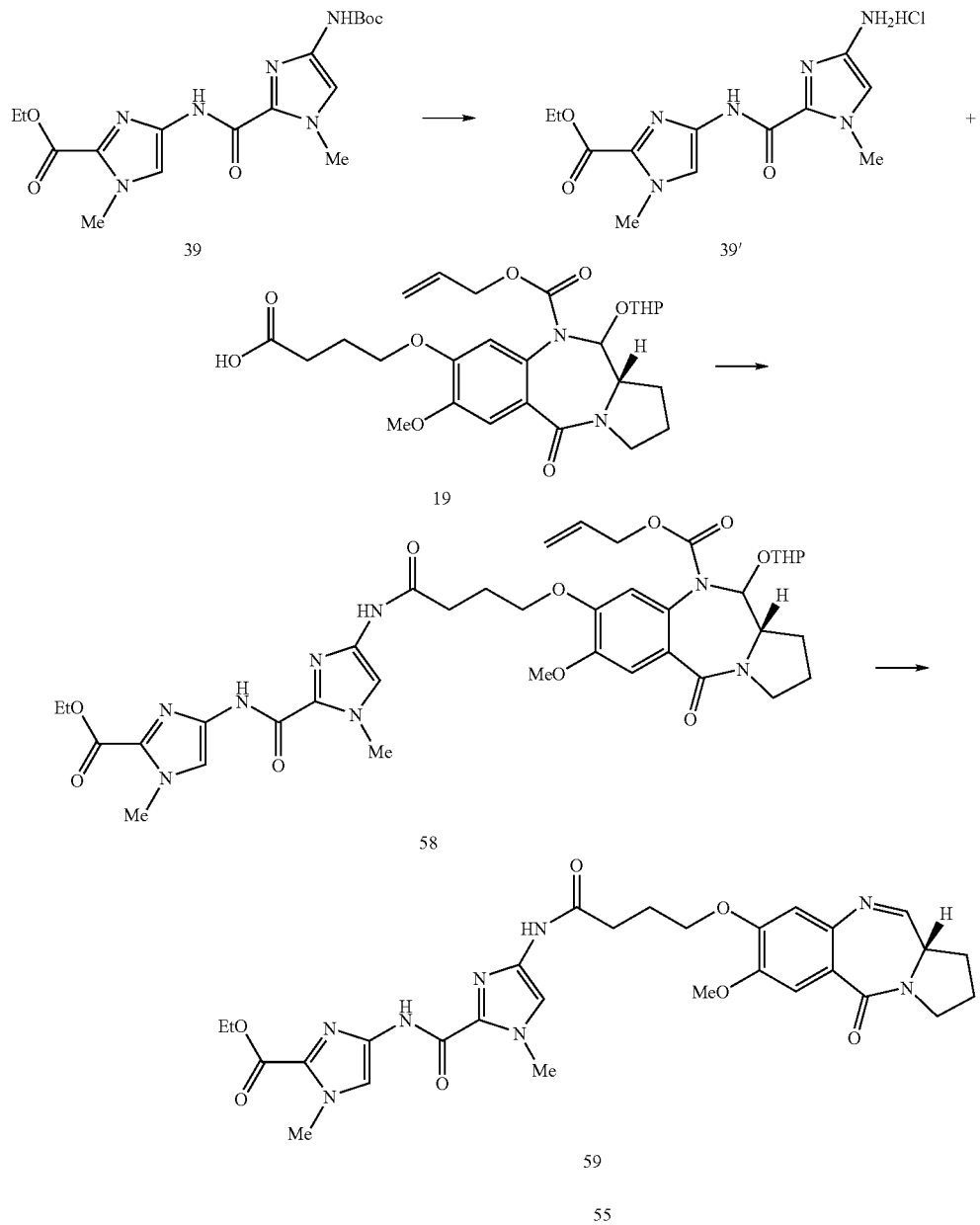

(i) The Boc imidazole dimer (39) (0.130 g, 0.33 mmol) was deprotected using 4M HCl in dioxane as described in general procedure C. The resulting residue (39') was dissolved in dry DCM (5 mL) and the AllocTHPPBD acid (19) (0.172 g, 0.33 mmol) was added and reacted as described in general procedure A. This yielded a brown foam 0.090 g (34%). LCMS (method 1) rt=3.38 min; m/z (ES+) 793 (M+1).

(ii) The AllocTHPPBD-imidazole dimer conjugate (58) (0.060 g, 0.076 mmol) was dissolved in dry DCM (5 mL) and was treated with pyrrolidine (1.1 equiv.) and palladium tetrakis[triphenylphosphine] (0.05 equiv.). The reaction mixture was allowed to stir at room temperature for 1 hour. The solvent was removed in vacuo and the product was purified directly by column chromatography (silica gel, eluted with DCM 96%, MeOH 4%) to give the product as an off-white foam, 0.041 g (90%). $^1$H-NMR d$_6$-acetone (400 MHz) δ 9.72 (s, 1H) 9.33 (s, 1H) 7.74 (d, 1H, J=4.4 Hz) 7.59 (s, 1H) 7.50 (s, 1H) 7.42 (s, 1H) 6.81 (s, 1H) 4.33 (q, 2H, J=7.1 Hz) 4.14 (m, 2H) 4.07 (s, 3H) 4.03 (s, 3H) 3.87 (s, 3H) 3.70 (m, 2H) 3.49 (m, 1H) 2.64 (m, 2H) 2.35 (m, 2H) 2.19 (m, 2H,) 2.09 (m, 2H) 1.35 (t, 3H, J=7.1 Hz); LCMS (method 1) rt=2.48 min; m/z (ES+) 607 (M+1).

Example 2d (11aS) Ethyl 2-({2-[4-(7-Methoxy-5-oxo-2,3,5,11a-tetrahydro-5H-pyrrolo[2,1-c][1,4]benzodiazepine-8-yloxy)-butyrylamino]-thiazole-4-carbonyl}-amino)-thiazole-4-carboxylate (61)

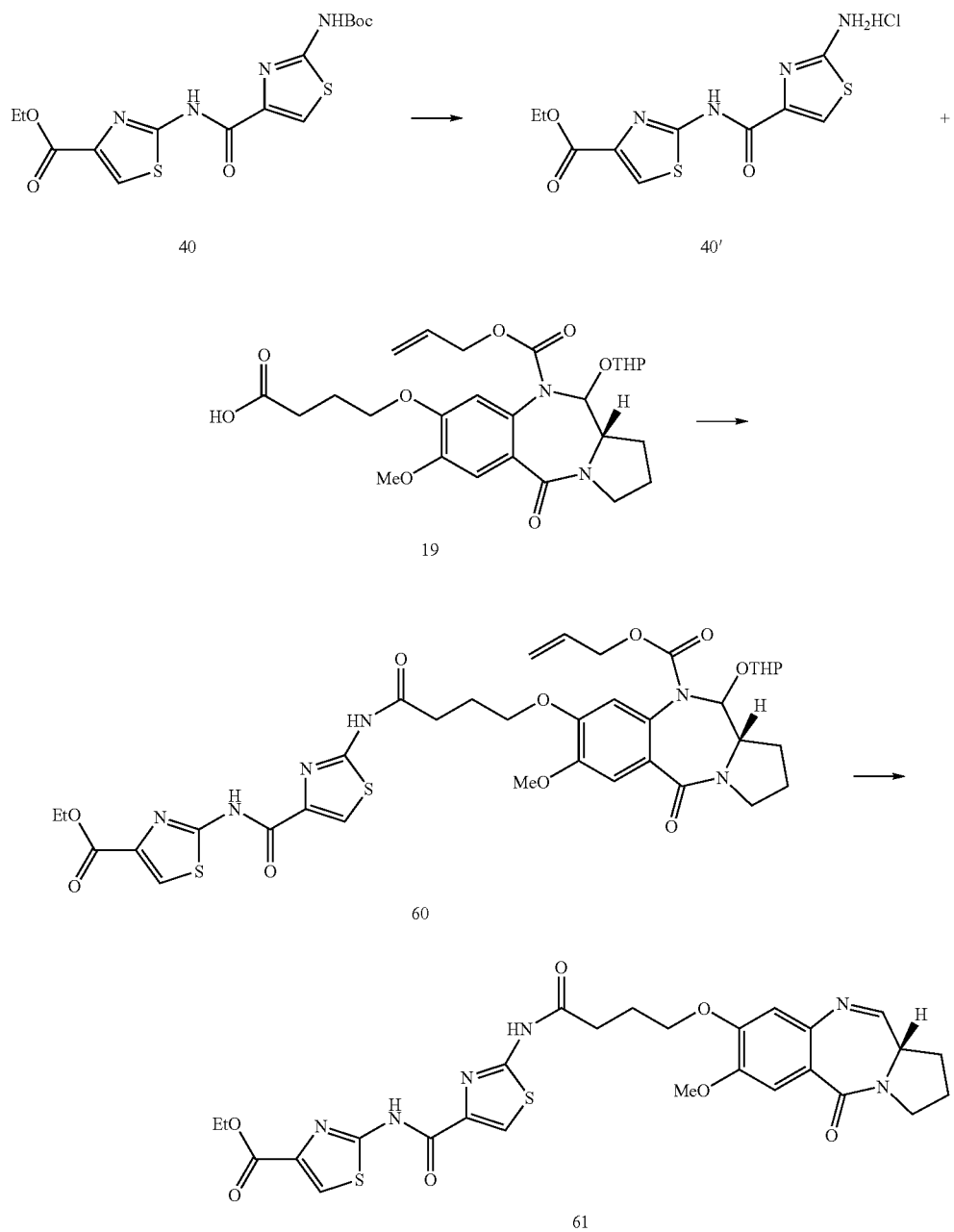

(i) The Boc thiazole dimer (40) (0.156 g, 0.39 mmol) was deprotected using 95% TFA as described in general procedure D. The resulting residue (40') was dissolved in dry DCM (5 mL) and the AllocTHPPBD acid (19) (0.202 g, 0.39 mmol) was added and reacted as described in general procedure B. This yielded a yellow foam 0.102 g (34%). LCMS (method 1) rt=3.58 min; m/z (ES+) 799 (M+1).

(ii) The AllocTHPPBD-thiazole-thiazole conjugate (60) (0.080 g, 0.10 mmol) was deprotected as described in general procedure E to yield 0.025 g (40%). $^1$H-NMR d$_6$-acetone (400 MHz) δ 11.57 (s, 1H) 10.71 (s, 1H) 8.11 (s, 1H) 8.03 (s, 1H) 7.75 (d, 1H, J=4.4 Hz) 7.40 (s, 1H) 6.82 (s, 1H) 4.32 (q, 2H, J=7.1 Hz) 4.20 (m, 2H) 3.81 (s, 3H) 3.69 (m, 2H) 3.46 (m, 1H) 2.85 (m, 2H) 2.36 (m, 2H) 2.27 (m, 2H) 2.03 (m, 2H) 1.35 (t, 3H, J=7.1 Hz); LCMS (method 1) rt=2.78; m/z (ES+) 613 (M+1).

Example 2e (11aS) Ethyl 2-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl}-amino)-thiazole-4-carboxylate (63)

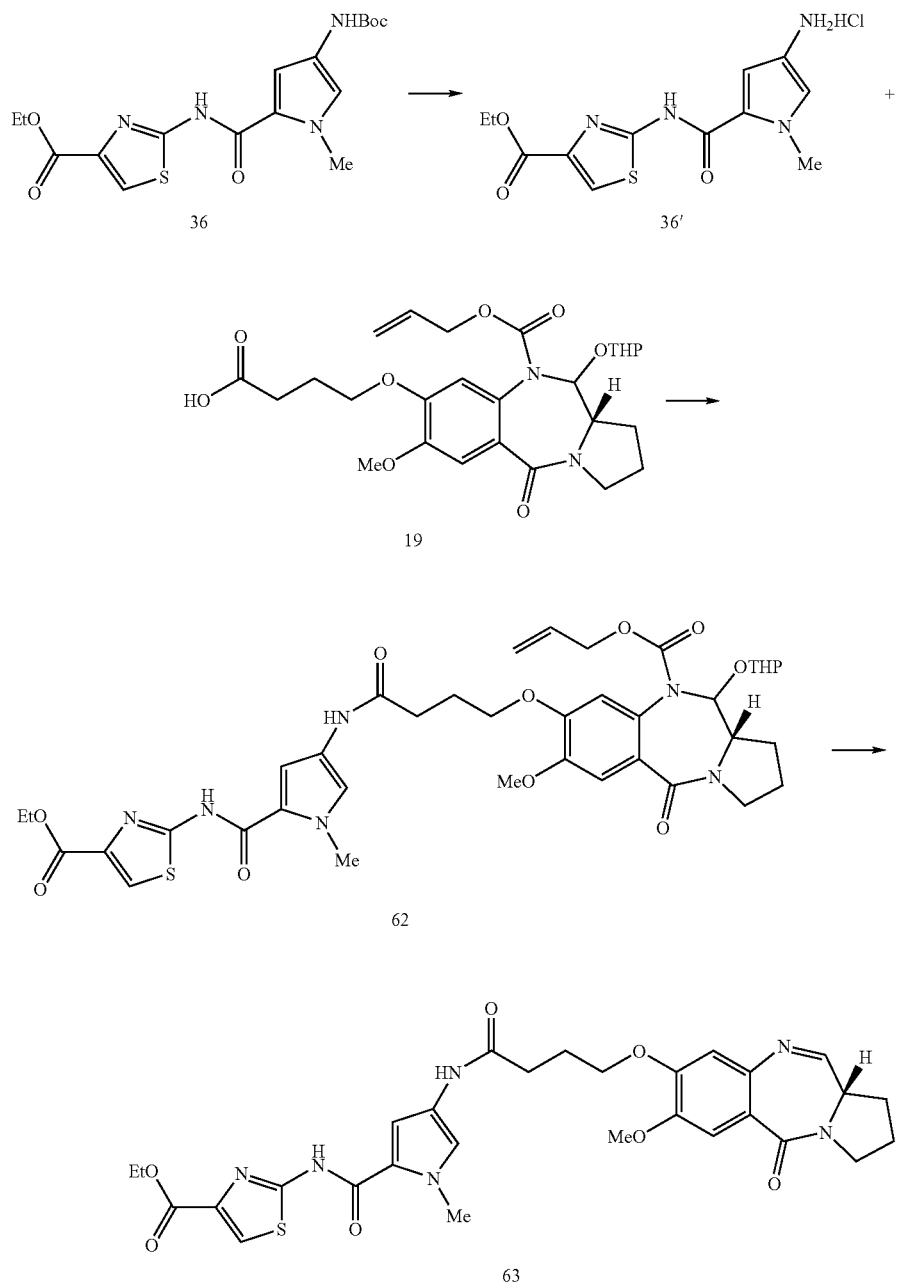

(i) The Boc pyrrole-thiazole dimer (36) (0.150 g, 0.38 mmol) was deprotected using 4M HCl in dioxane as described in general procedure C. The resulting residue (36') was dissolved in dry DCM (5 mL) and the AllocTHPPBD acid (19) (0.197 g, 0.38 mmol) was added and reacted as described in general procedure B. This yielded a yellow foam 0.274 g (90%). LCMS (method 1) rt=3.45 min; m/z (ES+) 795 (M+1).

(ii) The AllocTHPPBD-thiazole-pyrrole conjugate (60) (0.215 g, 0.27 mmol) was deprotected as described in general procedure E to yield 0.025 g (15%) $^1$H-NMR $d_6$-acetone (400 MHz) δ 10.82 (s, 1H) 9.31 (s, 1H) 7.93 (s, 1H) 7.74 (d, 1H, J=4.3 Hz) 7.54 (d, 1H, J=1.5 Hz) 7.41 (s, 1H) 7.32 (d, 1H, J=1.8 Hz) 6.81 (s, 1H) 4.32 (q, 2H, J=7.3 Hz) 4.15 (m, 2H) 3.99 (s, 3H) 3.87 (s, 3H) 3.68 (m, 2H) 3.46 (m, 1H) 2.56 (m, 2H) 2.37 (m, 2H) 2.18 (m, 2H) 1.35 (t, 3H, J=7.1 Hz); LCMS (method 1) rt=2.73; m/z (ES+) 609 (M+1).

Example 2f (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl}-amino)-1-methyl-1H-imidazole-2-carboxylate (65)

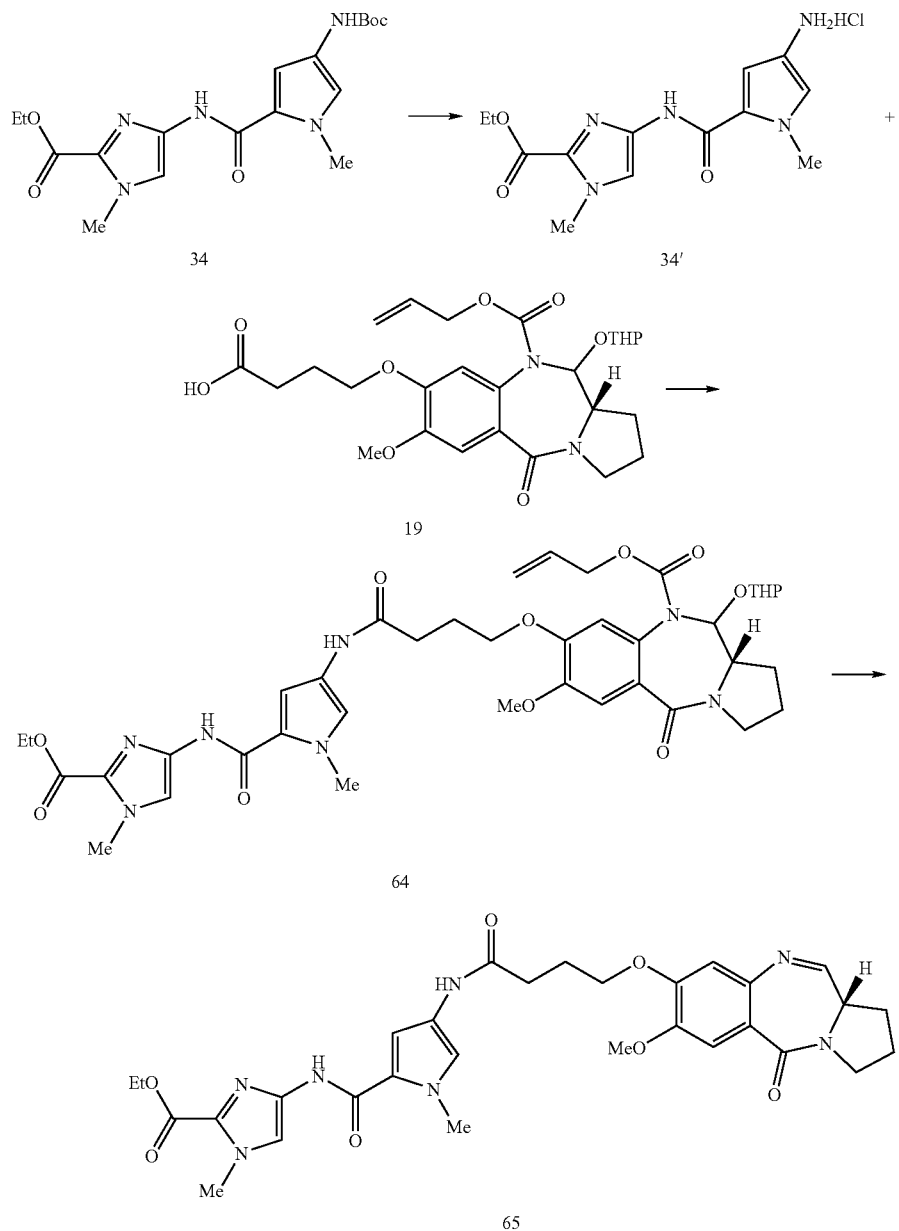

(i) The Boc imidazole-pyrrole dimer (34) (0.130 g, 0.33 mmol) was deprotected using 4M HCl in dioxane as described in general procedure C. The resulting residue (34') was dissolved in dry DCM (5 mL) and the AllocTHPPBD acid (0.172 g, 0.33 mmol) was added and reacted as described in general procedure B. This yielded a brown foam 0.220 g (84%). LCMS (method 1) rt=3.33 min; m/z (ES+) 792 (M+1).

(ii) The AllocTHPPBD-imidazole-pyrrole conjugate (64) (0.220 g, 0.28 mmol) was deprotected as described in general procedure E to yield 0.044 g (26%). $^1$H-NMR $d_6$-acetone (400 MHz) δ 9.25 (s, 1H) 9.21 (s, 1H) 7.74 (d, 1H, J=4.4 Hz) 7.57 (s, 1H) 7.41 (m, 2H) 7.08 (d, 1H, J=1.6 Hz) 6.81 (s, 1H) 4.33 (q, 2H, J=7.1 Hz) 4.14 (m, 2H) 4.01 (s, 3H) 3.94 (s, 3H) 3.87 (s, 3H) 3.69 (m, 2H) 3.46 (m, 1H) 2.55 (m, 2H) 2.36 (m, 2H) 2.17 (m, 2H) 2.09 (m, 2H) 1.37 (t, 3H, J=7.1 Hz); LCMS (method 1) rt=2.45; m/z (ES+) 606 (M+1).

Example 2g (11aS) Methyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-imidazole-2-carbonyl]-amino)-1-methyl-1H-pyrrole-2-carbonyl]-amino}-1-methyl-1H-pyrrole-2-carboxylate (67)

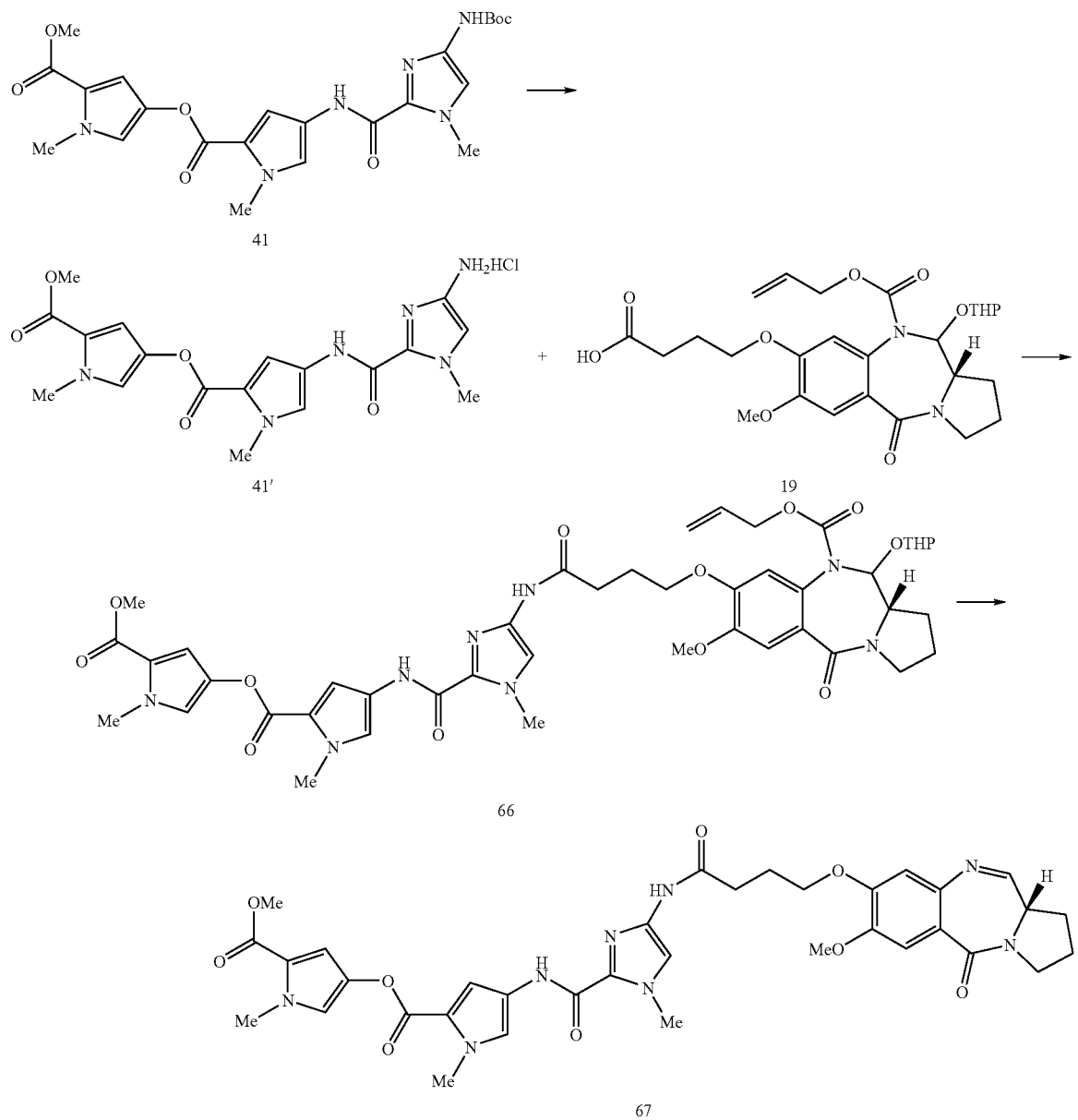

(i) The Boc pyrrole-pyrrole-imidazole trimer (41) (0.250 g, 0.50 mmol) was deprotected using 4M HCl in dioxane as described in general procedure C. The resulting residue (41') was dissolved in dry DCM (5 mL) and the AllocTHPPBD acid (19) (0.259 g, 0.50 mmol) was added and reacted as described in general procedure A. This yielded a brown foam 0.385 g (86%). LCMS (method 1) rt=3.33 min; m/z (ES+) 900 (M+1).

(ii) The AllocTHPPBD-pyrrole-pyrrole-imidazole conjugate (66) (0.200 g, 0.22 mmol) was deprotected as described in general procedure E to yield 0.045 g (29%). $^1$H-NMR $d_6$-acetone (400 MHz) δ 9.38 (s, 1H) 9.37 (s, 1H) 9.22 (s, 1H) 7.73 (d, 1H, J=4.4 Hz) 7.50 (d, 1H, J=1.9 Hz) 7.47 (s, 1H) 7.43 (s, 1H) 7.28 (d, 1H, J=1.8 Hz) 7.00 (d, 1H, J=1.8 Hz) 6.94 (d, 1H, J=2.0 Hz) 6.82 (s, 1H) 4.20 (m, 1H) 4.10 (m, 1H) 4.06 (s, 3H) 4.00 (s, 3H) 3.95 (s, 3H) 3.91 (s, 3H) 3.76 (s, 3H) 3.68 (m, 2H) 3.44 (m, 1H) 2.64 (m, 2H) 2.33 (m, 2H) 2.19 (m, 2H) 2.09 (s, 2H); LCMS (method 1) rt=2.67 min; m/z (ES+) 714 (M+1).

Example 2h (11aS) Methyl 4-({4-[4-(7-Methoxy-5-oxo-2,3,5,11a-tetrahydro-5H-pyrrolo[2,1-c][1,4]benzodiazepine-8-yloxy)-butyrylamino]-thiazole-4-carbonyl]-amino)-1-methyl-1H-pyrrole-2-carbonyl]-amino}-1-methyl-1H-pyrrole-2-carboxylate (69)

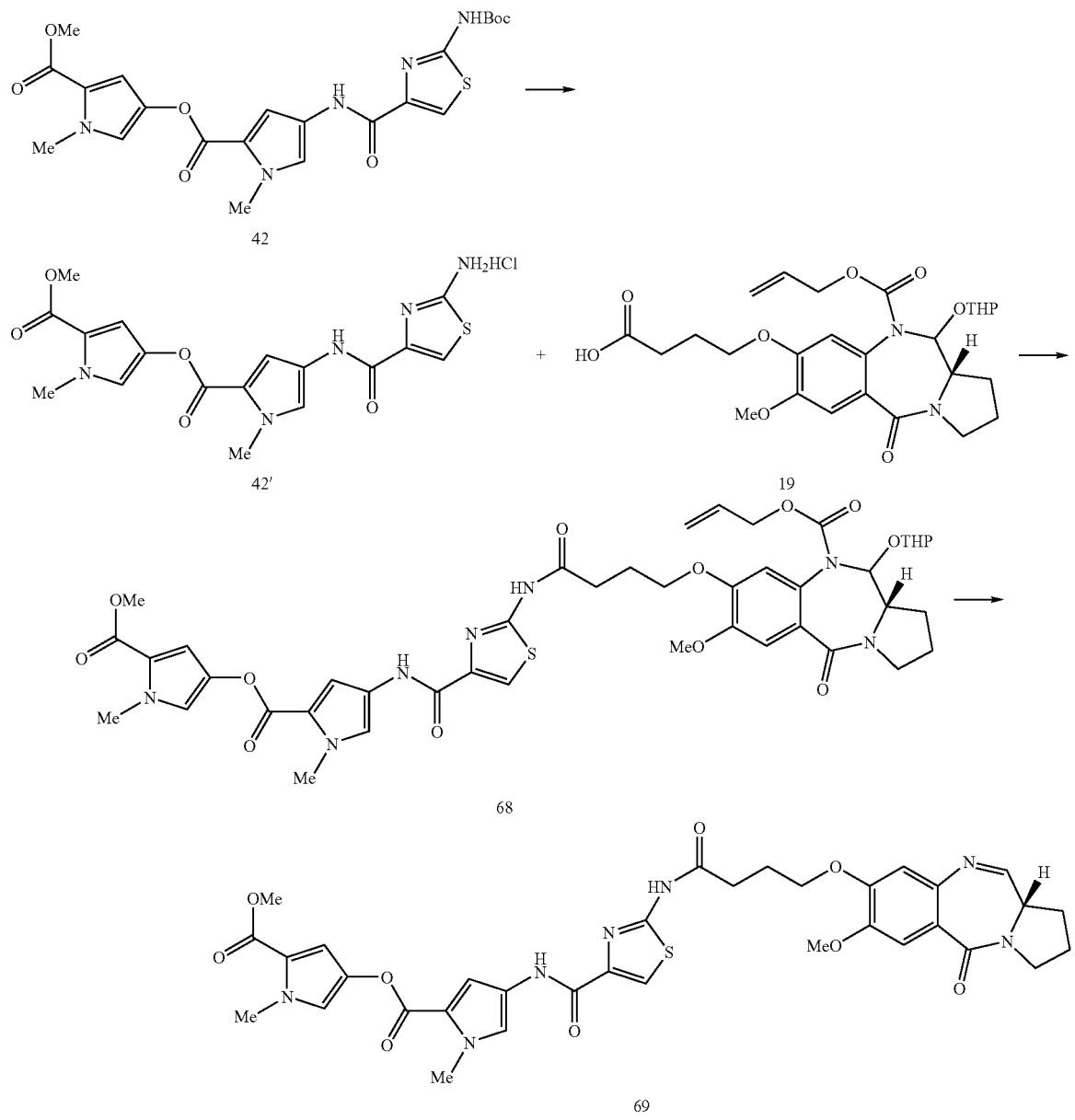

(i) The Boc pyrrole-pyrrole-thiazole trimer (42) (0.200 g, 0.40 mmol) was deprotected using 4M HCl in dioxane as described in general procedure C. The resulting residue (42') was dissolved in dry DCM (5 mL) and the AllocTHPPBD acid (19) (0.206 g, 0.40 mmol) was added and reacted as described in general procedure B. This yielded a yellow foam 0.142 g (68%). LCMS (method 2) rt=2.00 min; m/z (ES+) 521 (M+1).

(ii) The AllocTHPPBD-pyrrole-pyrrole-thiazole conjugate (68) (0.130 g, 0.14 mmol) was deprotected as described in general procedure E to yield 0.037 g (37%). $^1$H-NMR d$_6$-acetone (400 MHz) δ 11.19 (s, 1H) 9.34 (s, 1H) 9.13 (s, 1H) 7.81 (s, 1H) 7.74 (d, 1H, J=4.4 Hz) 7.50 (d, 1H, J=1.9 Hz) 7.45 (s, 1H) 7.31 (d, 1H, J=1.6 Hz) 6.99 (d, 1H, J=1.7 Hz) 6.93 (d, 1H, J=1.9 Hz) 6.82 (s, 1H) 4.14 (m, 2H) 3.94 (s, 3H) 3.91 (s, 3H) 3.84 (s, 3H) 3.76 (s, 3H) 3.68 (m, 2H) 3.44 (m, 1H) 2.34 (m, 2H) 2.27 (m, 2H) 2.21 (m, 2H) 2.09 (s, 2H); LCMS (method 1) rt=2.70 min; m/z (ES+) 717 (M+1).

Example 2i (11aS) Methyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-1-methyl-1H-imidazole-2-carbonyl]-amino}-1-methyl-1H-pyrrole-2-carboxylate (71)

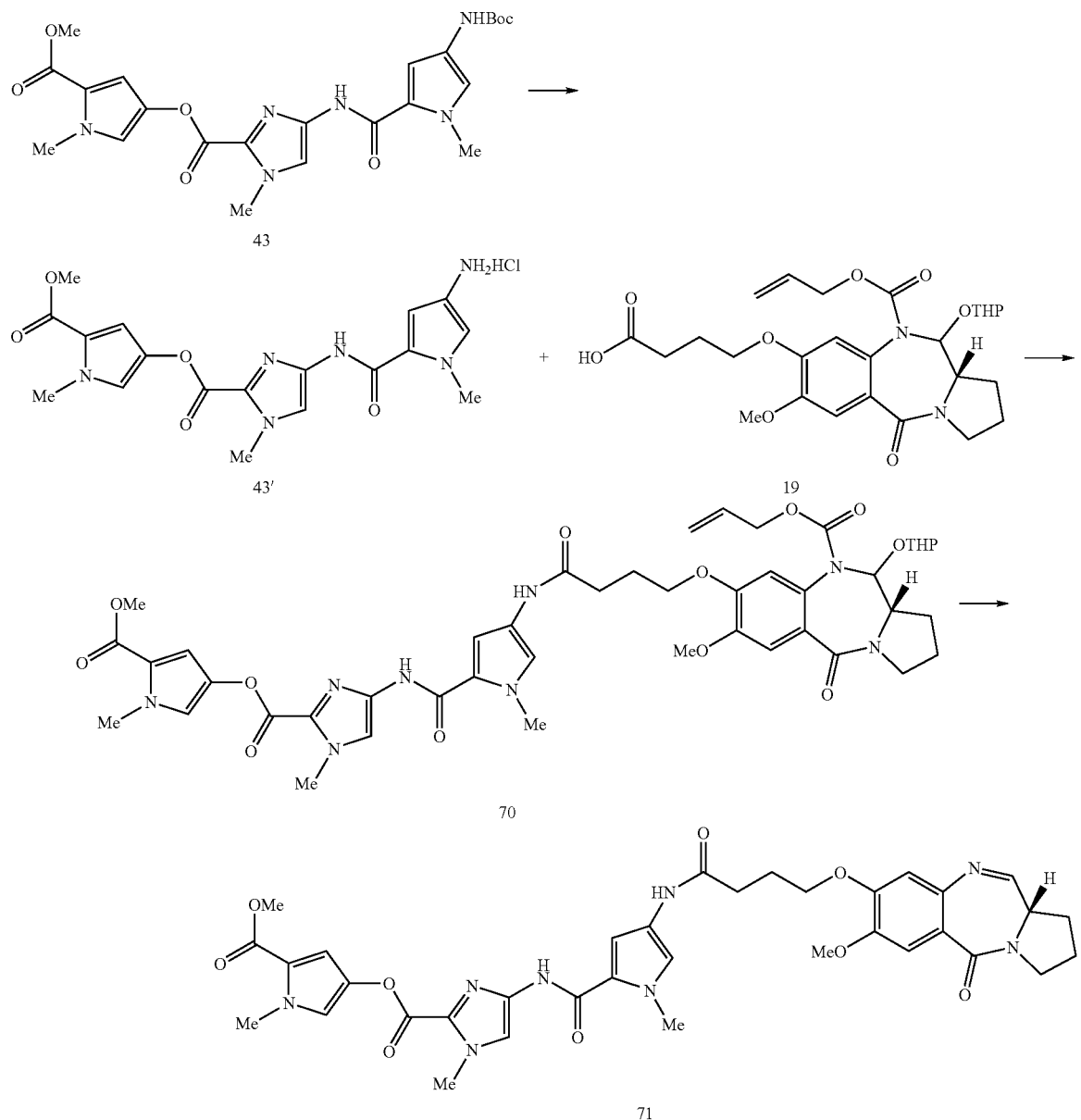

(i) The Boc pyrrole-imidazole-pyrrole trimer (43) (0.163 g, 0.33 mmol) was deprotected using 4M HCl in dioxane as described in general procedure C. The resulting residue (43') was dissolved in dry DCM (5 mL) and the AllocTHPPBD acid (19) (0.169 g, 0.33 mmol) was added and reacted as described in general procedure A. This yielded a brown foam 0.283 g (95%). LCMS (method 1) rt=3.47 min; m/z (ES+) 900 (M+1).

(ii) The AllocTHPPBD-pyrrole-imidazole-pyrrole conjugate (70) (0.260 g, 0.29 mmol) was deprotected as described in general procedure E to yield 0.034 g (16%). $^1$H-NMR $d_6$-acetone (400 MHz) δ 9.88 (s, 1H) 9.69 (s, 1H) 9.53 (s, 1H) 7.76 (d, 1H, J=4.4 Hz) 7.60 (d, 1H, J=1.1 Hz) 7.50 (s, 1H) 7.43 (s, 1H) 7.19 (d, 1H, J=2.2 Hz) 7.01 (d, 1H, J=1.5 Hz) 6.98 (d, 1H, J=1.3 Hz) 6.83 (s, 1H) 4.21 (m, 2H) 4.06 (s, 3H) 3.90 (s, 6H) 3.88 (s, 3H) 3.76 (s, 3H) 3.67 (m, 2H) 3.50 (m, 1H) 2.53 (m, 2H) 2.36 (m, 2H) 2.19 (m, 2H) 2.09 (s, 2H); LCMS (method 1) rt=2.65 min; m/z (ES+) 714 (M+1).

Example 2j (11aS) Methyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-thiazole-4-carbonyl]-amino}-1-methyl-1H-pyrrole-2-carboxylate (73)

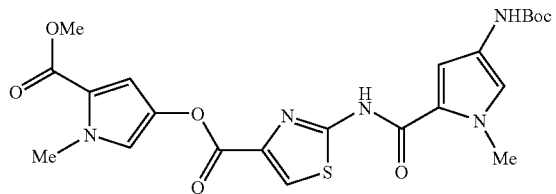

44

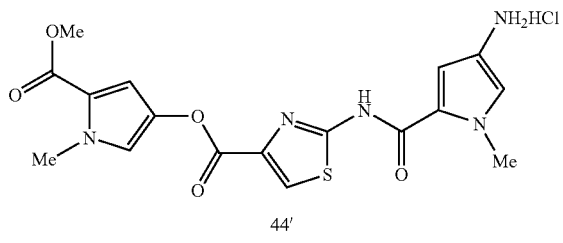 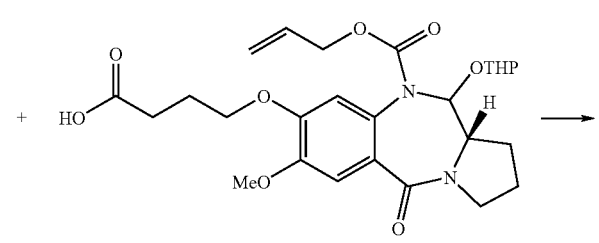

44'  19

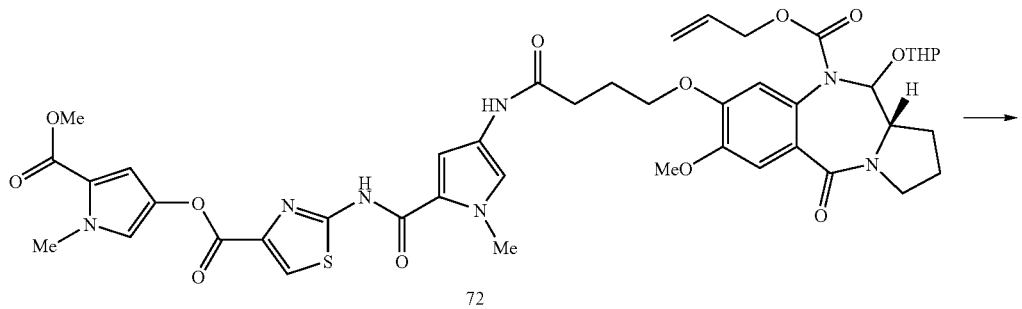

72

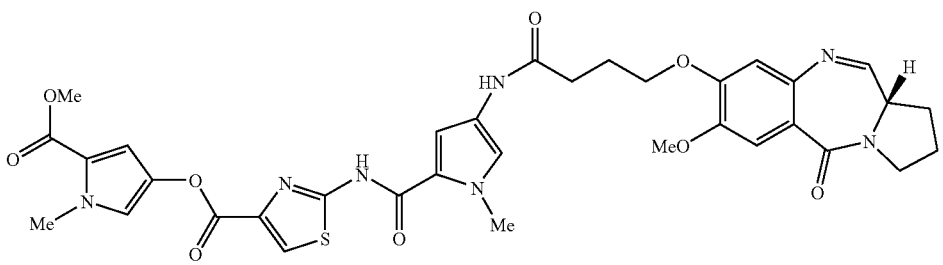

73

(i) The Boc pyrrole-thiazole-pyrrole trimer (44) (0.103 g, 0.20 mmol) was deprotected using 4M HCl in dioxane as described in general procedure C. The resulting residue (44') was dissolved in dry DCM (5 mL) and the AllocTHPPBD acid (19) (0.100 g, 0.20 mmol) was added and reacted as described in general procedure B. This yielded a yellow foam 0.135 g (75%). LCMS (method 1) rt=3.55 min; m/z (ES+) 903 (M+1).

(ii) The AllocTHPPBD-pyrrole-thiazole-pyrrole conjugate (72) (0.125 g, 0.14 mmol) was deprotected as described in general procedure E to yield 0.035 g (35%). $^1$H-NMR $d_6$-acetone (400 MHz) δ 11.07 (s, 1H) 9.25 (s, 1H) 9.23 (s, 1H) 7.81 (s, 1H) 7.75 (d, 1H, J=4.4 Hz) 7.55 (d, 1H, J=1.6 Hz) 7.45 (d, 1H, J=1.2 Hz) 7.43 (s, 1H) 7.27 (d, 1H, J=1.4 Hz) 6.98 (d, 1H, J=1.9 Hz) 6.81 (s, 1H) 4.15 (m, 2H) 3.98 (s, 3H) 3.92 (s, 3H) 3.88 (s, 3H) 3.85 (s, 3H) 3.68 (m, 1H) 3.59 (m, 1H) 3.46 (m, 1H) 2.55 (m, 2H) 2.36 (m, 2H) 2.18 (m, 2H) 2.09 (s, 2H); LCMS (method 1) rt=2.68 min; m/z (ES+) 717 (M+1).

Example 2k (11aS) Methyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-imidazole-2-carbonyl]-amino)-1-methyl-1H-imidazole-2-carbonyl]-amino}-1-methyl-1H-pyrrole-2-carboxylate (75)

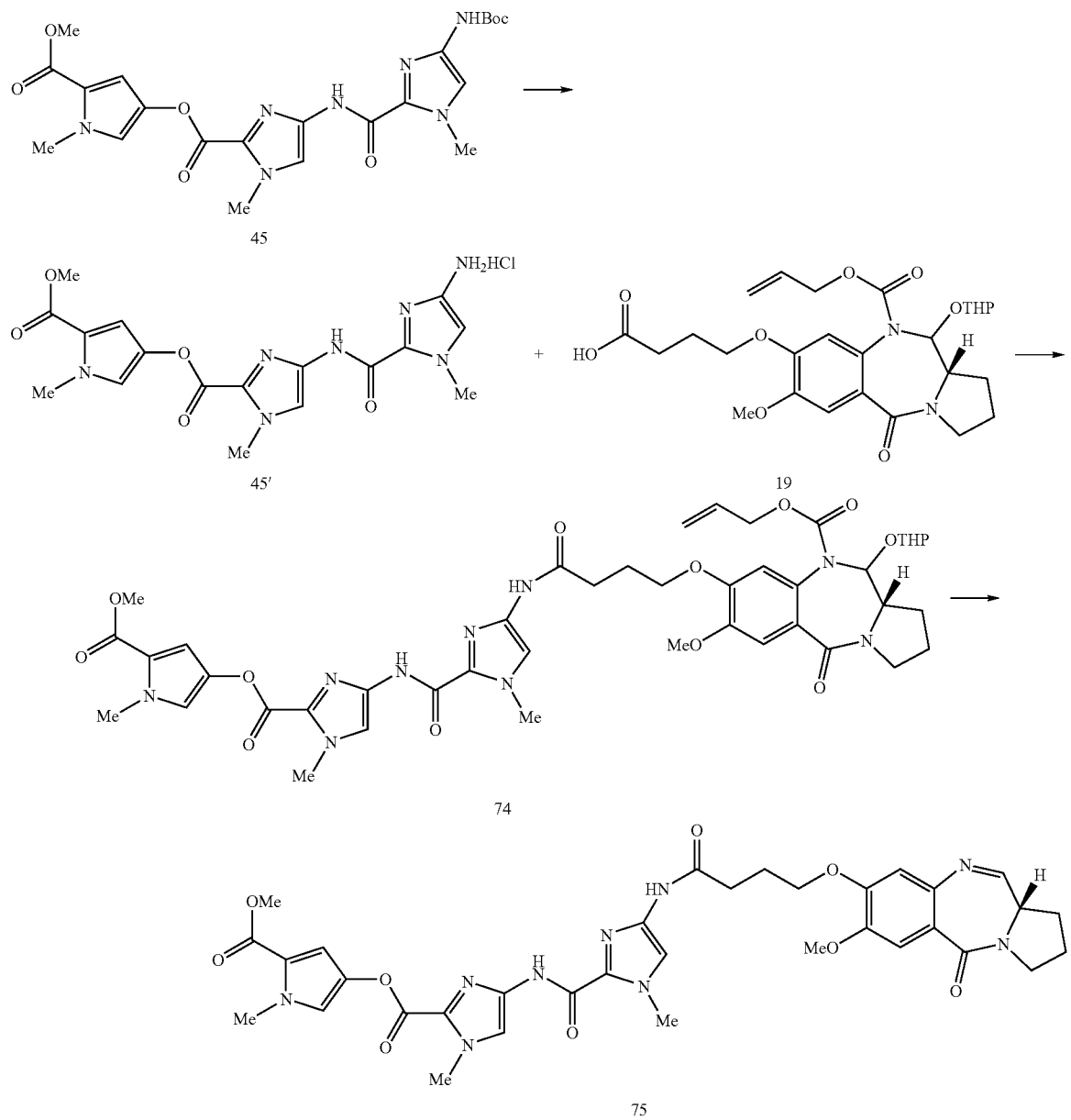

(i) The Boc pyrrole-imidazole-imidazole trimer (45) (0.060 g, 0.12 mmol) was deprotected using 4M HCl in dioxane as described in general procedure C. The resulting residue (45') was dissolved in dry DCM (5 mL) and the AllocTHPPBD acid (19) (0.063 g, 0.12 mmol) was added and reacted as described in general procedure B. This yielded a yellow foam 0.102 g (94%). LCMS (method 1) rt=3.42 min; m/z (ES+) 901 (M+1).

(ii) The AllocTHPPBD-pyrrole-imidazole-imidazole conjugate (74) (0.130 g, 0.14 mmol) was deprotected as described in general procedure E to yield 0.028 g (28%) $^1$H-NMR d$_6$-acetone (400 MHz) δ 9.71 (s, 1H) 9.42 (s, 1H) 9.05 (s, 1H) 8.02 (s, 1H) 7.73 (d, 1H, J=4.4 Hz) 7.56 (s, 1H) 7.50 (d, 1H, J=5.0 Hz) 7.42 (s, 1H) 7.18 (d, 1H, J=1.2 Hz) 6.83 (s, 1H) 4.24 (q, 2H, J=7.1 Hz) 4.10 (s, 3H) 4.07 (s, 3H) 3.94 (s, 3H) 3.92 (s, 3H) 3.78 (s, 3H) 3.67 (m, 1H) 3.52 (m, 1H) 3.39 (m, 1H) 2.52 (m, 2H) 2.31 (m, 2H) 2.21 (m, 2H) 2.09 (s, 2H); LCMS (method 1) rt=2.70 min; m/z (ES+) 715 (M+1).

Example 21

(11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-imidazole-2-carbonyl]-amino)-1-methyl-1H-imidazole-2-carbonyl]-amino}-1-methyl-1H-imidazole-2-carboxylate (77)

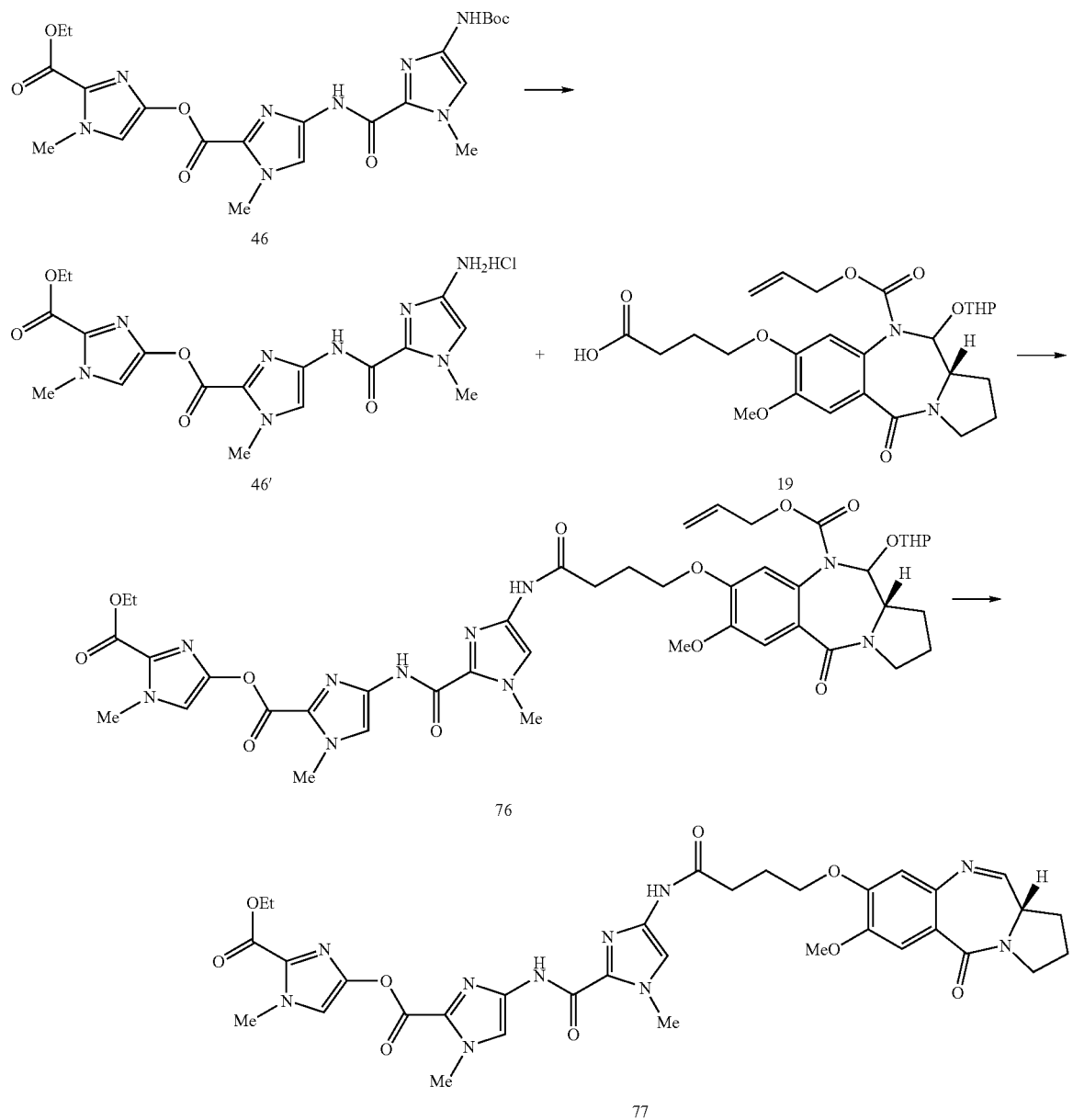

(i) The Boc imidazole trimer (46) (0.100 g, 0.19 mmol) was deprotected using 4M HCl in dioxane as described in general procedure C. The resulting residue (46') was dissolved in dry DCM (5 mL) and the AllocTHPPBD acid (19) (0.100 g, 0.19 mmol) was added and reacted as described in general procedure A. This yielded a brown foam 0.146 g (78%). LCMS (method 1) rt=3.48 min; m/z (ES+) 916 (M+1).

(ii) The AllocTHPPBD-imidazole-imidazole-imidazole conjugate (76) (0.135 g, 0.15 mmol) was deprotected as described in general procedure E to yield 0.024 g (22%). $^1$H-NMR d$_6$-DMSO (400 MHz) δ 10.53 (m, 1H) 10.16 (s, 1H) 9.54 (s, 1H) 7.78 (d, 1H, J=4.4 Hz) 7.71 (s, 1H) 7.64 (s, 1H) 7.54 (s, 1H) 7.32 (s, 1H) 6.83 (s, 1H) 4.29 (q, 2H, J=7.1 Hz) 4.16 (m, 2H) 4.00 (s, 3H) 3.98 (s, 3H) 3.95 (s, 3H) 3.82 (s, 3H) 3.67 (m, 2H) 3.59 (m, 1H) 2.42 (m, 2H) 2.33 (m, 2H) 2.04 (m, 2H) 1.93 (m, 2H) 1.31 (t, 1H, J=7.1 Hz). LCMS (method 1) rt=2.62 min; m/z (ES+) 730 (M+1).

Example 2m (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-1-methyl-1H-pyrrole-2-carbonyl]-amino}-1-methyl-1H-imidazole-2-carboxylate (79)

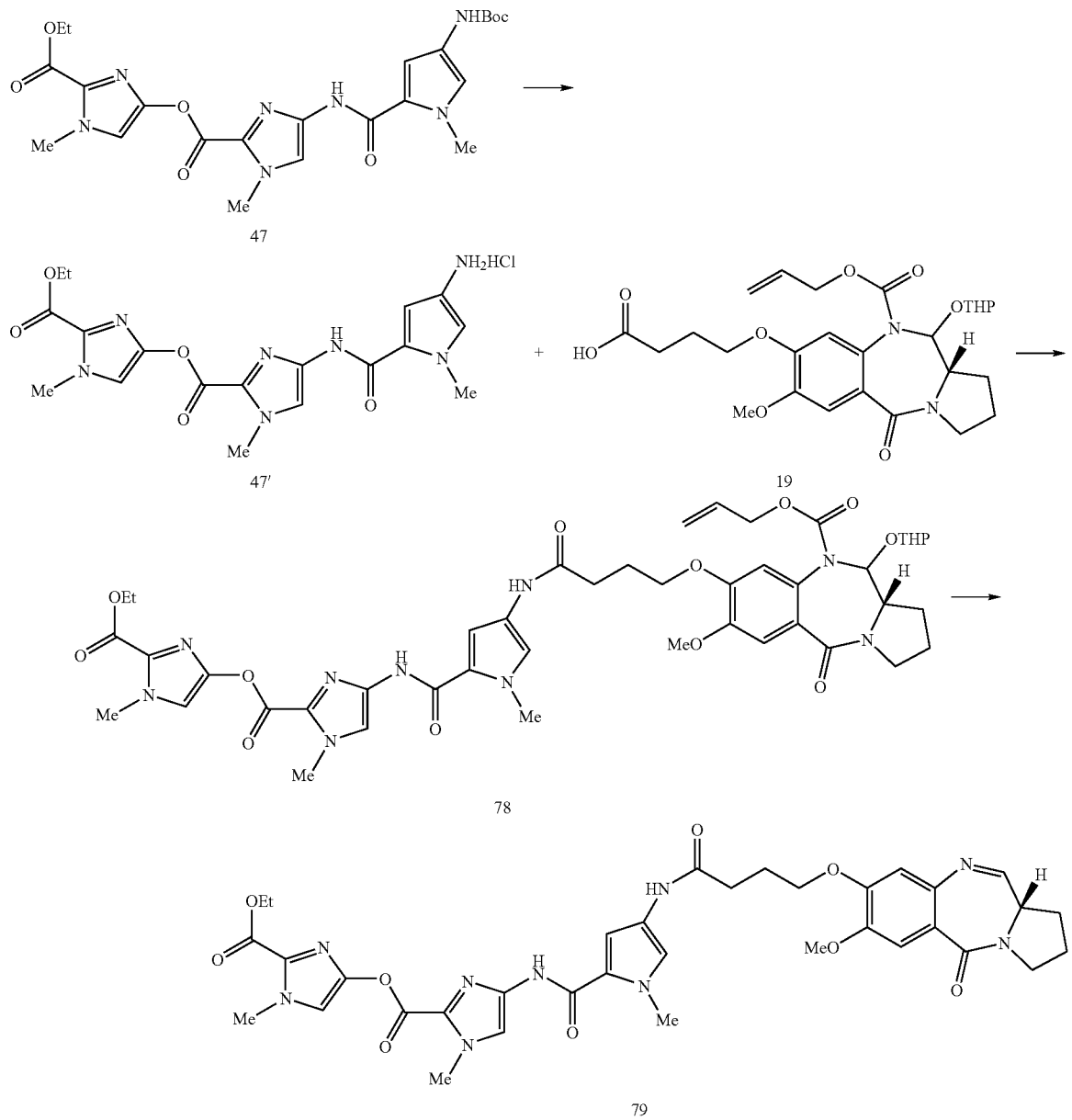

(i) The Boc imidazole-imidazole-pyrrole trimer (47) (0.100 g, 0.20 mmol) was deprotected using 4M HCl in dioxane as described in general procedure C. The resulting residue (47') was dissolved in dry DCM (5 mL) and the AllocTHPPBD acid (19) (0.101 g, 0.20 mmol) was added and reacted as described in general procedure A. This yielded a brown foam 0.158 g (86%). LCMS (method 1) rt=3.22 min; m/z (ES+) 917 (M+1).

(ii) The AllocTHPPBD-imidazole-pyrrole-pyrrole-conjugate (78) (0.210 g, 0.23 mmol) was deprotected as described in general procedure E to yield 0.028 g (17%) $^1$H-NMR d$_6$-acetone (400 MHz) δ 9.40 (s, 1H) 9.29 (s, 1H) 9.07 (s, 1H) 8.15 (s, 1H) 7.74 (d, 1H, J=4.4 Hz) 7.59 (s, 1H) 7.48 (d, 1H, J=1.6 Hz) 7.42 (d, 1H, J=2.1 Hz) 7.16 (d, 1H, J=1.6 Hz) 6.83 (d, 1H, J=1.8 Hz) 4.33 (q, 2H, J=7.1 Hz) 4.13 (m, 2H) 4.01 (s, 3H) 3.96 (s, 3H) 3.91 (s, 3H) 3.87 (s, 3H) 3.69 (m, 2H) 3.47 (m, 1H) 2.55 (m, 2H) 2.36 (m, 2H) 2.15 (m, 2H) 2.09 (m, 2H) 1.37 (t, 3H, J=7.1 Hz); LCMS (method 1) rt=2.60 min; m/z (ES+) 728 (M+1).

Example 2n (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-imidazole-2-carbonyl]-amino)-1-methyl-1H-pyrrole-2-carbonyl]-amino}-1-methyl-1H-imidazole-2-carboxylate (81)

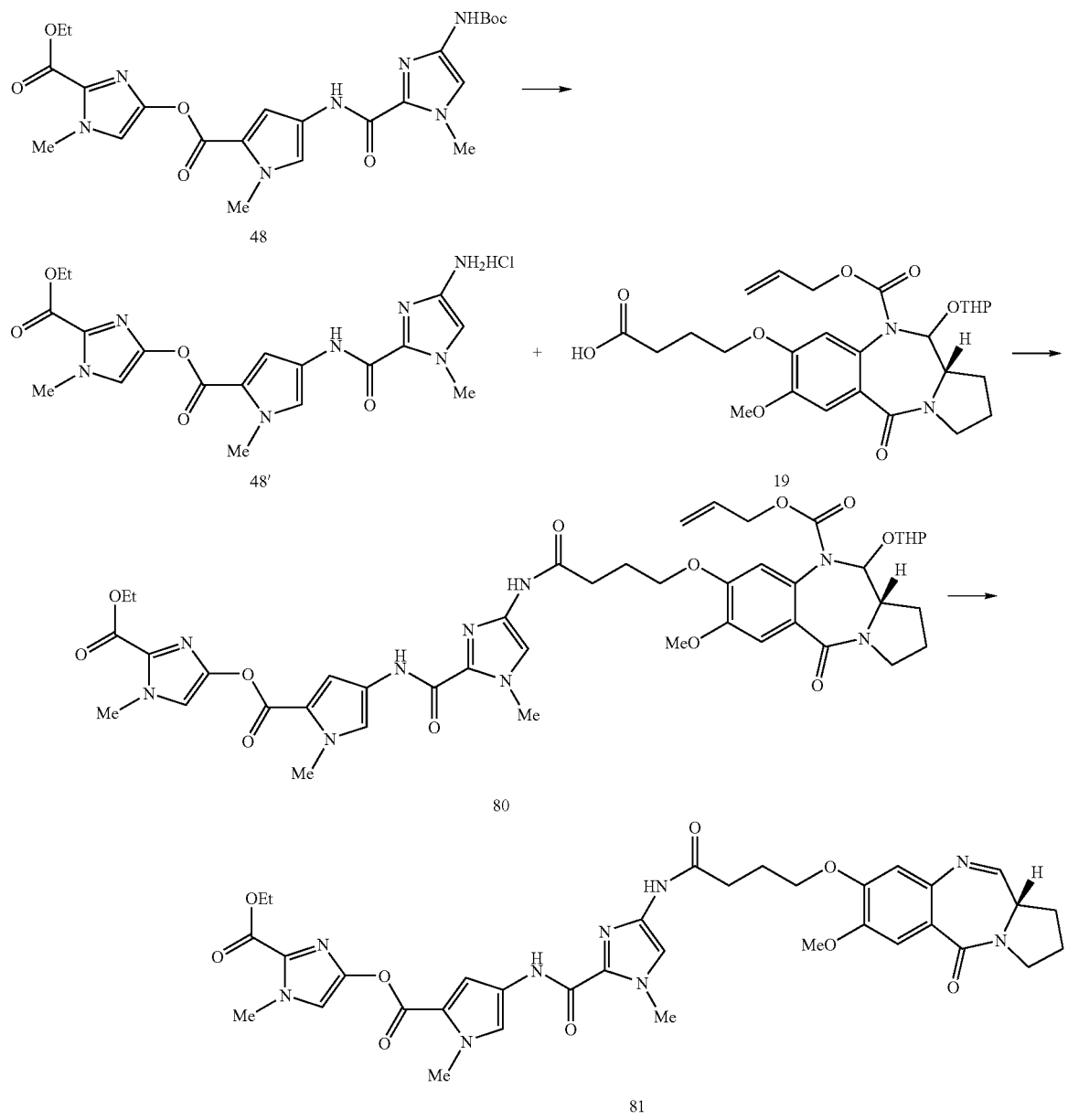

(i) The Boc imidazole-pyrrole-imidazole trimer (48) (0.100 g, 0.20 mmol) was deprotected using 4M HCl in dioxane as described in general procedure C. The resulting residue (48') was dissolved in dry DCM (5 mL) and the AllocTHPPBD acid (0.101 g, 0.20 mmol) was added and reacted as described in general procedure A. This yielded a brown foam 0.131 g (72%). LCMS (method 1) rt=3.46 min; m/z (ES+) 915 (M+1).

(ii) The AllocTHPPBD-imidazole-pyrrole-imidazole conjugate (80) (0.120 g, 0.13 mmol) was deprotected as described in general procedure E to yield 0.026 g (27%) $^1$H-NMR d$_6$-acetone (400 MHz) δ 9.52 (s, 1H) 9.42 (s, 1H) 9.27 (s, 1H) 7.74 (d, 1H, J=4.4 Hz) 7.60 (s, 1H) 7.49 (d, 1H, J=1.7 Hz) 7.44 (s, 1H) 7.42 (s, 1H) 7.27 (d, 1H, J=1.8 Hz) 6.82 (s, 1H) 4.33 (q, 2H, J=7.1 Hz) 4.16 (m, 1H) 4.06 (m, 1H) 4.02 (s, 3H) 3.98 (s, 3H) 3.88 (s, 3H) 3.80 (s, 3H,) 3.69 (m, 2H) 3.48 (m, 1H) 2.65 (m, 2H) 2.35 (m, 2H) 2.18 (m, 2H) 2.09 (s, 2H) 1.38 (t, 3H, J=7.1 Hz); LCMS (method 1) rt=2.60 min; m/z (ES+) 729 (M+1).

Example 2o (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-thiazole-4-carbonyl]-amino)-thiazole-4-carbonyl]-amino}-thiazole-4-carboxylate (83)

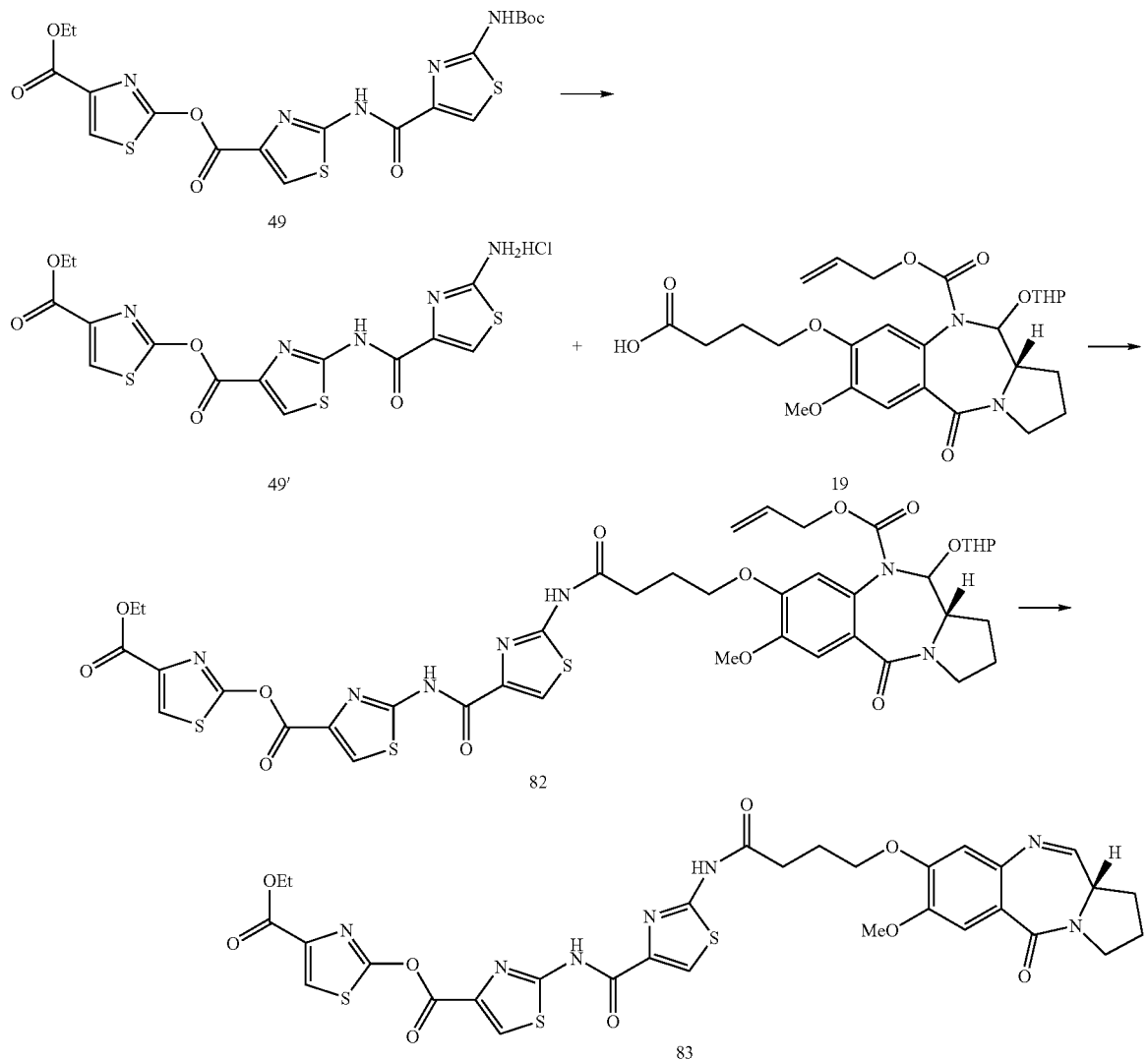

(i) The Boc thiazole trimer (49) (0.163 g, 0.31 mmol) was deprotected using 4M HCl in dioxane as described in general procedure C. LCMS analysis showed partial Boc deprotection, therefore the mixture was treated with DCM:TFA:H$_2$O (50%:47.5%:2.5%) and allowed to stir for 2 hours at room temperature. The reaction mixture was concentrated in vacuo and DCM (20 mL) was added. The solution was washed with saturated NaHCO$_3$ solution (3×30 mL). The combined aqueous layers were filtered to collect the precipitated thiazole amine (49'), which was washed with deionised water then dried under vacuum. The organic layers were combined and dried using MgSO$_4$. Concentration in vacuo afforded further amine which was dried under vacuum. The aqueous layer was filtered under vacuum to remove a precipitate, the thiazole trimer amine, as identified by LCMS. The thiazole trimer amine was dissolved in dry DCM (5 mL) and DMF (1 mL). The AllocTHPPBD acid (19) (0.161 g, 0.31 mmol) was added and reacted as described in general procedure B. This yielded a brown oil 0.208 g (73%). LCMS (method 1) rt=3.92 min; m/z (ES+) 925 (M+1).

(ii) The AllocTHPPBD-thiazole-thiazole-thiazole conjugate (82) (0.208 g, 0.23 mmol) was deprotected as described in general procedure E to yield 0.020 g (12%). $^1$H-NMR d$_6$-acetone (400 MHz) δ 11.09 (s, 1H) 9.73 (s, 1H) 9.57 (s, 1H) 8.12 (s, 1H) 8.05 (s, 1H) 7.72 (d, 1H, J=4.4 Hz) 7.68 (s, 1H) 7.41 (s, 1H) 6.96 (s, 1H) 4.34 (q, 2H, J=7.1 Hz) 4.08 (m, 1H) 3.93 (m, 1H) 3.87 (s, 3H) 3.78 (m, 1H) 3.54 (m, 1H) 3.44 (m, 1H) 2.52 (m, 2H) 2.36 (m, 2H) 2.21 (m, 2H) 2.09 (m, 2H) 1.36 (t, 1H, J=7.1 Hz); LCMS (method 1) rt=2.98 min; m/z (ES+) 739 (M+1).

Example 2p (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-thiazole-4-carbonyl]-amino}-thiazole-4-carboxylate (85)

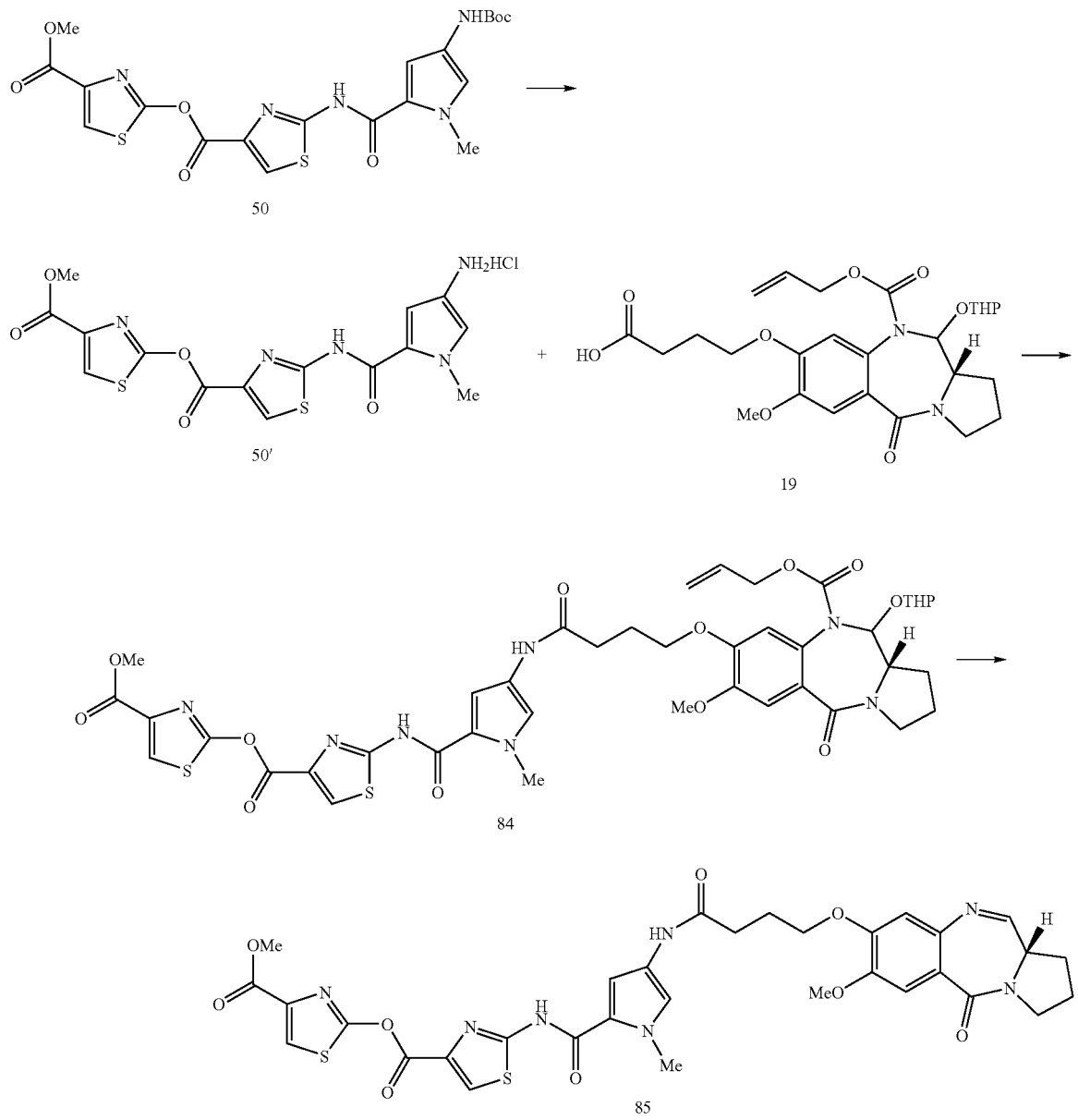

(i) The Boc thiazole-thiazole-pyrrole trimer (50) (0.100 g, 0.19 mmol) was deprotected using 4M HCl in dioxane as described in general procedure C. The resulting residue (50') was dissolved in dry DCM (5 mL) and the AllocTHPPBD acid (19) (0.099 g, 0.19 mmol) was added and reacted as described in general procedure B. This yielded a brown foam 0.160 g, (91%). LCMS (method 1) rt=3.62 min; m/z (ES+) 921 (M+1).

(ii) The AllocTHPPBD-thiazole-thiazole-pyrrole conjugate (84) (0.090 g, 0.10 mmol) was deprotected as described in general procedure E to yield 0.006 g (8%). $^1$H-NMR $d_6$-acetone (400 MHz) δ 9.28 (s, 2H) 8.23 (s, 1H) 8.09 (s, 1H) 8.04 (s, 1H) 7.75 (d, 1H, J=4.4 Hz) 7.50 (d, 1H, J=1.8 Hz) 7.42 (s, 1H) 7.29 (d, 1H, J=1.5 Hz) 6.82 (s, 1H) 4.34 (q, 2H, J=7.1 Hz) 4.16 (m, 2H) 4.00 (s, 3H) 3.88 (s, 3H) 3.71 (m, 1H) 3.59 (m, 1H) 3.46 (m, 1H) 2.56 (m, 2H) 2.36 (m, 2H,) 2.20 (m, 2H) 2.09 (m, 2H) 1.37 (t, 3H, J=7.1 Hz); LCMS (method 1) rt=2.95 min; m/z (ES+) 735 (M+1).

Example 2q (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-thiazole-4-carbonyl]-amino)-1-methyl-1H-pyrrole-2-carbonyl]-amino}-thiazole-4-carboxylate (87)

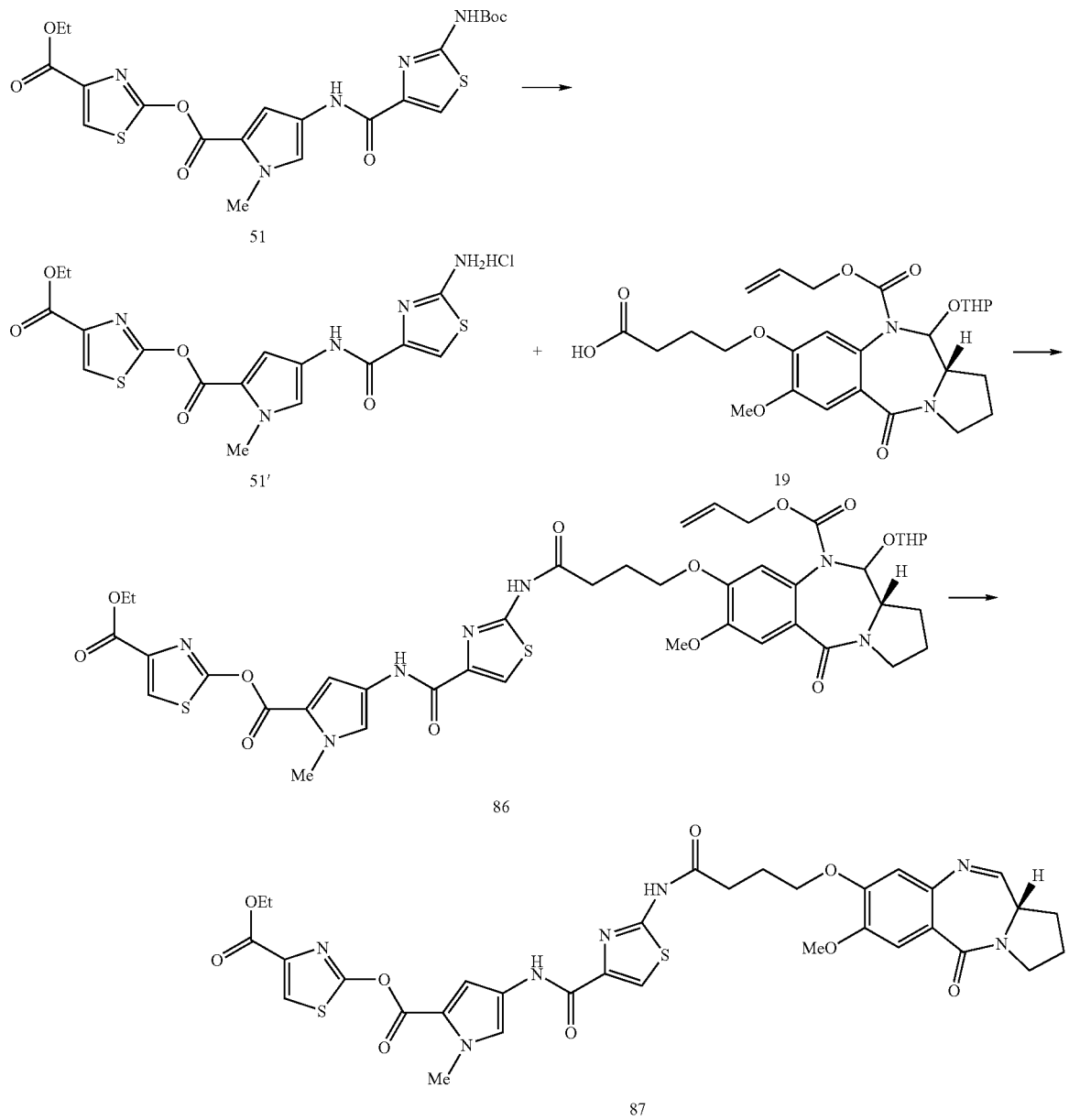

(i) The Boc thiazole-pyrrole-thiazole trimer (51) (0.100 g, 0.19 mmol) was deprotected using 4M HCl in dioxane as described in general procedure C. The resulting residue (51') was dissolved in dry DCM (5 mL) and the AllocTHPPBD acid (19) (0.100 g, 0.19 mmol) was added and reacted as described in general procedure B. This yielded a yellow foam 0.148 g (84%). LCMS (method 1) rt=3.65 min; m/z (ES+/−) 921 (M+1).

(ii) The AllocTHPPBD-thiazole-pyrrole-thiazole conjugate (86) (0.140 g, 0.16 mmol) was deprotected as described in general procedure E to yield 0.009 g (8%). $^1$H-NMR d$_6$-acetone (400 MHz) δ 11.28 (s, 1H) 10.95 (s, 1H) 9.30 (s, 1H) 7.95 (s, 1H) 7.84 (s, 1H) 7.75 (d, 1H, J=4.4 Hz) 7.66 (d, 1H, J=1.7 Hz) 7.50 (d, 1H, J=1.8 Hz) 7.43 (s, 1H) 6.83 (s, 1H) 4.33 (q, 2H, J=7.1 Hz) 4.21 (m, 2H) 4.03 (s, 3H) 3.87 (m, 3H) 3.70 (m, 1H) 3.58 (m, 1H) 3.50 (m, 1H) 2.53 (m, 2H) 2.36 (m, 2H) 2.23 (m, 2H) 2.09 (m, 2H) 1.36 (t, 3H, J=7.1 Hz); LCMS (method 1) rt=2.88 min; m/z (ES+) 735 (M+1).

Example 2r (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-1-methyl-1H-pyrrole-2-carbonyl]-amino}-thiazole-4-carboxylate (89)

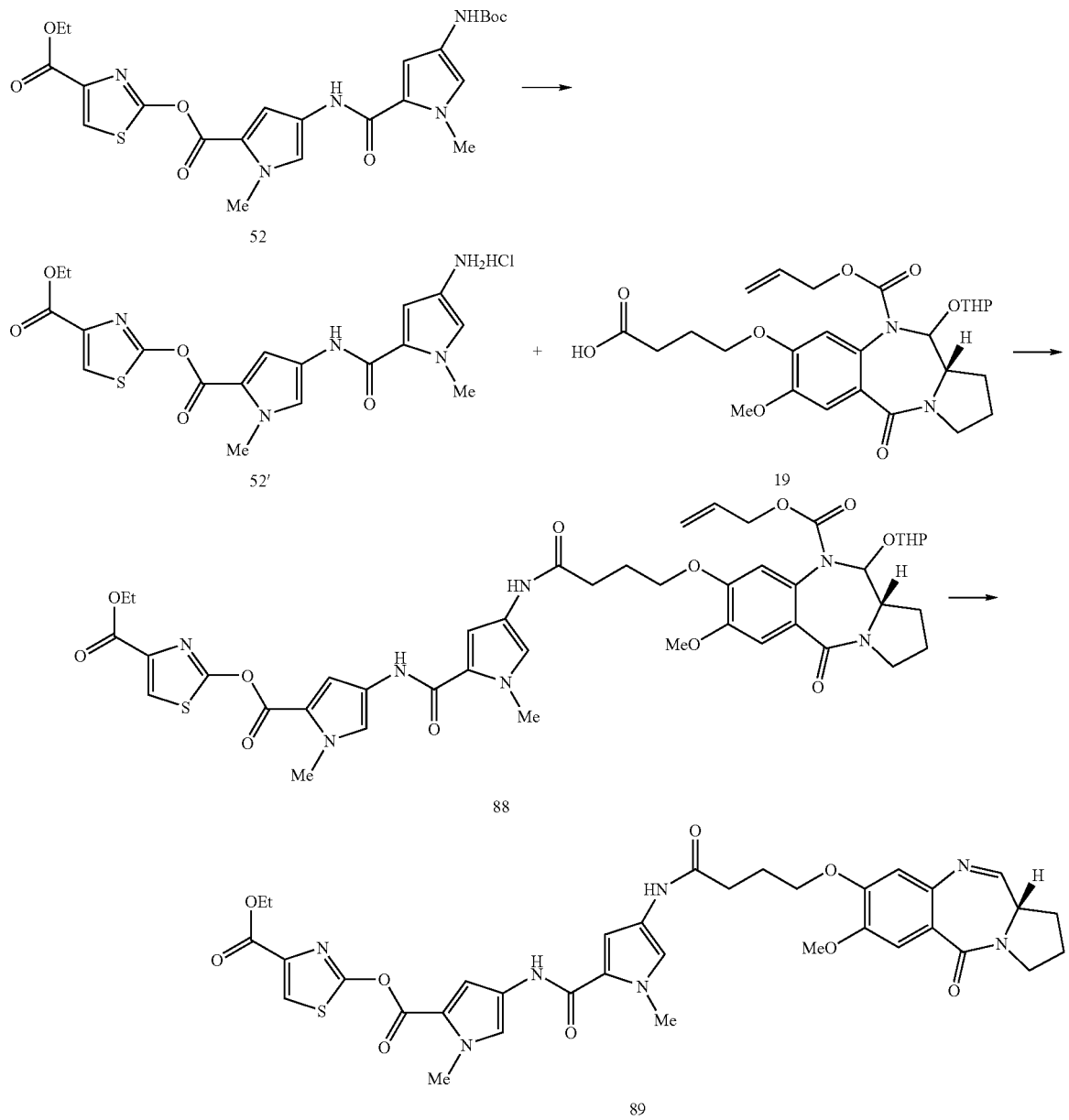

(i) The Boc thiazole-pyrrole-pyrrole trimer (52) (0.165 g, 0.32 mmol) was deprotected using 4M HCl in dioxane as described in general procedure C. The resulting residue (52') was dissolved in dry DCM (5 mL) and the AllocTHPPBD acid (19) (0.166 g, 0.32 mmol) was added and reacted as described in general procedure B. This yielded an orange foam 0.225 g (77%). LCMS (method 1) rt=3.67 min; m/z (ES+) 917 (M+1).

(ii) The AllocTHPPBD-thiazole-pyrrole-pyrrole conjugate (88) (0.200 g, 0.22 mmol) was deprotected as described in general procedure E to yield 0.009 g (6%) $^1$H-NMR $d_6$-acetone (400 MHz) δ 10.88 (s, 1H) 9.46 (s, 1H) 9.07 (s, 1H) 7.93 (s, 1H) 7.75 (d, 1H, J=4.4 Hz) 7.61 (d, 1H, J=1.6 Hz) 7.43 (d, 2H, J=2.3 Hz) 7.16 (d, 1H, J=1.7 Hz) 6.85 (d, 1H, J=1.8 Hz) 6.81 (s, 1H) 4.32 (q, 2H, J=7.1 Hz) 4.14 (m, 2H) 4.02 (s, 3H) 3.99 (s, 3H) 3.92 (s, 3H) 3.69 (m, 2H) 3.47 (m, 1H) 2.54 (m, 2H) 2.36 (m, 2H) 2.21 (m, 2H) 2.09 (s, 2H) 1.36 (t, 3H, J=7.1 Hz); LCMS (method 1) rt=2.85 min; m/z (ES+) 731 (M+1).

Example 2t (11aS) Ethyl 4-({4-[4-(7-Methoxy-5-oxo-2,3,5,11a-tetrahydro-5H-pyrrolo[2,1-c][1,4]benzodiazepine-8-yloxy)-butyrylamino]-1-methyl-1H-pyrrole-2-carbonyl]-amino)-1-methyl-1H-imidazole-2-carbonyl]-amino}-1-methyl-1H-imidazole-2-carboxylate (91)

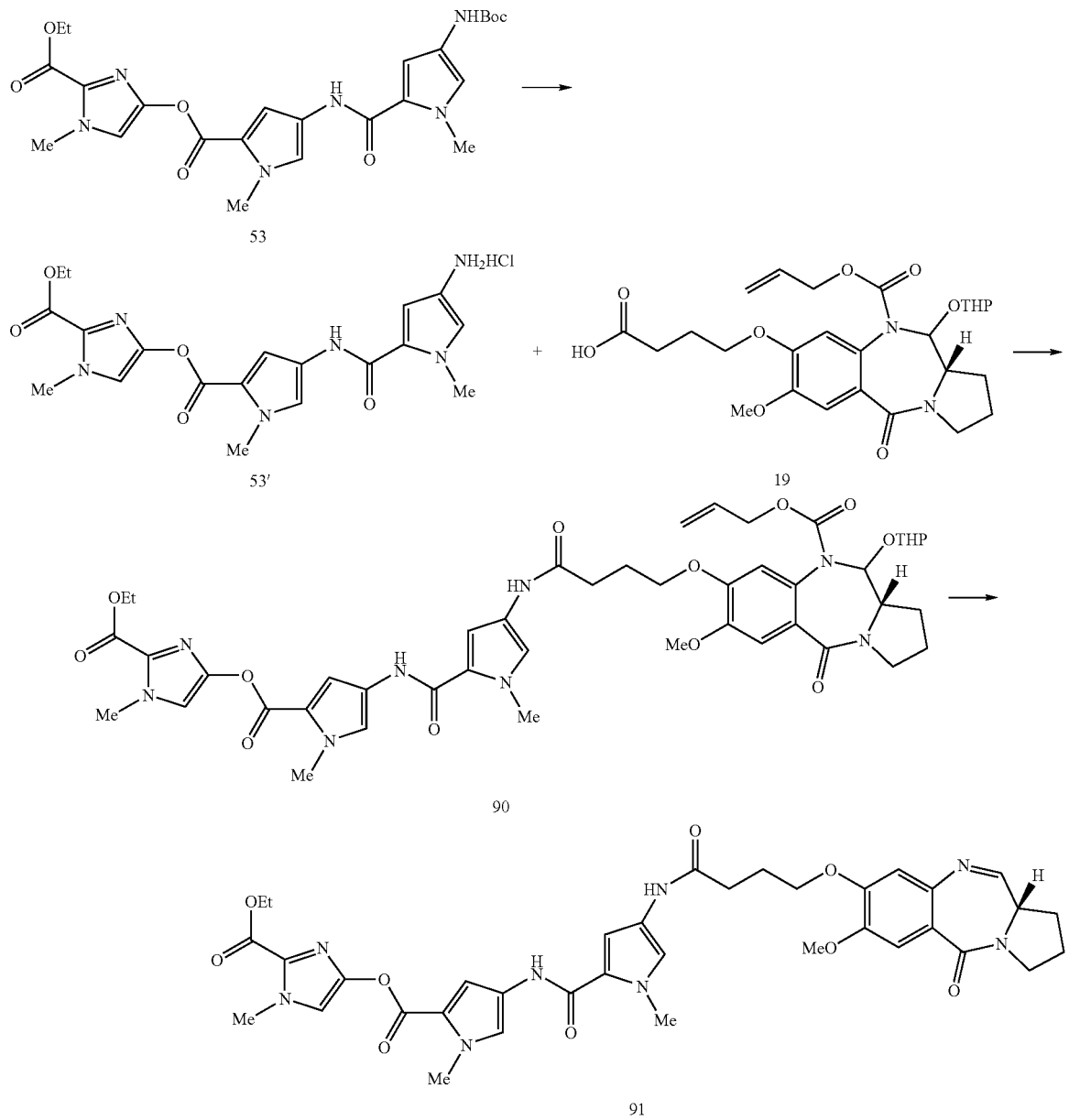

(i) The Boc imidazole-pyrrole-pyrrole trimer (53) (0.150 g, 0.29 mmol) was deprotected using 4M HCl in dioxane as described in general procedure C. The resulting residue (53') was dissolved in dry DCM (5 mL) and the AllocTHPPBD acid (19) (0.151 g, 0.29 mmol) was added and reacted as described in general procedure A. This yielded a brown foam (0.253 g, 95%). LCMS (method 1) rt=3.33 min; m/z (ES+) 914 (M+1).

(ii) The AllocTHPPBD-imidazole-imidazole-pyrrole conjugate (90) (0.145 g, 0.16 mmol) was deprotected as described in general procedure E to yield 0.016 g (14%). $^1$H-NMR $d_6$-acetone (400 MHz) δ 9.46 (s, 1H) 9.29 (s, 1H) 9.19 (s, 1H) 7.75 (d, 1H, J=4.4 Hz) 7.59 (s, 1H) 7.58 (s, 1H) 7.42 (s, 1H) 7.36 (d, 1H, J=1.7 Hz) 6.99 (d, 1H, J=1.7 Hz) 6.81 (s, 1H) 4.34 (m, 2H) 4.15 (m, 2H) 4.10 (s, 3H) 4.04 (s, 3H) 3.94 (s, 3H) 3.87 (s, 3H) 3.68 (m, 1H) 3.58 (m, 1H) 3.46 (m, 1H) 2.54 (m, 2H) 2.36 (m, 2H) 2.21 (m, 2H) 2.09 (m, 2H) 1.36 (t, 3H, J=7.1 Hz); LCMS (method 1) rt=2.62 min; m/z (ES+) 729 (M+1).

Example 3

Thermal Denaturation Studies

The PBD agents were subjected to DNA thermal melting (denaturation) studies (Gregson, S. J., et al., *Journal of Medicinal Chemistry*, 44(5), 737-748 (2001); Jones, G. B., et al., *Anti-Cancer Drug Design*, 5(3), 249-264 (1990); McConnaughie, A. W. and; Jenkins, T. C. *Journal of Medicinal Chemistry*, 38(18), 3488-3501 (1995)) using calf thymus DNA (CT-DNA, type-1, highly polymerized sodium salt; 42% G+C [Sigma]) at a fixed 100 µM (DNAp=50 µM bp) concentration, determined using an extinction coefficient of 6600 (M phosphate)$^{-1}$ cm$^{-1}$ at 260 nm (Manzini, G., et al., *Nucleic Acids Research*, 11(24), 8861-8876 (1983)). Solutions were prepared in pH 7.00±0.01 aqueous buffer containing 10 mM NaH$_2$PO$_4$/Na$_2$HPO$_4$ and 1 mM EDTA. Working solutions containing CT-DNA and the test compound (20 µM) were incubated at 37.0±0.1° C. for 0 to 18 hours using an external water bath. Samples were monitored at 260 nm using a Varian-Cary 400 Bio spectrophotometer fitted with a Peltier heating accessory. Heating was applied at a rate of 1° C./min in the 45 to 98° C. temperature range, with optical and temperature data sampling at 200 ms intervals. A separate experiment was carried out using buffer alone, and this baseline was subtracted from each DNA melting curve before data treatment. Optical data were imported into the Origin 5 program (MicroCal Inc., Northampton, Mass.) for analysis. DNA helix→coil transition temperatures ($T_m$) were determined at the midpoint of the normalized melting profiles using a published analytical procedure (Jones, G. B., et al., *Anti-Cancer Drug Design*, 5(3), 249-264 (1990)). Results are given in table 1 as the mean±standard deviation from at least three determinations. Ligand-induced alterations in DNA melting behaviour ($\Delta T_m$) are given by $\Delta T_m = T_m(\text{DNA+ligand}) - T_m(\text{DNA})$, where the $T_m$ value determined for free CT-DNA is 67.82±0.06° C. (averaged from >90 runs). All PBD compounds were dissolved in HPLC-grade MeOH to give working solutions containing ≤0.6% v/v MeOH; $T_m$ results were corrected for the effects of MeOH co-solvent by using a linear correction term. Other [DNAp]/[ligand] molar ratios (i.e., 50:1 and 100:1) were examined in the case of the PBD dimers to ensure that the fixed 5:1 ratio used in this assay did not result in saturation of the host DNA duplex.

| Compound | Induced $\Delta T_m$ (° C.) after incubation | | |
|---|---|---|---|
| | 0 hours | 4 hours | 18 hours |
| C11 | 7.9 | 8.4 | 9.6 |
| 21 | 6.5 | 7.9 | 8.1 |
| 23 | 13.9 | 15.0 | 15.6 |
| 25 | 17.3 | 19.6 | 21.2$^x$ |
| 27 | 16.0 | 18.5 | 19.0$^y$ |
| 29 | 15.1 | 15.9 | 17.1 |
| 31 | 12.6 | 13.7 | 14.1 |

$^x$Value of 21.5° C. determined after incubation for 72 hours
$^y$Value of 19.2° C. determined after incubation for 72 hours As can be seen in table 1, compound 25 with a four-carbon linker of the invention shows superiority over compound C11 with a three-carbon linker. The Tm values for conjugate 25 of 17.3, 19.6 and 21.2° C. (for 0, 4 and 18 hours incubation) are more than double that for C11 (7.9, 8.4 and 9.6° C.) indicating that the molecule has both a higher rate of covalent binding to DNA and an overall greater stabilising effect on the duplex. It is noteworthy that the increasing Tm values for both molecules upon incubation (as is the case for the other conjugates (21, 23, 27, 29 and 31) are indicative of covalent DNA interaction as expected of any molecule containing a PBD unit. Taken together, but without wishing to be bound by theory, these results suggest that in the case of 25 versus C11, whether the linker is a three-carbon or four-carbon unit, the molecules are still binding covalently but the four-carbon linker of 25 allows a better fit in the DNA minor groove.

The above method was also carried out on the compounds of example 2, with all compounds being incubated for up to 72 hours.

| Compound | Induced $\Delta T_m$ (° C.) after incubation | | | |
|---|---|---|---|---|
| | 0 hours | 4 hours | 18 hours | 72 hours |
| 55 | 14.5 | 15.2 | 15.8 | 16.1 |
| 57 | 2.8 | 3.0 | 3.1 | 3.2 |
| 59 | 10.3 | 10.9 | 11.4 | 11.4 |
| 61 | 7.7 | 8.0 | 8.3 | 8.4 |
| 63 | 9.3 | 9.6 | 10.2 | 10.5 |
| 65 | 10.0 | 10.7 | 11.2 | 11.3 |
| 67 | 19.1 | 19.8 | 21.1 | 21.6 |
| 69 | 16.4 | 17.4 | 18.2 | 18.5 |
| 71 | 15.5 | 16.0 | 16.9 | 17.2 |
| 73 | 18.5 | 19.9 | 20.7 | 20.9 |
| 75 | 14.3 | 15.0 | 15.4 | 15.6 |
| 77 | 11.0 | 11.7 | 12.0 | 12.1 |
| 79 | 13.9 | 14.8 | 15.2 | 15.5 |
| 81 | 14.9 | 15.7 | 16.2 | 16.4 |
| 83 | 10.0 | 10.7 | 10.9 | 11.0 |
| 85 | 7.5 | 8.0 | 8.4 | 8.4 |
| 87 | 6.4 | 6.8 | 7.1 | 7.3 |
| 89 | 16.8 | 17.7 | 18.6 | 18.8 |
| 91 | 16.8 | 17.6 | 18.7 | 18.8 |

Example 4

DNA Footprinting

The sequence selectivity of the six PBD-pyrrole conjugates (21, 23, 25, 27, 29) was evaluated by standard DNA footprinting on a fragment of MS2 as follows, in accordance with the technique described in Martin, C., et al., (Martin, C., et al., *Biochemistry*, 44(11), 4135-4147 (2005))

Forward (5'-CAGGAAACAGCTATGAC-3') or reverse (5'-GTAAAACGACGGCCAGT-3') primer was 5'-end labelled with $^{32}$P by T4 polynucleotide kinase. Labelling mixture contained primer (5 pmol; Sigma-Genosys), 10× kinase buffer (1 µl; Promega), (γ-$^{32}$P)-ATP (2µ of 10 µCi/µl, 6000 Ci/mmol; Perkin Elmer Life Sciences), and T4 polynucleotide kinase (10 U; Promega) in a 10 µl final volume. Labelling mix was incubated at 37° C. for 30 minutes followed by inactivation of the kinase at 70° C. for 10 minutes. A 262 bp DNA fragment (MS2F or MS2R) was amplified from the MS2 plasmid using PCR with either labelled forward or reverse primer and the unlabelled primer as required. Reactions were comprised of labelled primer mix (10 µl), 10×PCR buffer (5 µl; Sigma), dNTPs (5 µl; 2.5 mM each of A, C, G and T, Amersham Pharmacia), unlabelled primer as required (5 µmol), MS2 plasmid template DNA (10 ng) and Taq DNA polymerase (5 U; Sigma) in a 50 µl final volume.

Radiolabelled 262-mer was purified by non-denaturing polyacrylamide gel electrophoresis, elution, filtration and EtOH precipitation and was resuspended in a solution of Tris-HCl (10 mM) pH 7.4/NaCl (10 mM) to yield an activity of 200 counts per second per 5 µl when held up, in a pipette tip, to a capped Morgan series 900 mini-monitor.

For DNase I footprinting radiolabelled 262-mer (2 µl) was incubated overnight (16-18 h) with drug solution (388 µl) or in an aqueous buffer [HEPES (20 mM) pH 7.9, NaCl (50 mM), $MgCl_2$ (1 mM), DTT (5 mM), 10% glycerol] in control reactions. Enzymatic cleavage was initiated by addition of DNase I solution (10 µl of 0.05 U/ml; Sigma) in aqueous NaCl (200 mM), $MgCl_2$ (20 mM) and $MnCl_2$ (20 mM) and halted with stop solution [40 µl of NaCl (2.25 M), EDTA (150 mM) pH 8.0, 0.57 µg/µl glycogen (0.57 µg/µl; Roche), poly (dI-dC).poly(dI-dC) DNA (19.3 ng/µl; Amersham Pharmacia)]. From this mixture, digested DNA fragments were prepared for electrophoresis following the protocol of Trauger & Dervan, and were loaded on to a preheated 8% denaturing polyacrylamide gel. Electrophoresis in 1×TBE buffer was allowed to proceed for 100 min at 70 W (1600-2000 V). The gel was the fixed in acetic acid (10% v/v) and methanol (10% v/v) for 15 minutes followed by being blotted onto Whatman 3 mM paper and vacuum-dried at 80° C. for 45 minutes.

Dried gels were stored at room temperature in phosphor storage screens (Molecular Dynamics) for a minimum period of 12 h. Data were collected from exposed screens using a Molecular Dynamics 425E PhosphorImager and transferred to ImageQuant v1.2 software (Molecular Dynamics) for analysis. Data were expressed as the differential cleavage between control and sample lanes. Peaks were integrated and differential cleavage calculated as $\ln(f_d)-\ln(f_c)$; ($f_d$ is the fractional cleavage at any particular bond in the presence of drug and $f_c$ is the fractional cleavage of the same bond in the control). Maxam-Gilbert G+A marker lanes were prepared in the usual fashion.

Figure 2:
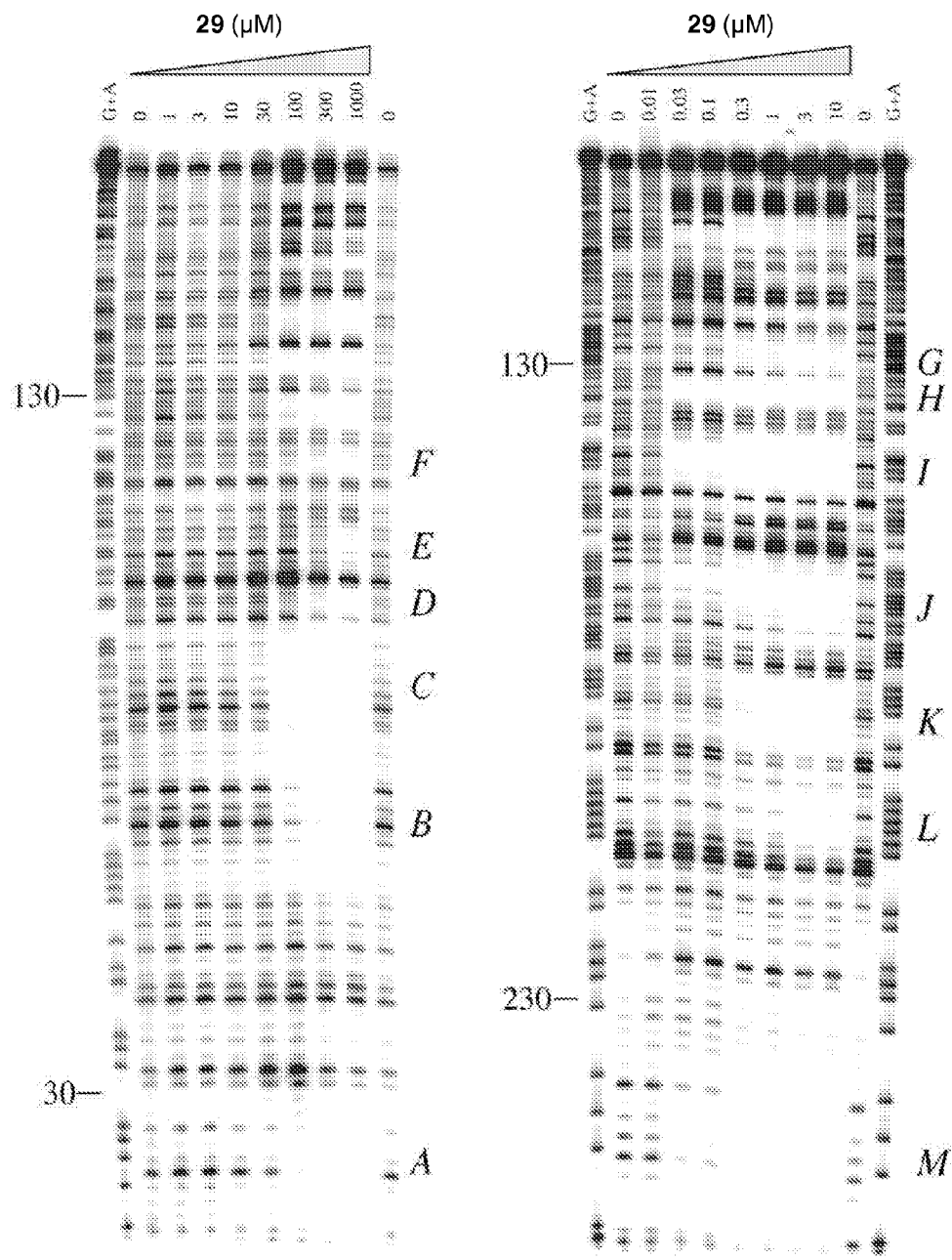
FIG. 2 shows the same as FIG. 1 for 29.
Figure 3:
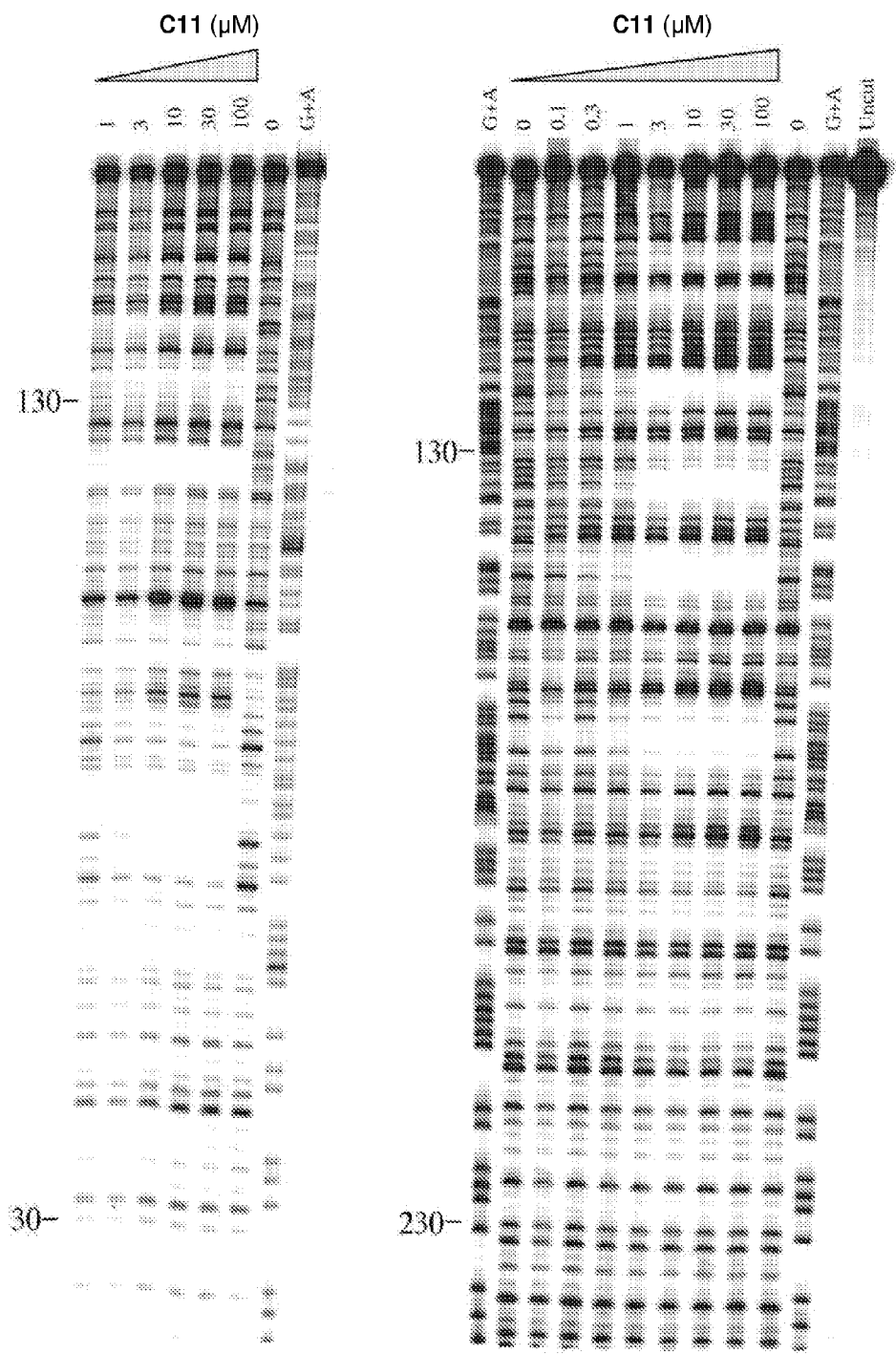
FIG. 3 shows the same as FIG. 1 for C11.

The six conjugates (21, 23, 25, 27, 29) were found to bind to the MS2 fragment at several locations. However, although there were differences in binding affinity between each compound in the set, their footprinting patterns were surprisingly similar. DNase I footprinting gels of 25 (GWL79), the conjugate with the highest TM values, on both MS2F and MS2R DNA fragments are shown in FIG. 1, and those for 29 (GWL81) are shown in FIG. 2.

The vast majority of footprint sites are common features in the binding profiles of all six conjugates, with only a small number of sites being footprinted by a subset of the family. Even more unexpectedly, no site is footprinted by only one molecule (in fact, the fewest number of conjugates that bind at any single site is four). The differential cleavage plot provides footprinting profiles at a supramaximal concentration colour-coded for each conjugate which illustrates a striking degree of overlap. Although there is no conspicuous change in footprinting patterns as the number of pyrroles units in each conjugate increases, there are changes in two other features, namely, the apparent binding affinity and the width of the footprinted site. The binding affinity of each molecule at a particular site was estimated by eye (using the individual DNase I footprint images) as the concentration of conjugate providing 50% inhibition (DNase $IC_{50}$) of DNase I-mediated cleavage at that site. To simplify comparison between molecules, only the most significant footprint site (5'-$^{62}$CAATA-CACA$^{70}$-3'/3'-GTTATGTGT-5') was selected for comparison. When the binding affinity of each molecule is compared to the relative number of pyrrole units it contains, a parabolic relationship is observed. By this method, 27 (four pyrroles) appears to be the strongest binder with a DNase $IC_{50}$ of around 30 nM. Conjugate 25 (three pyrroles) and 29 (five pyrroles) follow closely with affinities in the region of 30-100 nM. Conjugates 23 (2 pyrroles) and 29 (6 pyrroles) are poorer binders but still exhibit nanomolar affinities in the region of 100-300 nM and 300 nM, respectively. Finally, 21 (one pyrrole) is a particularly weak footprinting molecule with an DNase $IC_{50}$ of about, or in excess of, 10 µM.

The binding characteristics of the series (21, 23, 25, 27, 29) at all thirteen sites within the MS2 DNA fragment are provided in detail in table 2.

TABLE 2

| | Footprint Position | | | | | | | | | | | | |
|---|---|---|---|---|---|---|---|---|---|---|---|---|---|
| | A | B | C | D | E | F | G | $H^1$ | I | $J^2$ | K | L | M |
| 21 | − | + | + | − | − | − | + | + | + | + | + | + | + |
| 23 | ++ | ++ | ++ | + | − | ++ | + | +++ | ++ | +++ | +++ | ++ | ++ |
| 25 | +++ | +++ | +++ | +++ | + | +++ | −³ | +++ | +++ | ++ | ++ | +++ | −⁴ |
| 27 | +++ | ++ | ++ | ++ | ++ | + | ++ | +++ | ++ | ++ | ++ | ++ | +++ |
| 29 | ++ | ++ | ++ | ++ | + | ++ | ++ | +++ | +++ | +++ | ++ | ++ | ++ |
| 31 | ++ | ++ | ++ | ++ | + | ++ | ++ | ++ | ++ | + | − | − | + |

[1] 27, 29, 31 show evidence of two closely juxtaposed footprints at this position
[2] 27, 29, 31 show evidence of two closely juxtaposed footprints at this position
[3,4] data not suitable for analysis due to 'smearing' of digestion products at higher concentrations The same site (5'-$^{62}$CAATACACA$^{70}$-3') and its close neighbour 5'-$^{50}$ATCCATATGCG$^{60}$-3' were also chosen and analysed in order to assess the effect of increasing the size of the molecules on the length of the sequence bound. It appears that as additional pyrroles are added to the PBD there is a subsequent rise in the number of base pairs within the associated binding site. Although the precise effects on individual sites cannot be ascertained, the positive correlation is suggestive of larger tracts of DNA becoming bound by molecules of increasing length, although it is not known whether it is a single molecule or more contributing to the observed effect.

Figure 4:
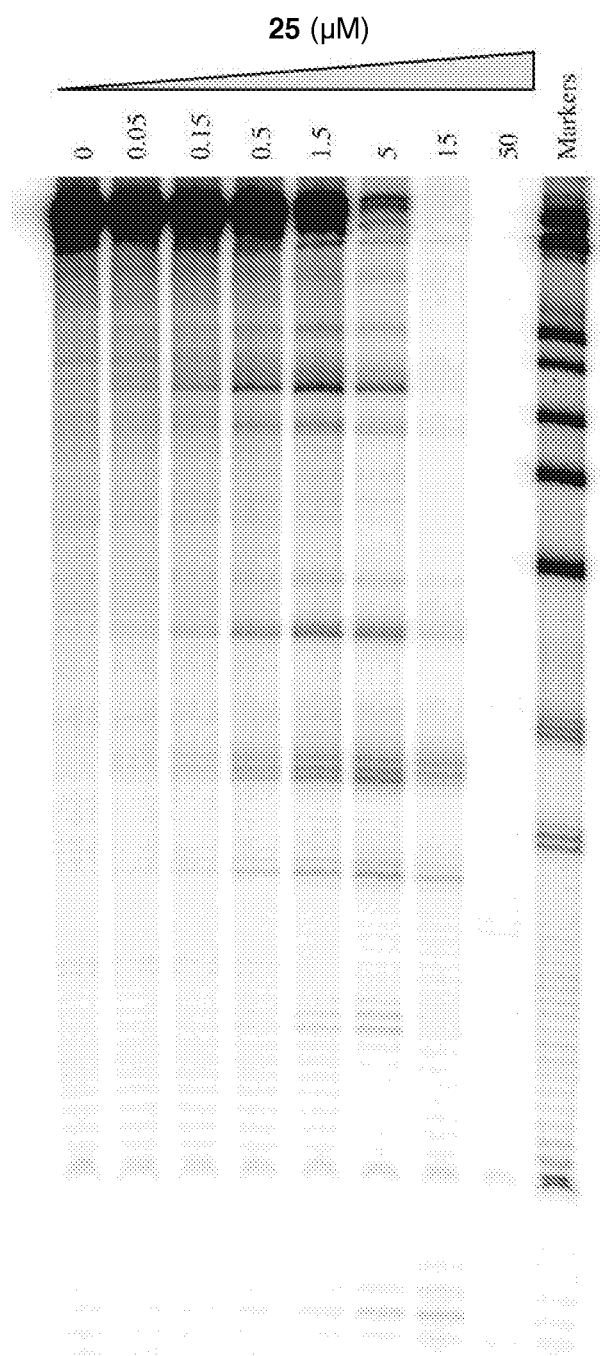
FIG. 4 shows the results of the in-vitro transcription assay for 25.

Conjugate C11 was also assessed for DNA binding by DNase I footprinting (FIG. 4). The results confirm the indication from Tm values that 25 should have a better isohelical fit in the minor groove of DNA and thus a higher reactivity towards DNA. The gel in FIG. 4 indicates that C11 has an apparent binding affinity of approximately 3 µM which is 30 to 100-fold higher than that of 25 (30-100 nM). Furthermore, differential cleavage analysis shows, as expected, that the actual pattern of footprints produced by C11 is almost identical to 25 except for the lack of footprints at positions D, M and G (which is, in fact, footprinted by 21, 23, 27 and 29, and much weaker binding at positions K and L (binding at these sites can only be resolved by a computational method; data not shown).

Example 5

In-Vitro Transcription Assay

The conjugates 21, 23, 25, 27 and 29 were subjected to an in vitro transcription assay as described in Martin, C., et al., (Martin, C., et al., *Biochemistry*, 44(11), 4135-4147 (2005)) to establish whether any members could inhibit transcription. The technique used was as follows.

An extended 282 bp DNA fragment, containing the 262 bp sequence used in footprinting assays and a suitably positioned 5' T7 promoter, was amplified from the MS2 plasmid by PCR with MS2-T7 forward primer (5'-TAATACGACT-CACTATAGGGCAGGAAACAGCTATGAC-3') and reverse primer (see footprinting). The 282-mer product was purified by phenol-$CHCl_3$ extraction and EtOH precipitation before being resuspended in nuclease-free water to a fixed concentration (1 µg/µl).

282-mer (1 µl) was incubated overnight with 1.25× drug solution (4 µl) or water in controls. Transcription mix [5 µl total containing 5× transcription buffer (2 µl), RNasin RNase inhibitor (0.5 µl of 40 U/µl), T7 RNA polymerase (0.25 µl of 20 U/µl), DTT (0.25 µl, 100 mM; all Promega), NTPs (0.5 µl of 25 mM A, C, G and T, Amersham Pharmacia), ($\alpha$-$^{32}$P)-CTP (0.25 µl of 10 µCi/µl, 3000 Ci/mmol, Perkin Elmer Life Sciences) and nuclease-free water (1.25 µl)] was added and synthesis of RNA transcripts was allowed to proceed at 37° C. for 90 minutes. Following the addition of loading dye (10 µl), samples were heated to 94° C. for 4 minutes, briefly cooled on ice and then loaded on to a preheated 8% denaturing polyacrylamide gel. Electrophoresis was performed for 80 minutes in 0.5×TBE buffer at 60 W (2000-2250 V). The gel was then blotted onto Whatman 3 MM paper and dried under vacuum at 80° C. for 45 minutes. Expose to phosphor storage screens and data collection was as for footprinting gels.

Marker lanes were created by restriction enzyme digestion of the 282-mer. Ten different restriction enzymes, each with a single cutting site on the 282-mer, were employed to cleave the template 282-mer DNA in separate reactions according to the manufacturer's guidelines. Cut DNA was pooled and purified by phenol-$CHCl_3$ extraction and EtOH precipitation. DNA was resuspended in nuclease-free water to a fixed concentration (1 µg/µl). Marker DNA (1 µl) was used as a template for transcription as described above, yielding RNA transcripts of known length depending on the enzyme cutting site.

The lengths of attenuated transcripts produced in the presence of drug were calculated by a graphical method. The electrophoresed distance each marker band was accurately measured and a plot of the length of the transcript against this distance was curve-fitted. The electrophoresed distance of each attenuated transcript was then used to determine its approximate length and hence the position of the transcription stop site on the DNA template.

Figure 5:
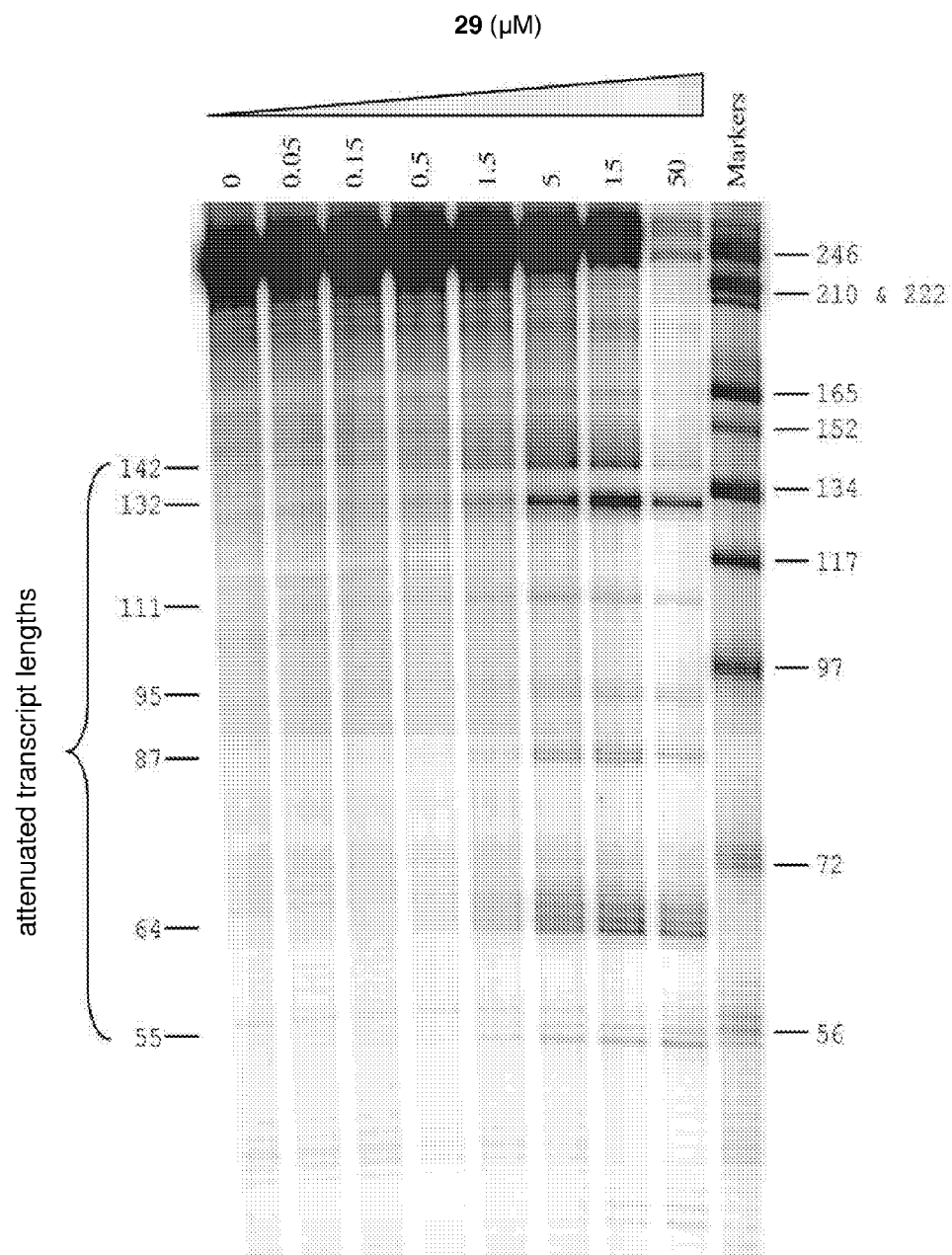
FIG. 5 shows the same as FIG. 4 for 29.
Figure 6:
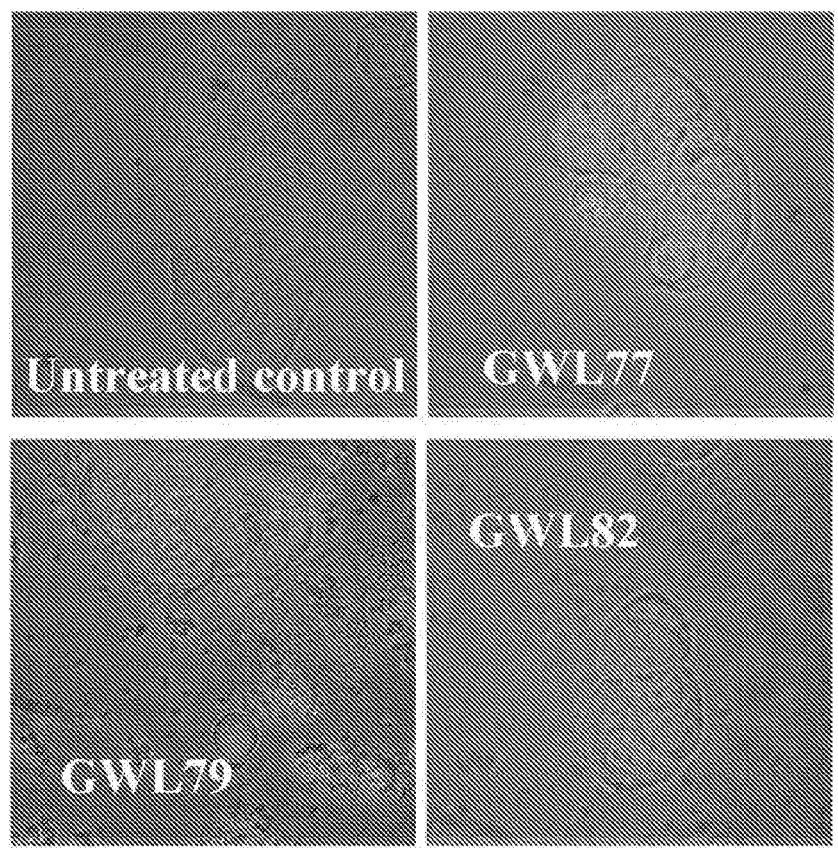
FIG. 6 are confocal microscopy pictures of MCF-7 human mammary cells following treatment with compounds of the invention.
Figure 7:
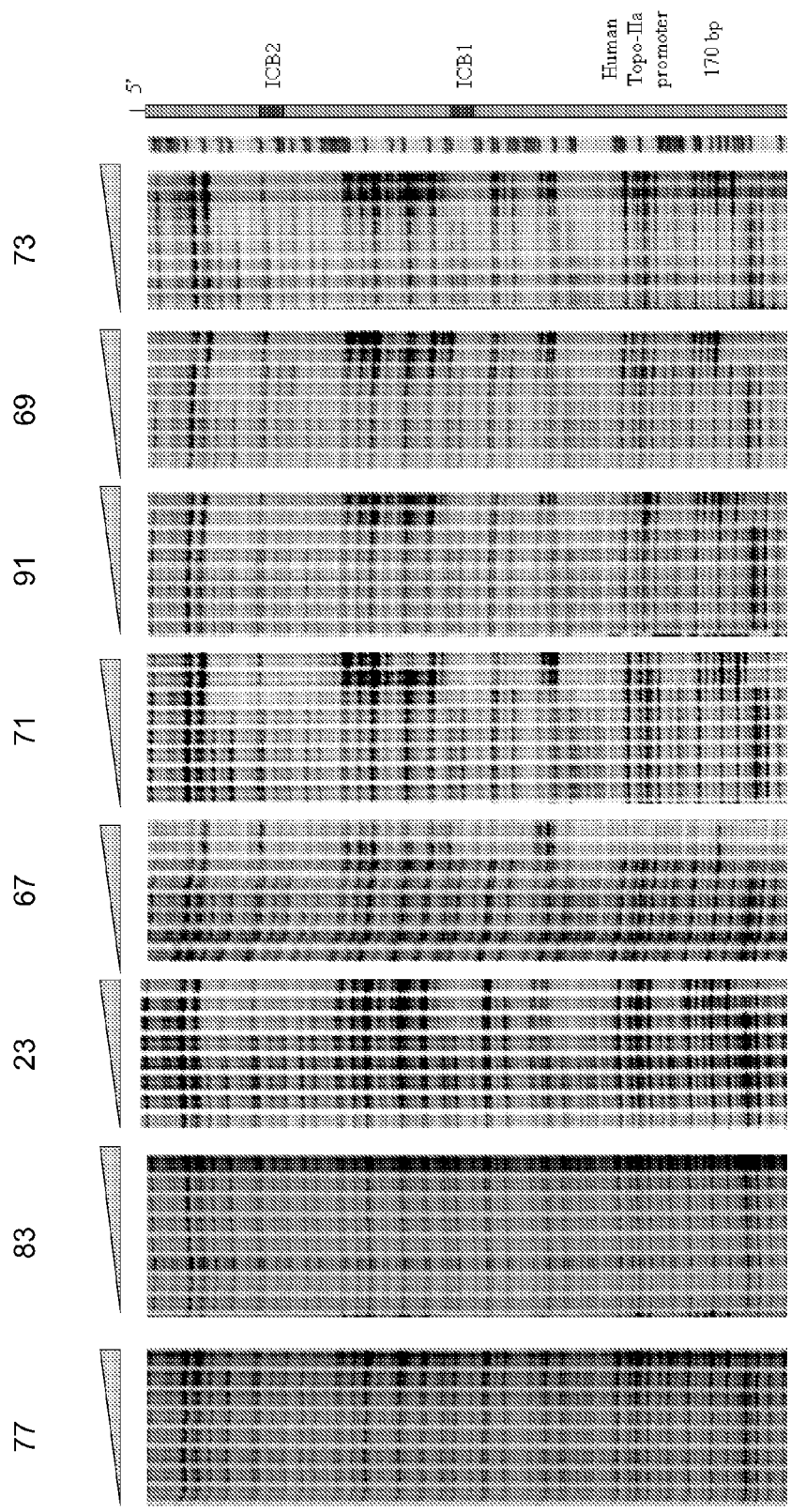
FIG. 7 shows Dnase I footprint gel of compounds of the invention against 170 bp of the human Topo-IIa promoter.

As with the DNase I footprinting results, each member produced identical T-stop patterns. Results for 25 and 29 are shown in FIGS. 5 and 6, respectively, and are representative of all other compounds in the series. It is significant that all seven observed T-stops localise within a few bases of the most intense footprints produced by the same compounds; the correlation is highlighted in FIG. 7 where the T-Stops are depicted as asterisks. Those with transcript lengths of 55 (51), 64 (60), 95 (91), 111 (107) and 142 (138) nucleotides are found 5'- to the likely binding sites. The remaining two T-stops are located only one or two base pairs 3'- to the nearest footprint.

In general, all compounds provide T-stops within the same concentration range, producing 50% inhibition of full-length transcript synthesis at around 5 µM. However, the use of this particular assay in determining, or even estimating, affinity constants has not been validated and therefore only sequence data can be analysed.

In accordance with the DNase I footprinting data, C11 produces T-stops at identical positions to 25 (data not shown) and the remainder of the series, with one exception; the T-stop corresponding to a 132 nt transcript. This corresponds well with the lack of footprinting around this site by C11. The range of concentrations over which C11 exerts its effect is similar to that of 25, however, the use of this assay to compare effective concentration ranges has not been validated.

Example 6

In Vitro Cytotoxicity

K562 human chronic myeloid leukaemia cells were maintained in RPM1 1640 medium supplemented with 10% fetal calf serum and 2 mM glutamine at 37° C. in a humidified atmosphere containing 5% $CO_2$ and were incubated with a specified dose of drug for 1 hour at 37° C. in the dark. The incubation was terminated by centrifugation (5 min, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 µL of MTT solution (5 mg/mL in phosphate-buffered saline) was added to each well and the plates further incubated for 5 hours. The plates were then centrifuged for 5 minutes at 300 g and the bulk of the medium pipetted from the cell pellet leaving 10-20 µL per well. DMSO (200 µL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value. The results are shown in table 3 below.

TABLE 3

| Compound | $IC_{50}$ (µM) |
|---|---|
| C11 | 0.346 |
| 21 | 0.051 |
| 23 | 0.0036 |
| 25 | 0.041 |
| 27 | 0.047 |
| 29 | 0.083 |
| 31 | 0.032 |

Example 7

Cellular and Nuclear Penetration

Cellular uptake and nuclear incorporation of drug into MCF-7 human mammary cells was visualised using confocal microscopy. Conjugates 21, 23, 26, 27 and 29 were prepared in DMSO at 20 mM and diluted in RPMI to the appropriate concentration. Freshly harvested MCF7 cells at $5 \times 10^4$ cells/ ml were placed in 200l of complete RPMI1640 (containing 10% FCS) into the wells of 8-well chambered cover-glasses. Cells were left overnight to adhere at 37° C. Following overnight incubation, cellular preparations were spiked with concentrations of compound at 1, 10 and 100 µM ensuring that final DMSO concentrations were <1%. At 1, 5 and 24 hours after addition of conjugates, the cells were examined using a Nikon TE2000 with UV filter set and viewed under oil immersion with the x63 objective lens. The results for conjugates 21, 26 and 27 at 200 µM over 24 hours are shown in FIG. 8.

At the highest drug concentrations used and an exposure time of 24 hour it is clear that all compounds are taken up into MCF-7 cells. With 21, 23 and 25 there is strong nuclear fluorescence, but with 27, 29 and 31 the fluorescence appears more diffuse throughout the cell (which does not mean that it is not nuclear). In general the longer the conjugate the slower the uptake with 21 being taken up very rapidly (<1 hour) and the others (23 and 25) detectable after 3 hours. Although high concentrations of conjugates were used in these experiments, they did not appear to be detrimental to the cells over a period of 24 hours. $IC_{50}$ values for MCF-7 in comparison are in the range of 2 µM. The main observations are that cellular uptake is observed for all conjugates at a concentration of 200 µM over 24 hour, with clear nuclear uptake seen for 21, 23 and 25.

Example 7

Further DNA Footprinting

In a similar manner to Example 4, the affinity and sequence selectivity of certain compounds of examples 1 and 2 was evaluated by standard DNA footprinting on a 170 bp sequence of the human Topo-IIa promoter, in accordance with the technique described in Martin, C., et al.

Selected results are shown in FIG. 9, wherein the concentrations of the lanes were 0, 1.6, 8, 40, 200, 1000, 5000 and 25000 nM in each case.

The footprinting results allowed the identification of compounds that could potentially disrupt transcription factor binding at the ICB1 and ICB2 sites. Eight molecules were chosen, six of which demonstrated significant binding at the crucial ICB sites. The remaining two compounds did not footprint at any sequence of the DNA fragment and therefore, are useful for control purposes in the functional assay. These compounds are detailed below in table 3, showing the concentrations (µM) at which the PBD-heterocycle conjugates bind at ICB1 and ICB2.

TABLE 3

| Compound | Concentration (µM) at which DNA binding is observed | |
|---|---|---|
|  | ICB1 | ICB2 |
| 23 | 1 | 1 |
| 67 | 5 | 1 |
| 71 | 1 | 5 |
| 91 | 5 | 5 |
| 77 | — | — |
| 69 | 5 | 5 |
| 73 | 5 | 1 |
| 83 | — | — |

Example 8

NF-Y Gel Shift Assay

Eight members of the PBD-heterocycle conjugate library were selected to be evaluated in the NF-Y gel shift assay. Compounds that had the potential to disrupt NF-Y transcription factor binding were identified by footprinting studies, as previously reported. Six of the eight chosen molecules were seen to bind at the inverted CCMT box (ICBs) sites on Topoisomerase IIα promoter with reasonably high affinity. Of the remaining compounds, one only footprinted at the highest concentration (25 µM) and the other did not bind to any DNA sequence.

The assay was performed at ICB1 and ICB2, the sequences for which are shown below:
ICB1 5' CAGGGATTGGCTGGT 3'
ICB2 5' CTACGATTGGTTCTT 3'
Experimental Protocol
Cell Lines and Culture Conditions NIH3T3 cells (obtained from CR-UK London Research Institute) were grown in Dulbecco's MEM High Glucose (DMEM) (Autogen Bioclear) supplemented with 10% newborn calf serum (NBCS), 1% glutamine and incubated at 37° C. in 5% $CO_2$. HCT116 cells were also obtained from CR-UK London Research Institute and grown in RPMI medium (Bioclear) supplemented with 10% foetal calf serum (FCS), 1% glutamine and incubated at 37° C. in 5% $CO_2$.
Preparation of Nuclear Extracts.

Nuclear extracts were essentially prepared as described (Firth et al, Proc. Natl Acad Sci USA, 91:6496-6500, 1994) and all steps were performed at 4° C. in the presence of a protease inhibitor mix (Complete™, Boehringer). Briefly, cells were rinsed with ice-cold phosphate buffered saline (PBS), scraped from the surface and collected by centrifugation. The cells were washed with 5 equivolumes of hypotonic buffer containing 10 mM K-Hepes pH 7.9, 1.5 mM $MgCl_2$, 10 mM KCl, 0.5 mM dithiothreitol (DTT, Sigma). Subsequently, the cells were re-suspended in 3 equivolumes hypotonic buffer, incubated on ice for 10 min, subjected to 20 strokes of a Dounce homogenizer and the nuclei were collected by centrifugation. The nuclear pellet was re-suspended in 0.5 equivolumes low salt buffer containing 20 mM K-Hepes pH7.9, 0.2 mM K-EDTA, 25% glycerol, 1.5 mM $MgCl_2$, 20 mM KCl, 0.5 mM DTT. While stirring, 0.5 equivolume high salt buffer (as low salt buffer but containing 1.4M KCl) was added and the nuclei were extracted for 30 min. Subsequently, the mixture was centrifuged for 30 min at 14,000 rpm in an eppendorf centrifuge and the supernatant was dialysed in tubing with a 12 kDa cut off (Sigma) for 1 hr in a 100 times excess of dialysis buffer containing 20 mM K-Hepes pH7.9, 0.2 mM K-EDTA, 20% glycerol, 100 mM KCl, 0.5 mM DTT. The dialysed fraction was centrifuged for 30 min at 14,000 rpm in an eppendorf centrifuge and the supernatant was snap frozen in an ethanol dry ice bath and stored at −80° C. The protein concentration of the nuclear extract was assayed using a BIO-RAD micro protein assay kit.
Electrophoretic Mobility Shift Assay (EMSA).

The oligonucleotides (MWG Biotech) containing ICBs (underlined) used in EMSAs are were Topo IIα ICB1 sense: 5'-CGAGTCAGGGATTGGCTGGTCTGCTTC-3', antisense: 5'-GAAGCAGACCAGCCAATCCCTGACTCG-3'; ICB2 sense: 5'-GGCAAGCTACG ATTGGTTCTTCTGGACG-3', antisense: 5'-CGTCCA-GAAGAACCAATCGTAGCTTGCC-3'; ICB3 sense: 5'-CTCCC TAACCTGATTGGTTTATTCAAAC-3', antisense: 5'-GTTTGAATAAACCAATCAGGT TAGGGAG-3' and ICB4 sense: 5'-GAGCCCTTCTC ATTGGCCAGATTCCCTG-3', antisense: 5'-CAGG-GAATCTGGCCAATGAGAAGGGCTC-3'. Oligonucleotides corresponding to mdr1 sense: 5'-GTGGTGAGGCTG ATTGGCTGGGCAGGAA-3', antisense: 5'-TTCCTGC-CCAGCCAATCAGCCTCACCA-3'; hOGG1 sense: 5'-AC- CCTGATTTCTCATTGGCGCCTCCTACCTCCTCCTCG-GATTGGCTACCT-3', antisense: 5'-AGGTAGCCAATCCG-AGGAGGAGGTAGGAGGCGCCAATGAGAAATCAGG-GT-3'; cdc2/cdk1 sense: 5'-CGGGCTACCCGATTGGTG-AATCCGGGGC-3', antisense: 5'-GCCCCGGATTCACCA-ATCGGGTAGCCCG-3' and cyclin B1 CCAAT box 1 sense: 5'-GACCGGCAGCCGCCAATGGGAAGGGAGTG-3', antisense: 5'-CACTCCCTTCCC ATTGGCGGCTGCCGG-TC-3' and CCAAT box 2 sense: 5'-CCACGAACAGG-CCAATAAGGAGGGAGCAG-3', antisense: 5'-CTGCTC-CCTCCT TATTGGCCTGTTCGTGG-3' were also used for EMSA. Oligonucleotides containing mutated ICBs were used as specific competitors of similar sequence, except the wild-type ICB sequence was replaced by AAACC or GGTTT, in sense and antisense oligonucleotides, respectively. Sense and antisense oligonucleotides were annealed in an equimolar ratio. Double stranded oligonucleotides were 5' end labelled with T4 kinase (NEB) using $\gamma$-$^{32}$P-ATP and subsequently purified on Bio-Gel P-6 columns (BIO-RAD). EMSAs were essentially performed as described (Firth et al, Proc. Natl. Acad Sci USA, 91:6496-6500, 1994). Briefly, 5 µg nuclear extract in a total volume of 10 µl was incubated at 4° C. for 30 minutes in a buffer containing 20 mM K-Hepes pH7.9, 1 mM MgCl$_2$, 0.5 mM K-EDTA, 10% glycerol, 50 mM KCl, 0.5 mM DTT, 0.5 µg poly(dI-dC). poly(dI-dC) (Pharmacia) and 1× protease inhibitor mix (Complete™, Boehringer). For supershifts, antibodies against NF-YA (IgG fraction, Rocklands) were used and the pre-incubation on ice was extended for a total of 1.5 hour. Upon addition of approximately 0.1 ng radio-labelled probe the incubation was continued for 2 hours at room temperature. In competition experiments, radiolabelled probe and competitor were added simultaneously. Subsequently, 0.5 µl loading buffer (25 mM Tris-Cl pH7.5, 0.02% BFB and 10% glycerol) was added and the samples were separated on a 4% polyacrylamide gel in 0.5×TBE containing 2.5% glycerol at 4° C. After drying the gels the radioactive signal was visualized by exposing the gels to Kodak X-Omat-LS film Results Four molecules were tested in the EMSA gel shift assay at ICB1, the results of which are shown below in Table 4. The pyrrole dimer molecule 23 inhibited NF-Y binding at the lowest concentration (5 µM). RMH057 did not inhibit NF-Y binding at the concentrations used.

TABLE 4

| Compound | Lowest concentration at which NF-Y binding inhibition was observed (µM) |
|---|---|
| 23 | 5 |
| 67 | 50 |
| 69 | 50 |
| 91 | — |

The selected PBD-heterocycle conjugates were tested in the EMSA gel shift assay at ICB2, the results of which are shown below in Table 5. Again, the pyrrole dimer molecule inhibited NF-Y binding at the lowest concentration (5 µM). Interestingly, 67 also inhibited NF-Y binding at ICB2 at 5 µM.

TABLE 5

| Compound | Lowest concentration at which NF-Y binding inhibition was observed (µM) |
|---|---|
| 67 | 5 |
| 23 | 5 |
| 69 | 10 |
| 73 | 10 |
| 71 | 10 |
| 91 | 50 |
| 77 | 50 |
| 83 | — |

The invention claimed is:

1. A compound of formula I:

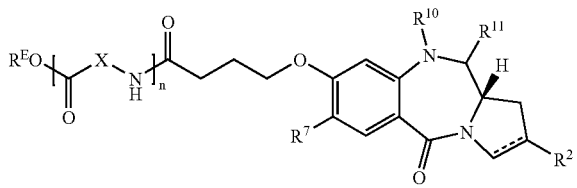

or a salt thereof, wherein:
the dotted line indicates the optional presence of a double bond between C2 and C3;
$R^2$ is selected from —H, —OH, =O, =CH$_2$, —CN, —R, OR, halo, =CH—R, O—SO$_2$—R, CO$_2$R and COR;
$R^7$ is selected from H, R, OH, OR, SH, SR, NH$_2$, NHR, NRR', nitro, Me$_3$Sn and halo;
where R and R' are independently selected from optionally substituted C$_{1-7}$ alkyl, C$_{3-20}$ heterocyclyl and C$_{5-20}$ aryl groups;
$R^{10}$ and $R^{11}$ either are selected from H and YR$^Y$, where Y is selected from O, S and NH and R$^Y$ is H or C$_{1-7}$ alkyl or H and SO$_x$M where x is 2 or 3, and M is a monovalent pharmaceutically acceptable cation or are absent and a double bond is formed between the atoms bearing $R^{10}$ and $R^{11}$;
each X is an N-methyl substituted pyrrole;
n is from 1 to 6;
$R^E$ is C$_{1-4}$ alkyl.

2. A compound according to claim 1, wherein n is from 2 to 6.

3. A compound according to claim 1, wherein $R^7$ is independently selected from H and OR, where R is selected from optionally substituted C$_{1-7}$ alkyl, C$_{3-10}$ heterocyclyl and C$_{5-10}$ aryl groups.

4. A compound according to claim 1, wherein $R^{10}$ and $R^{11}$ either form a double bond together or $R^{11}$ is selected from H and OR$^Y$, where R$^Y$ is H or Me.

5. A compound according to claim 1, wherein $R^E$ is C$_{1-2}$ alkyl.

6. A pharmaceutical composition comprising a compound according to claim 1 and a pharmaceutically acceptable carrier or diluent.

7. A method of treatment of a patient suffering from a proliferative disease, comprising administering to said patient a therapeutically acceptable amount of a compound according to claim 1 or a composition according to claim 6.

* * * * *

UNITED STATES PATENT AND TRADEMARK OFFICE
CERTIFICATE OF CORRECTION

PATENT NO. : 8,637,664 B2
APPLICATION NO. : 12/089459
DATED : January 28, 2014
INVENTOR(S) : Howard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 720 days.

Signed and Sealed this
Twenty-second Day of September, 2015

Michelle K. Lee
*Director of the United States Patent and Trademark Office*